United States Patent [19]

Böhm et al.

[11] Patent Number: 6,030,972
[45] Date of Patent: Feb. 29, 2000

[54] DIPEPTIDE AMIDINES AS THROMBIN INHIBITORS

[75] Inventors: Hans-Joachim Böhm, Limburgerhof; Hans Wolfgang Höffken, Ludwigshafen; Wilfried Hornberger, Neustadt; Stefan Koser; Helmut Mack, both of Ludwigshafen; Thomas Pfeiffer, Böhl-Iggelheim; Werner Seitz, Plankstadt; Thomas Zierke, Böhl-Iggelheim, all of Germany

[73] Assignee: BASF Aktiengesellschaft, Ludwigshafen, Germany

[21] Appl. No.: 08/894,252

[22] PCT Filed: Feb. 12, 1996

[86] PCT No.: PCT/EP96/00582

§ 371 Date: Jul. 30, 1997

§ 102(e) Date: Jul. 30, 1997

[87] PCT Pub. No.: WO96/25426

PCT Pub. Date: Aug. 22, 1996

[30] Foreign Application Priority Data

Feb. 17, 1995 [DE] Germany ............... 195 05 484
Feb. 24, 1995 [DE] Germany ............... 195 06 611
Mar. 3, 1995 [DE] Germany ............... 195 07 455

[51] Int. Cl.[7] ................ A61K 31/505; C07D 239/42
[52] U.S. Cl. ................. 514/257; 514/269; 544/242; 544/319; 544/326; 544/334; 544/335
[58] Field of Search .................... 544/242, 319, 544/326, 334, 335; 514/257, 269

[56] References Cited

U.S. PATENT DOCUMENTS 4,346,078  8/1982  Bajusz et al. .................... 424/177

FOREIGN PATENT DOCUMENTS

| | | |
|---|---|---|
| 118 280 | 9/1984 | European Pat. Off. . |
| 185 390 | 6/1986 | European Pat. Off. . |
| 195 212 | 9/1986 | European Pat. Off. . |
| 293 881 | 12/1988 | European Pat. Off. . |
| 362 002 | 4/1990 | European Pat. Off. . |
| 364 344 | 4/1990 | European Pat. Off. . |
| 410 411 | 1/1991 | European Pat. Off. . |
| 471 651 | 2/1992 | European Pat. Off. . |
| 503 203 | 9/1992 | European Pat. Off. . |
| 526 877 | 2/1993 | European Pat. Off. . |
| 530 167 | 3/1993 | European Pat. Off. . |
| 542 525 | 5/1993 | European Pat. Off. . |
| 589 741 | 3/1994 | European Pat. Off. . |
| 699 317 | 8/1995 | European Pat. Off. . |
| 672 658 | 9/1995 | European Pat. Off. . |
| 31 08 810 | 5/1982 | Germany . |
| 44 21 052 | 12/1995 | Germany . |
| 92/07869 | 5/1992 | WIPO . |
| 93/15756 | 8/1992 | WIPO . |
| 93/11152 | 6/1993 | WIPO . |
| 93/18060 | 9/1993 | WIPO . |
| 94/08941 | 4/1994 | WIPO . |
| 94/29336 | 12/1994 | WIPO . |
| 95/23609 | 9/1995 | WIPO . |
| 95/29189 | 11/1995 | WIPO . |
| 95/29691 | 11/1995 | WIPO . |
| 95/35309 | 12/1995 | WIPO . |
| WO 96125426 | 8/1996 | WIPO . |

OTHER PUBLICATIONS

Klimkowski et al., Chemical Abstracts, vol. 128, abstract 102395, 1998.
Folia Haematologica, 109 Band, 1982, 42–51.
J. Med Chem 1994, 37, 266–231.
Database crossfire 4328–4331, 1900.
Database crossfire, BRN 2716610 & BRN 3030402, 1975.
Chem. Abst. DE 4421052, 1995.

*Primary Examiner*—Richard L. Raymond
*Attorney, Agent, or Firm*—Keil & Weinkauf

[57] ABSTRACT

Compounds of the formula

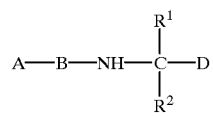

where A, B, D, $R^1$ and $R^2$ have the meanings stated in the description, are described. The compounds are suitable for controlling diseases.

The novel compounds are prepared via compounds of the formula

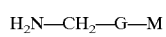

1 Claim, No Drawings

DIPEPTIDE AMIDINES AS THROMBIN INHIBITORS

The present application is a 371 of PCT/EP 96/00582, filed Feb. 12, 1996.

The present invention relates to novel carbo- and heterocyclic amidines, the preparation thereof and the use thereof as thrombin inhibitors.

Thrombin belongs to the group of serine proteases and plays a central part in the blood coagulation cascade as terminal enzyme. Both the intrinsic and the extrinsic coagulation cascades lead via several amplification stages to the production of thrombin from prothrombin. The thrombin-catalyzed cleavage of fibrinogen to fibrin then initiates the coagulation of blood and the aggregation of the platelets which in turn enhance, owing to the binding of platelet factor 3 and coagulation factor XIII and a whole series of highly active mediators, the formation of thrombin.

The formation and action of thrombin are central events in the production both of white, arterial and of red, venous thrombi and therefore potentially effective points of attack for drugs. Thrombin inhibitors are, in contrast to heparin, able to inhibit completely, independently of cofactors, simultaneously the actions of free thrombin and that bound to platelets. They are able to prevent in the acute phase thromboembolic events after percutaneous transluminal coronary angioplasty (PTCA) and lysis and to act as anticoagulants in extracorporeal circulation (heart-lung machine, hemodialysis). They can also be generally used for the prophylaxis of thrombosis, for example after surgical operations.

It is known that synthetic arginine derivatives influence the enzymatic activity of thrombin by interacting with the active serine residue of the protease thrombin. Peptides based on Phe—Pro—Arg in which the N-terminal amino acid is in the D form have proved to be particularly beneficial. D—Phe—Pro—Arg isopropyl ester has been described as a competitive thrombin inhibitor (C. Mattson et al., Folia Haematol, 109 (1983) 43–51).

Derivatization of the C-terminal arginine to the aldehyde leads to an enhancement of the inhibitory effect. Thus, a large number of arginals able to bind the hydroxyl group of the "active" serine in the form of a hemiacetal have been described (EP 185 390, 479 489, 526 877, 542 525; WO 93/15756, 93/18060).

The thrombin-inhibitory activity of peptide ketones, fluorinated alkyl ketones and of keto esters, boric acid derivatives, phosphoric esters and α-keto carboxamides can likewise be explained by this interaction with serine (EP 118 280, 195 212, 362 002, 364 344, 410 411, 471 651, 589 741, 293 881, 503 203, 504 064, 530 167; WO 92/07869, 94/08941).

DE 31 08 810 and WO 93/11152 describe ω-aminoalkylguanidine dipeptides.

The diphenyl 4-amidinophenylglycinephosphonate peptides described by J. Oleksyszyn et al. in J. Med. Chem. 37 (1994) 226–231 are irreversible thrombin inhibitors with inadequate selectivity with respect to other serine proteases.

WO 94/29336 and WO 95/23609 describe benzylamidines as thrombin inhibitors.

The invention relates to compounds of the formula I

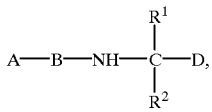

I and the salts thereof with physiologically tolerated acids and the stereoisomers thereof, in which the substituents have the following meanings:

$R^1$: H, $C_{1-4}$-alkyl;

$R^2$: H, $C_{1-4}$-alkyl, phenyl, phenyl-$C_{1-4}$-alkyl; $R^{18}O$—$CH_2$—, $R^{18}$—CO—, $R^{18}$—O—$CH_2$—CO—, $R^{18}O$—CO—CO—, $R^{18}$—H—CO—CO—, where $R^{18}$ is H, $C_{1-4}$-alkyl, phenyl-$C_{1-4}$-alkyl or phenyl, or $CF_3$—CO—, $C_2F_5$—CO— or $C_{1-4}$-alkyl-O—CO—,

A:

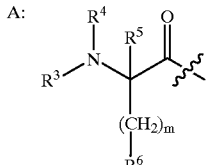

IIa

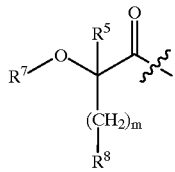

IIb

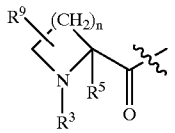

IIc in which the substituents have the following meanings:

m: 0 or 1, n: 1, 2, 3 or 4, $R^3$: H, $C_{1-12}$-alkyl, aryl-$C_{1-4}$-alkyl, $R^{19}OOC$—$C_{1-6}$-alkyl ($R^{19}$=H, $C_{1-4}$-alkyl, benzyl), $HO_3S$—$C_{1-3}$-alkyl, $C_{1-12}$-alkyl-CO—, aryl-CO—, aryl-$C_{1-4}$-alkyl-CO—, $R^{19}OOC$-$C_{1-6}$-alkyl-CO—, $HO_3S$—$C_{1-3}$-alkyl-CO—, $C_{1-7}$-alkyl-OOC—, benzyl-OOC—, or $R^{20}R^{21}N$—CO— ($R^{20}$ and $R^{21}$ are identical or different and are H, $C_{1-6}$-alkyl, aryl, aryl-$C_{1-4}$-alkyl, $R^{19}OOC$—$C_{1-4}$-alkyl and $R^{19}$—NH—CO—$C_{1-}$-alkyl, where $R^{20}$ and $R^{21}$ may also together be a —$(CH_2)_{3-6}$— group), or $R^{19}$—O—

$R^4$: H, $C_{1-12}$-alkyl, aryl-$C_{1-4}$-alkyl or $R^{19}OOC$—$C_{1-4}$-alkyl ($R^{19}$=H, $C_{1-4}$-alkyl, benzyl), $R^5$: H, $C_{1-4}$-alkyl or benzyl, $R^6$: $C_{3-8}$-cycloalkyl, where the aliphatic rings can be provided with up to 4 $C_{1-4}$-alkyl and/or $CH_3O$ groups, and one or more methylene group(s) can be replaced by —O—, —S— or N—$C_{1-4}$-alkyl, phenyl which can be substituted by up to 3 identical or different radicals from the group of $C_{1-4}$-alkyl, $CF_3$—, $C_{1-4}$-alkoxy, F— or Cl—, $R^{25}R^{26}CH$—, where $R^{25}$ is $C_{1-6}$alkyl and $R^{26}$ is H or $C_{1-6}$-alkyl, adamantyl, norbornyl—, 1-decalinyl—, 1-tetralinyl—, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl-C(CH$_3$)$_2$—, phenyl-CH(CH$_2$—CH$_2$—OR$^{19}$)—, C$_{1-4}$-alkyl-C≡C—, aryl-C≡C—, (CH$_3$)$_3$Si—, R$^{19}$—S—CH$_2$—, R$^{22}$O—C(R$^{23}$R$^{24}$)—, where R$^{22}$ is H, C$_{1-4}$-alkyl, phenyl, benzyl or C$_{1-4}$-alkyl-CO—, R$^{23}$ is H, C$_{1-4}$-alkyl, HO—C$_{1-3}$-alkyl, phenyl or benzyl and R$^{24}$ is H, C$_{1-4}$-alkyl, HO—C$_{1-3}$-alkyl, phenyl or benzyl, R$^7$: H, C$_{1-12}$-alkyl, C$_{1-20}$-alkyl-CO—, R$^{19}$OOC—C$_{1-4}$-alkyl, R$^{19}$OOC—C$_{1-4}$-alkyl-CO—, R$^{19}$NH—CO—C$_{1-4}$-alkyl, R$^{20}$R$^{21}$N—CO—, HO$_3$S—C$_{1-4}$-alkyl, HO$_3$S—C$_{1-4}$-alkyl-CO—, 5-(1H)-tetrazolyl-CH$_2$— or (R$^{19}$O)$_2$OP—CH$_2$— or the acyl radical or a natural or unnatural bile acid, R$^8$: phenyl which can be substituted by 1 to 3 identical or different radicals from the group of F, Cl, C$_{1-3}$-alkyl, C$_{1-3}$-alkyl-O—, HO— or CF$_3$—, C$_{3-8}$-cycloalkyl, where the aliphatic rings can be provided with up to 4 C$_{1-4}$-alkyl and/or CH$_3$O groups, and one or more methylene group(s) can be replaced by —O—, —S— or N—C$_{1-4}$-alkyl, R$^{25}$R$^{26}$CH— in which R$^{25}$ is C$_{1-6}$-alkyl, C$_{5-8}$-cycloalkyl or phenyl, which can be substituted by 1 to 3 F, Cl, C$_{1-3}$-alkyl, C$_{1-3}$-alkyl-O—, HO— or CF$_3$, and R$^{26}$ is H or has one of the meanings stated for R$^{25}$, or R$^{22}$O—CH$_2$—, adamantyl, norbornyl, 1-decalinyl, 1-tetralinyl, 2-tetralinyl, 1-indanyl, 2-indanyl, C$_{1-4}$-alkyl-C≡C, aryl-C≡C, (CH$_3$)$_3$Si or dibenzosuberyl which can be monosubstituted on one or both aromatic rings, R$^9$: H, C$_{1-4}$-alkyl, aryl or C$_{5-6}$-cycloalkyl (R$^9$ can in accordance with formula IIc be a substituent on all ring positions apart from positions 1 and 2)

B:

IIIa
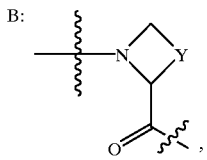

IIIb
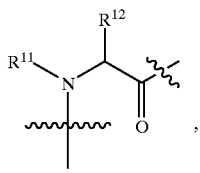

IIIc
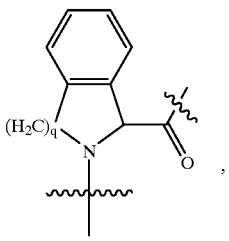

IIId
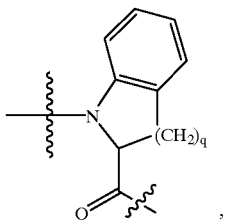

IIIe
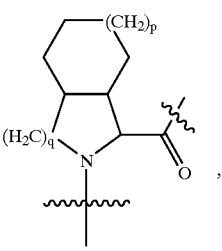

IIIf
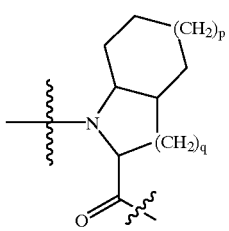

or

IIIg
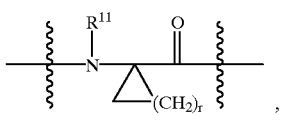

in which the substituents R$^{10}$, R$^{11}$ and R$^{12}$, and p, q, r and Y, have the following meanings:

p: 0 or 1 q: 1 or 2 r: 1, 2, 3, 4 or 5

Y a methylene group, an ethylene group in which the ring resulting therefrom can carry in position 4 a hydroxyl, oxo or C$_{1-4}$-alkoxy group, —CH$_2$—S—, —CH$_2$—SO—, —CH$_2$—O—, —CH=CH— or a propylene group, in which the ring resulting therefrom can carry on the carbon in position 3 and/or 4 a C$_{1-4}$-alkyl group or in which a CH$_2$ group can be replaced by —O—, —S— or —SO—, R$^{10}$: H, C$_{1-4}$-alkyl or phenyl, R$^{11}$: H, C$_{1-4}$-alkyl, C$_{3-8}$-cycloalkyl, phenyl or benzyl, $R^{12}$: H, $C_{1-6}$-alkyl, $C_{3-8}$-cycloalkyl, phenyl or benzyl,

D:

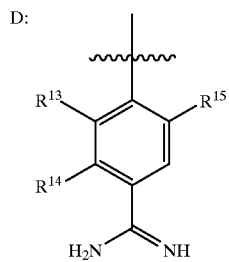
IVa

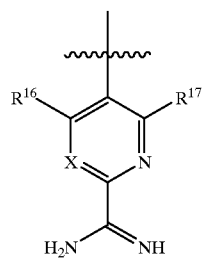
IVb

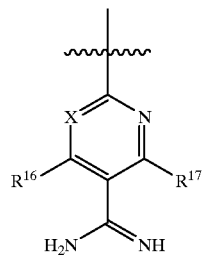
IVc

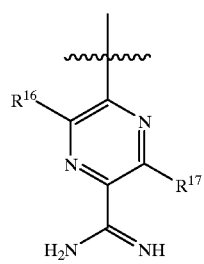
IVd

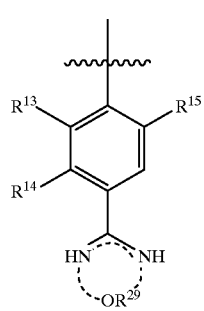
IVe

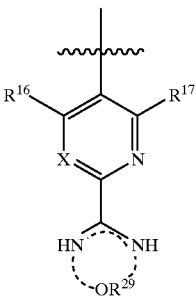
IVf

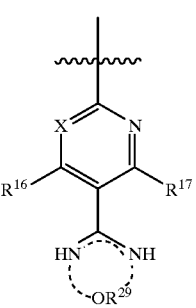
IVg

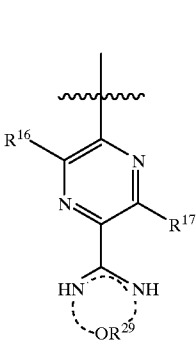
IVh

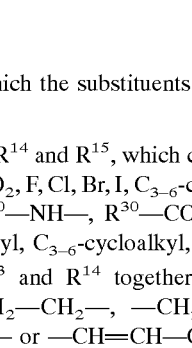

in which the substituents have the following meanings:

$R^{13}$, $R^{14}$ and $R^{15}$, which can be identical or different, are H, $NO_2$, F, Cl, Br, I, $C_{3-6}$-cycloalkyl, $R^{30}$—O—, $R^{30}$OOC—, $R^{30}$—NH—, $R^{30}$—CO—NH—, where $R^{30}$ is H, $C_{1-6}$-alkyl, $C_{3-6}$-cycloalkyl, benzyl or phenyl, or $R^{13}$ and $R^{14}$ together are the chains —$CH_2$—$CH_2$—$CH_2$—$CH_2$—, —$CH_2$—$CH_2$—$CH_2$—, —O—$CH_2$—O— or —CH=CH—CH=CH—, $R^{16}$: H, F, Cl, $C_{1-4}$-alkyl, phenyl-$C_{1-2}$-alkyl, phenyl, $R^{31}$OOC— ($R^{31}$=H, $C_{1-4}$-alkyl, phenyl or benzyl), $R^{31}$—NH—, $R^{31}$—O— or $R^{31}$OOC—$CH_2$—O—, $R^{17}$: H, F, Cl, $C_{1-4}$-alkyl, phenyl-$C_{1-2}$-alkyl, phenyl, $R^{31}$OOC—, $R^{31}$—NH—, $R^{31}$—O— or $R^{31}$OOC—$CH_2$—O—, $R^{29}$: H or $C_{1-4}$-alkyl, $C_{1-4}$-alkoxy, $C_{1-4}$-alkoxy-CO, X: =CH— or =N—.

Preferred compounds are from the following groups Ia to Ii:

Ia:

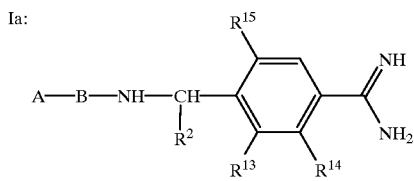

In this, the substituents R and A and B have the following meanings:

$R^2$: H, $C_{1-4}$-alkyl, phenyl and phenyl-$C_{1-4}$-alkyl, $R^{18}O$—$CH_2$—, $R^{18}$—$CO$—, $R^{18}$—$O$—$CH_2$—$CO$—, $R^{18}O$—$CO$—$CO$—, $R^{18}$—$NH$—$CO$—$CO$—, where $R^{18}$ is H or $C_{1-4}$-alkyl, $CF_3$—$CO$— or $C_2F_5$—$CO$—, IIa

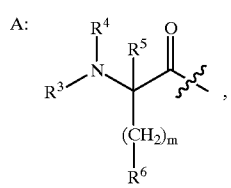

IIb

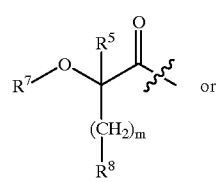 or

IIc

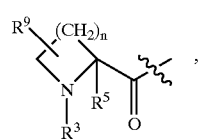

in which the substituents have the following meanings:

m: 0 or 1, n: 2 or 3, $R^3$: H, $C_{1-12}$-alkyl, aryl-$C_{1-4}$-alkyl, $R^{19}OOC$—$C_{1-6}$-alkyl ($R^{19}$ is H, $C_{1-4}$-alkyl, benzyl), $HO_3S$—$C_{1-3}$-alkyl, $C_{1-7}$-alkyl-OOC—, benzyl-OOC—, or $R^{20}R^{21}N$—CO— ($R^{20}$ and $R^{21}$ are identical or different and are H, $C_{1-6}$-alkyl, aryl, aryl-$C_{1-4}$-alkyl, $R^{19}OOC$-$C_{1-4}$-alkyl or $R^{19}$—$NH$—$CO$—$C_{1-4}$-alkyl or $R^{20}$ and $R^{21}$ together are —$(CH_2)_{3-6}$— group, $R^4$: H, $C_{1-12}$-alkyl or aryl-$C_{1-4}$-alkyl, $R^5$: H or $C_{1-4}$-alkyl, $R^6$: $C_{3-8}$-cycloalkyl, where the aliphatic rings can be provided with up to 4 $C_{1-4}$-alkyl and/or $CH_3O$ groups, and one or more methylene groups(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenyl-methyl which can be monosubstituted on one or both rings, dicyclohexylmethyl, phenyl-C)$CH_3)_2$—, $C_{1-4}$-alkyl-C≡C—, $R^{22}O$—$C(R^{23}R^{24})$—, where $R^{22}$ is H or $C_{1-4}$-alkyl, and $R^{23}$ and $R^{24}$ are H, $C_{1-4}$-alkyl, HO—$C_{1-3}$-alkyl or phenyl, phenyl which can be substituted by up to 3 identical or different radicals from the group of $C_{1-4}$-alkyl, $CF_3$, $C_{1-4}$-alkoxy, F or Cl, $R^{25}R^{26}CH$—, where $R^{25}$ is $C_{1-6}$-alkyl, and $R^{26}$ is H or $C_{1-6}$-alkyl, $R^7$: H, $C_{1-12}$-alkyl, $C_{1-20}$-alkyl-CO—, $R^{19}OOC$—$C_{1-4}$-alkyl, $R^{19}OOC$—$C_{1-4}$-alkyl-CO—, $R^{20}R^{21}N$—CO—, $HO_3S$—$C_{1-4}$-alkyl, or the acyl radical of a natural or unnatural bile acid, $R^8$: $C_{3-8}$-cycloalkyl, where the aliphatic rings can be provided with up to 4 $C_{1-4}$-alkyl and/or $CH_3O$ groups, and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenyl-methyl which can be monosubstituted on one or both rings, dicyclohexylmethyl, phenyl-$C(CH_3)_2$—, $C_{1-4}$-alkyl-C≡C—, $R^{22}O$—$C(R^{23}R^{24})$—, where $R^{22}$ is H or $C_{1-4}$-alkyl, and $R^{23}$ and $R^{24}$ are H, $C_{1-4}$-alkyl, HO—$C_{1-3}$-alkyl or phenyl, phenyl which can be substituted by up to 3 identical or different radicals from the group of $C_{1-4}$-alkyl, $CF_3$, $C_{1-4}$-alkoxy, F or Cl, $R^{25}R^{26}CH$—, where $R^{25}$ is $C_{1-6}$-alkyl, and $R^{26}$ is H or $C_{1-6}$-alkyl, $R^9$: H, $C_{1-4}$-alkyl, phenyl or $C_{5-6}$-cycloalkyl ($R^9$ can in accordance with formula IIc be a substituent on all ring positions apart from positions 1 and 2), The structures IIa to IIc are preferably in the D configuration.

B:

IIIa

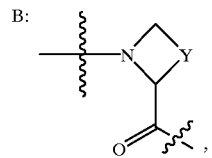

IIIb

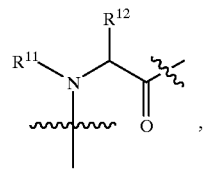

IIIc

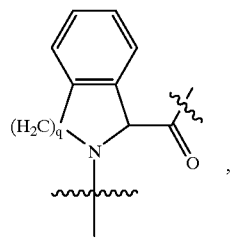

IIId

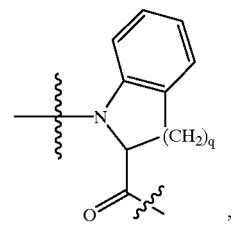

-continued

IIIe

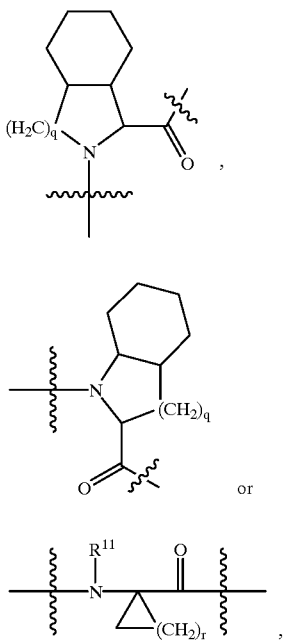

IIIf

IIIg

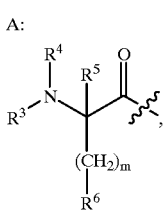

q; 1 or 2 r: 3 or 4

Y: a methylene group,
an ethylene group in which the ring resulting therefrom can carry in position 4 a hydroxyl or $C_{1-4}$-alkoxy group, —CH=CH—, —CH$_2$—S—, —CH$_2$—O— or a propylene group, in which the rings resulting therefrom can carry on the carbon in position 3 and/or 4 a $C_{1-4}$-alkyl group, or in which a —CH$_2$— group can be replaced by —O—, $R^{11}$: H or $C_{3-6}$-cycloalkyl, $R^{12}$: H, $C_{1-6}$-alkyl or $C_{5-6}$-cycloalkyl, $R^{13}$, $R^{14}$ and $R^{15}$, which are identical or different: H, $R^{30}$—O— or $R^{30}$OOC—, where $R^{30}$ is H, $C_{1-6}$-alkyl and $C_{3-6}$-cycloalkyl, and $R^{13}$ and $R^{14}$ can together form the chains —CH$_2$—CH$_2$—CH$_2$—CH$_2$—, —CH$_2$—CH$_2$—CH$_2$—, —O—CH$_2$—O— or —CH=CH—CH=CH—, where $R^{13}$, $R^{14}$ and $R^{15}$ are not all hydrogen.

The structures IIIa to IIIf are preferably in the L configuration.

Particularly preferred compounds Ia are those in which the substituents R and A and B have the following meanings:

$R^2$: H,

A:

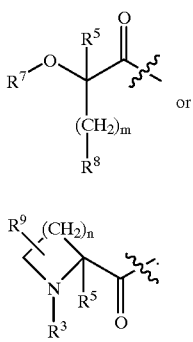

IIa

-continued

IIb

IIc in which the substituents have the following meanings:

m: 0 or 1, n: 2 or 3, $R^3$: H, $C_{1-6}$-alkyl, benzyl, $R^{19}$OOC—$C_{1-6}$-alkyl ($R^{19}$ is H, $C_{1-4}$-alkyl, benzyl), HO$_3$S—$C_{1-3}$-alkyl, or $R^{20}R^{21}$N—CO— ($R^{20}$ and $R^{21}$ are identical or different and are H, $C_{1-6}$-alkyl, or benzyl or $R^{20}$ and $R^{21}$ together are a —(CH$_2$)$_{4-5}$— group), $R^4$: H, $R^5$: H or CH$_3$—, $R^6$: $C_{5-8}$-cycloalkyl—, where the aliphatic rings can be substituted by up to 4 $C_{1-4}$-alkyl and/or CH$_3$O— groups and in which one methylene group can be replaced by —O—, or phenyl which can be substituted by 1 to 3 identical or different radicals from the group of F, Cl, CH$_3$— or CH$_3$O—, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^7$: H, $C_{1-6}$-alkyl-CO— or $R^{19}$OOC—$C_{1-4}$-alkyl, $R^8$: $C_{5-8}$-cycloalkyl—, where the aliphatic rings can be substituted by up to 4 $C_{1-4}$-alkyl and/or CH$_3$O— groups and in which one methylene group can be replaced by —O—, or phenyl which can be substituted by 1 to 3 identical or different radicals from the group of F, Cl, CH$_3$— or CH$_3$O—, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^9$: H, $C_{1-4}$-alkyl, phenyl or $C_{5-6}$-cycloalkyl ($R^9$ can in accordance with formula IIc be a substituent on all ring positions apart from positions 1 and 2).

The structures IIa to IIc are preferably in the D configuration.

B:

IIIa

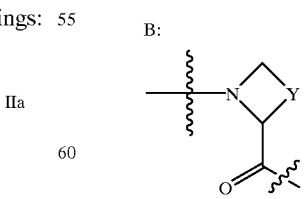

Y: a methylene group, an ethylene group, —CH=CH—, —CH$_2$—S—, —CH$_2$—O— or a propylene group, $R^{13}$: H, HO, CH$_3$O—, EtO—, (CH$_3$)$_2$CH—O—, Cl, Br or I, $R^{14}$: H, HO, $CH_3O$— or Cl,
$R^{15}$: H, HO, $CH_3O$— or Cl,
 where $R^{13}$, $R^{14}$ and $R^{15}$ are not all H.
The structure IIIa is preferably in the L configuration.

Ib:

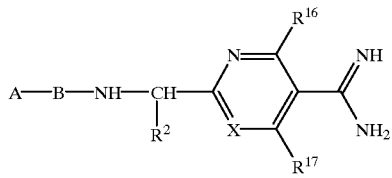

In this, the substituents R, the fragments A and B and X have the following meanings:
$R^2$: H, $C_{1-4}$-alkyl, phenyl, phenyl-$C_{1-4}$-alkyl, $R^{18}O$—$CH_2$—, $R^{18}$—CO—, $R^{18}$—O—$CH_2$—CO—, $R^{18}O$—CO—CO—, $R^{18}$—NH—CO—CO—, where $R^{18}$ is H and $C_{1-4}$-alkyl, or $CF_3$—CO— and $C_2F_5$—CO—,

A:

IIa

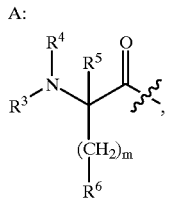

IIb

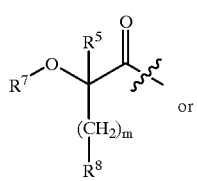

or

IIc

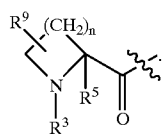

in which the substituents have the following meanings:
m: 0 or 1,
n: 2 or 3,
$R^3$: H, $C_{1-12}$-alkyl, aryl-$C_{1-4}$-alkyl, $R^{19}OOC$—$C_{1-6}$-alkyl ($R^{19}$ is preferably H, $C_{1-4}$-alkyl, benzyl), $HO_3S$—$C_{1-3}$-alkyl, $C_{1-7}$-alkyl-OOC—, benzyl-OOC— or $R^{20}R^{21}N$—CO— ($R^{20}$ and $R^{21}$ are identical or different and are H, $C_{1-6}$-alkyl, aryl, aryl-$C_{1-4}$-alkyl, $R^{19}OOC$—$C_{1-4}$-alkyl, $R^{19}$—NH—CO—$C_{1-4}$-alkyl or $R^{20}$ and $R^{21}$ together are a —$(CH_2)_{3-6}$— group),
$R^4$: H, $C_{1-12}$-alkyl or aryl-$C_{1-4}$-alkyl,
$R^5$: H or $C_{1-4}$-alkyl,
$R^6$: $C_{3-8}$-cycloalkyl, where the aliphatic rings can be provided with up to 4 $C_{1-4}$-alkyl and/or $CH_3O$ groups, and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings,
diphenylmethyl which can be monosubstituted on one or both rings, dicyclohexylmethyl, phenyl-$C(CH_3)_2$—, $C_{1-4}$-alkyl-C≡C—, $R^{22}O$—$C(R^{23}R^{24})$—, in which $R^{22}$ is H or $C_{1-4}$-alkyl, and $R^{23}$ and $R^{24}$ are H, $C_{1-4}$-alkyl, HO—$C_{1-3}$-alkyl or phenyl, phenyl which can be substituted by up to 3 identical or different radicals from the group of $C_{1-4}$-alkyl, $CF_3$, $C_{1-4}$-alkoxy, F— or Cl—, $R^{25}R^{26}CH$—, in which $R^{25}$ is $C_{1-6}$-alkyl, and $R^{26}$ is H or $C_{1-6}$-alkyl, $R^7$: H, $C_{1-12}$-alkyl, $C_{1-20}$-alkyl-CO—, $R^{19}OOC$—$C_{1-4}$-alkyl, $R^{19}OOC$—$C_{1-4}$-alkyl-CO—, $R^{20}R^{21}N$—CO—, $HO_3S$—$C_{1-4}$-alkyl, or the acyl radical of a natural or unnatural bile acid, $R^8$: $C_{3-8}$-cycloalkyl, where the aliphatic rings can be provided with up to 4 $C_{1-4}$-alkyl and/or $CH_3O$ groups, and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl-$C(CH_3)_2$—, $C_{1-4}$-alkyl-C≡C—, $R^{22}O$—$C(R^{23}R^{24})$—, in which $R^{22}$ is H or $C_{1-4}$-alkyl, and $R^{23}$ und $R^{24}$ are H, $C_{1-4}$-alkyl, HO—$C_{1-3}$-alkyl or phenyl, phenyl which can be substituted by up to 3 identical or different radicals from the group of $C_{1-4}$-alkyl, $CF_3$, $C_{1-4}$-alkoxy, F— or Cl—, $R^{25}R^{26}CH$—, in which $R^{25}$ is $C_{1-6}$-alkyl, and $R^{26}$ is H or $C_{1-6}$-alkyl, $R^9$: H, $C_{1-4}$-alkyl, phenyl or $C_{5-6}$-cycloalkyl ($R^9$ can in accordance with formula IIc be a substituent on all ring positions apart from positions 1 and 2), The structures IIa to IIc are preferably in the D configuration.

B:

IIIa

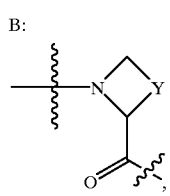

IIIb

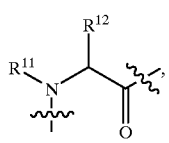

IIIc

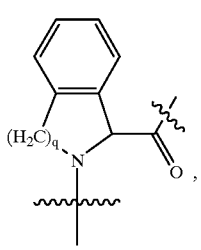

-continued

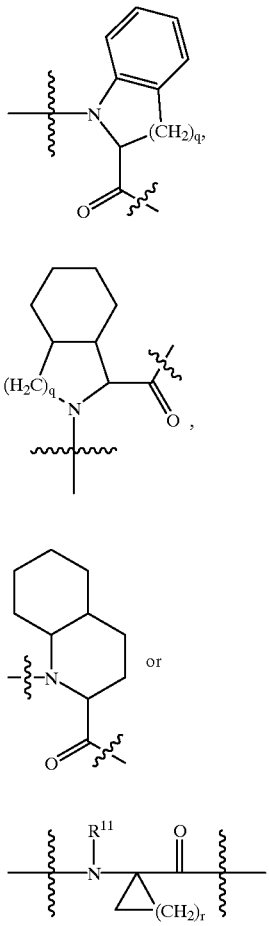

q: 1 or 2 r: 3 or 4

Y a methylene group, an ethylene group in which the ring resulting therefrom can carry in position 4 a hydroxyl or $C_{1-4}$-alkoxy group, —CH=CH—, —CH$_2$—S—, —CH$_2$—O— or a propylene group, in which the rings resulting therefrom can carry on the carbon in position 3 and/or 4 a $C_{1-4}$-alkyl group, or in which a —CH$_2$— group can be replaced by —O—, $R^{11}$: H or $C_{3-6}$-cycloalkyl-, $R^{12}$: H, $C_{1-6}$-alkyl or $C_{5-6}$-cycloalkyl, $R^{16}$: H, F, Cl, $C_{1-4}$-alkyl, $R^{31}$OOC—, in which $R^{31}$ is H or $C_{1-4}$-alkyl, $R^{31}$—O—, $R^{17}$: H, F, Cl, $C_{1-4}$-alkyl, $R^{31}$OOC— or $R^{31}$—O—, where $R^{31}$ is H or $C_{1-4}$-alkyl, X: =CH— or =N—.

The structures IIIa to IIIf are preferably in the L configuration.

Particularly preferred compounds I are those in which the substituents R, the fragments A and B and X have the following meanings:

$R^2$: H,

A:

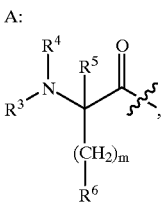

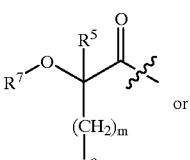

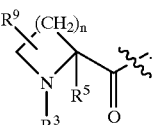

in which the substituents have the following meanings:

m: 0 or 1, n: 2 or 3, $R^3$: H, $C_{1-6}$-alkyl, benzyl, $R^{19}$OOC—$C_{1-6}$-alkyl ($R^{19}$ is H, $C_{1-4}$-alkyl, benzyl), HO$_3$S—$C_{1-3}$-alkyl, or $R^{20}R^{21}$N—CO— ($R^{20}$ and $R^{21}$ are identical or different and are H, $C_{1-6}$-alkyl or benzyl or $R^{20}$ and $R^{21}$ together are a —(CH$_2$)$_{4-5}$— group), $R^4$: H, $R^5$: H or CH$_3$, $R^6$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl which can be substituted by 1 to 3 identical or different radicals from the group of F, Cl, CH$_3$— or CH$_3$O—, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^7$: H, $C_{1-6}$-alkyl-CO— or $R^{19}$OOC—$C_{1-4}$-alkyl, $R^8$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl which can be substituted by 1 to 3 identical or different radicals from the group of F, Cl, CH$_3$— or CH$_3$O—, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^9$: H, $C_{1-4}$-alkyl, phenyl or $C_{5-6}$-cycloalkyl ($R^9$ can in accordance with the formula IIc be a substituent on all ring positions apart from positions 1 and 2).

The structures IIa to IIc are preferably in the D configuration.

B:

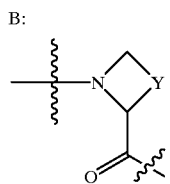

IIIa

Y: a methylene group, an ethylene group —CH=CH—, —CH$_2$—S—, —CH$_2$—O— or a propylene group,
R$^{16}$: H,
R$^{17}$ H—,
X: =CH— or =N—.
The structure IIIa is preferably in the L configuration.

Ic:

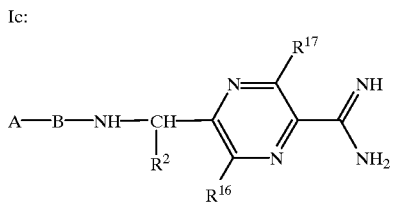

In this, the substituents R and the fragments A and B have the following meanings:

R$^2$: H, C$_{1-4}$-alkyl, phenyl and phenyl-C$_{1-4}$-alkyl, R$^{18}$O—CH$_2$—, R$^{18}$-CO—, R$^{18}$—O—CH$_2$—CO—, R$^{18}$O—CO—CO—, R$^{18}$—NH—CO—CO—, in which R$^{18}$ is H and C$_{1-4}$-alkyl, CF$_3$—CO— or C$_2$F$_5$—CO—,

A:

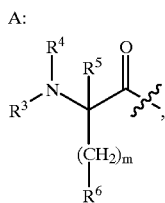

IIa

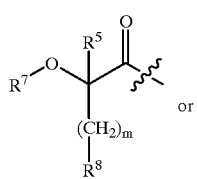

IIb

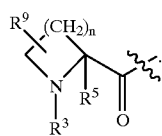

IIc m: 0 or 1,
n: 2 or 3,
R$^3$: H, C$_{1-12}$-alkyl, aryl-C$_{1-4}$-alkyl, R$^{19}$OOC—C$_{1-6}$-alkyl (R$^{19}$ is preferably H, C$_{1-4}$-alkyl, benzyl), HO$_3$S—C$_{1-3}$-alkyl, C$_{1-7}$-alkyl-OOC—, benzyl-OOC—, or R$^{20}$R$^{21}$N—CO— (R$^{20}$ and R$^{21}$ are identical or different and are H, C$_{1-6}$-alkyl, aryl, aryl-C$_{1-4}$-alkyl, R$^{19}$OOC—C$_{1-4}$-alkyl, R$^{19}$—NH—CO—C$_{1-4}$-alkyl or R$^{20}$ and R$^{21}$ together are a —(CH$_2$)$_{3-6}$— group), R$^4$: H, C$_{1-12}$-alkyl or aryl-C$_{1-4}$-alkyl,
R$^5$: H or C$_{1-4}$-alkyl,
R$^6$: C$_{3-8}$-cycloalkyl, where the aliphatic rings can be provided with up to 4 C$_{1-4}$-alkyl and/or CH$_3$O groups, and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl, which can be monosubstituted on one or both rings, dicyclohexylmethyl, phenyl-C(CH$_3$)$_2$—, C$_{1-4}$-alkyl—C≡C—, R$^{22}$O—C(R$^{23}$R$^{24}$)—, in which R$^{22}$ is H or C$_{1-4}$-alkyl, and R$^{23}$ and R$^{24}$ are H, C$_{1-4}$-alkyl, HO—C$_{1-3}$-alkyl or phenyl, phenyl which can be substituted by up to 3 identical or different radicals from the group of C$_{1-4}$-alkyl, CF$_3$, C$_{1-4}$-alkoxy, F or Cl, R$^{25}$R$^{26}$CH—, in which R$^{25}$ is C$_{1-6}$-alkyl, and R$^{26}$ is H or C$_{1-6}$-alkyl, R$^7$: H, C$_{1-12}$-alkyl, C$_{1-20}$-alkyl-CO—, R$^{19}$OOC—C$_{1-4}$-alkyl, R$^{19}$OOC—C$_{1-4}$-alkyl-CO—, R$^{20}$R$^{21}$N—CO—, HO$_3$S—C$_{1-4}$-alkyl-CO—, or the acyl radical of a natural or unnatural bile acid, R$^8$: C$_{3-8}$-cycloalkyl, where the aliphatic rings can be provided with up to 4 C$_{1-4}$-alkyl and/or CH$_3$O groups, and one or more methylene group(s) can be replaced by —O—, —S— or N—C$_{1-4}$-alkyl, or adamantyl, norbornyl, 1-decalinyl, 1-tetralinyl, 2-tetralinyl, 2-indanyl, 2-indanyl, dibenzosuberyl, which can be monosubstituted on one or both aromatic rings, diphenylmethyl, which can be monosubstituted on one or both rings, dicyclohexylmethyl, phenyl-C(CH$_3$)$_2$—, C$_{1-4}$-alkyl-C≡C—, R$^{22}$O—C(R$^{23}$R$^{24}$)—, in which R$^{22}$ is H or C$_{1-4}$-alkyl, and R$^{23}$ and R$^{24}$ are H, C$_{1-4}$-alkyl, HO—C$_{1-3}$-alkyl or phenyl, phenyl which can be substituted by up to 3 identical or different radicals from the group of C$_{1-4}$-alkyl, CF$_3$, C$_{1-4}$-alkoxy, F or Cl, R$^{25}$R$^{26}$CH—, in which R$^{25}$ is C$_{1-6}$-alkyl, and R$^{26}$ is H or C$_{1-6}$-alkyl, R$^9$: H, C$_{1-4}$-alkyl, phenyl or C$_{5-6}$-cycloalkyl (R$^9$ can in accordance with formula IIc be a substituent on all ring positions apart from positions 1 and 2), The structures IIa to IIc are preferably in the D configuration.

B:

IIIa

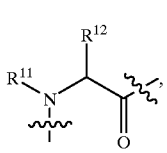

IIIb

-continued

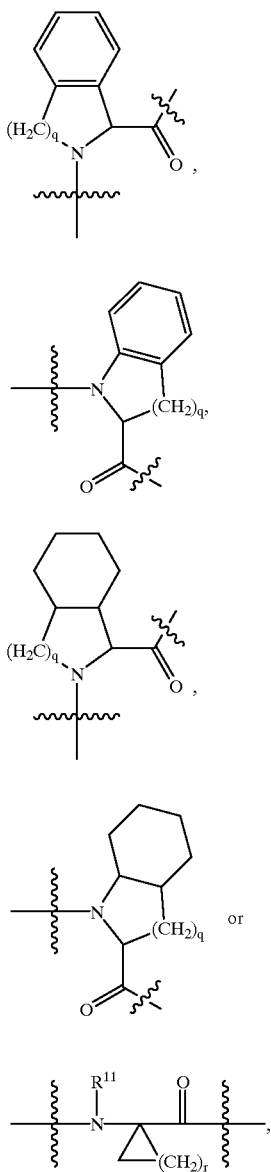

q: 1 or 2 r: 3 or 4

Y a methylene group,
an ethylene group in which the ring resulting therefrom can carry in position 4 a hydroxyl or $C_{1-4}$-alkoxy group, —CH=CH—, —CH$_2$—S—, —CH$_2$—O—, or a propylene group, in which the rings resulting therefrom can carry on the carbon in position 3 and/or 4 a $C_{1-4}$-alkyl group, or in which a —CH$_2$— group can be replaced by —O—, $R^{11}$: H or $C_{3-6}$-cycloalkyl, $R^{12}$: H, $C_{1-6}$-alkyl and $C_{5-6}$-cycloalkyl, $R^{16}$: H, F, Cl, $C_{1-4}$-alkyl, $R^{31}$—OOC—, in which $R^{31}$ is H— or $C_{1-4}$-alkyl, or $R^{31}$—O—, $R^{17}$: H, F, Cl, $C_{1-4}$-alkyl, $R^{31}$—OOC—, $R^{31}$—O—, where $R^{31}$ is H or $C_{1-4}$-alkyl.

The structures IIIa to IIIf are preferably in the L configuration.

Particularly preferred compounds Ic are those in which the substituents R and the fragments A and B have the following meanings:

$R^2$: H—,

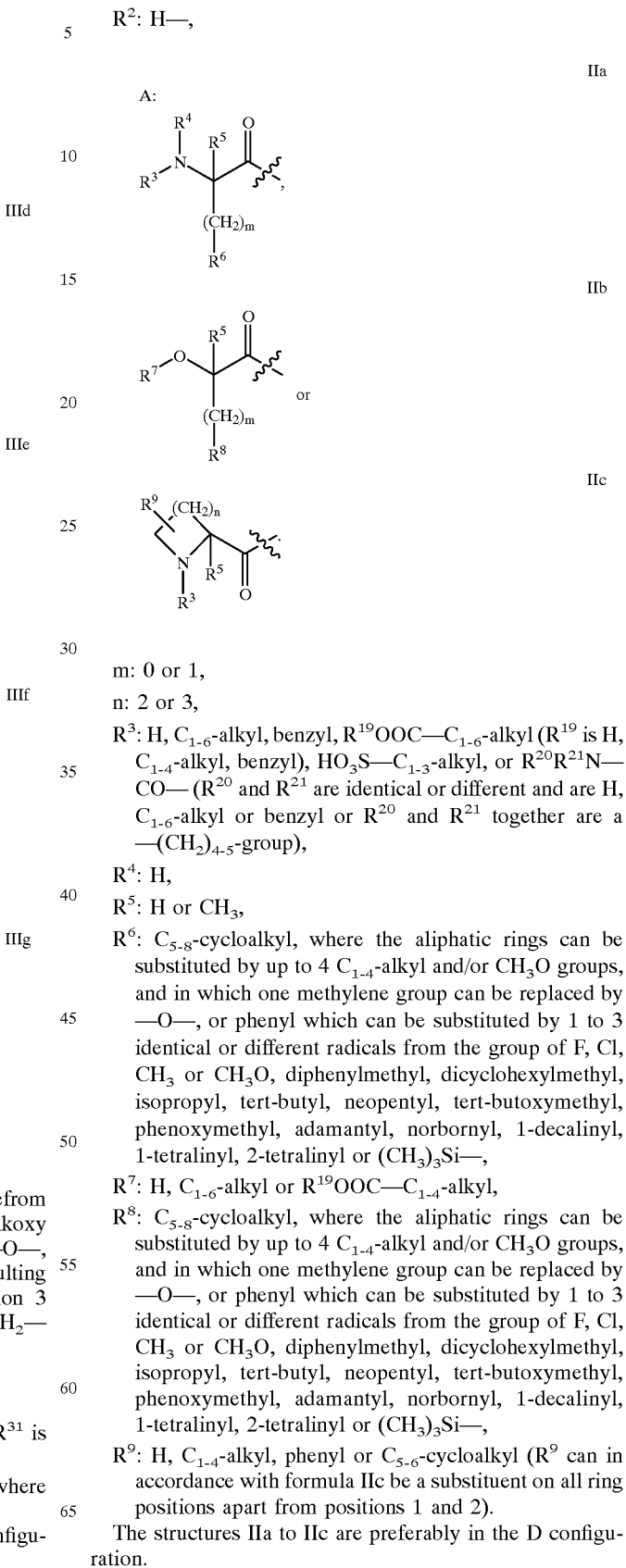

m: 0 or 1, n: 2 or 3, $R^3$: H, $C_{1-6}$-alkyl, benzyl, $R^{19}$OOC—$C_{1-6}$-alkyl ($R^{19}$ is H, $C_{1-4}$-alkyl, benzyl), HO$_3$S—$C_{1-3}$-alkyl, or $R^{20}R^{21}$N—CO— ($R^{20}$ and $R^{21}$ are identical or different and are H, $C_{1-6}$-alkyl or benzyl or $R^{20}$ and $R^{21}$ together are a —(CH$_2$)$_{4-5}$-group), $R^4$: H, $R^5$: H or CH$_3$, $R^6$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^7$: H, $C_{1-6}$-alkyl or $R^{19}$OOC—$C_{1-4}$-alkyl, $R^8$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^9$: H, $C_{1-4}$-alkyl, phenyl or $C_{5-6}$-cycloalkyl ($R^9$ can in accordance with formula IIc be a substituent on all ring positions apart from positions 1 and 2).

The structures IIa to IIc are preferably in the D configuration.

B:

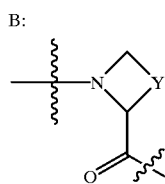

IIIa

Y: a methylene group, an ethylene group, —CH=CH—, —CH$_2$—S—, —CH$_2$—O— or a propylene group,
R$^{16}$: H,
R$^{17}$ H.

The structure IIIa is preferably in the L configuration.

Id:

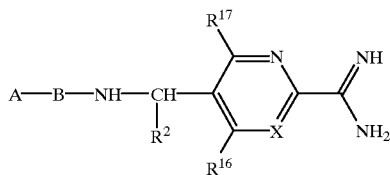

In this, the substituents R, A, B and X have the following meanings:

R$^2$: H, C$_{1-4}$-alkyl, phenyl and phenyl-C$_{1-4}$-alkyl, R$^{18}$O—CH$_2$—, R$^{18}$—CO—, R$^{18}$—O—CH$_2$—CO—, R$^{18}$O—CO—CO—, R$^{18}$—NH—CO—CO—, in which R$^{18}$ is H and C$_{1-4}$-alkyl, or CF$_3$—CO— and C$_2$F$_5$—CO—,

A:

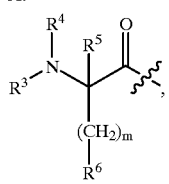

IIa

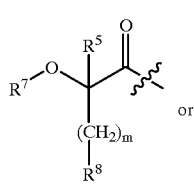

IIb or

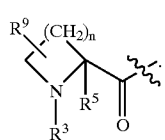

IIc m: 0 or 1,
n: 2 or 3,
R$^3$: H, C$_{1-12}$-alkyl, aryl-C$_{1-4}$-alkyl, R$^{19}$OOC—C$_{1-6}$-alkyl (R$^{19}$ is preferably H, C$_{1-4}$-alkyl, benzyl), HO$_3$S—C$_{1-3}$-alkyl, C$_{1-7}$-alkyl-OOC—, benzyl-OOC—, or R$^{20}$R$^{21}$N—CO— (R$^{20}$ and R$^{21}$ are identical or different and are H, C$_{1-6}$-alkyl, aryl, aryl-C$_{1-4}$-alkyl, R$^{19}$OOC—C$_{1-4}$-alkyl, R$^{19}$—NH—CO—C$_{1-4}$-alkyl or R$^{20}$ and R$^{21}$ together are a —(CH$_2$)$_{3-6}$— group), R$^4$: H, C$_{1-12}$-alkyl or aryl-C$_{1-4}$-alkyl, R$^5$: H or C$_{1-4}$-alkyl, R$^6$: C$_{3-8}$-cycloalkyl, where the aliphatic rings can be provided with up to 4 C$_{1-4}$-alkyl and/or CH$_3$O groups, and one or more methylene group(O) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl-C(CH$_3$)$_2$—, C$_{1-4}$-alkyl-C≡C, R$^{22}$O—C(R$^{23}$R$^{24}$)—, in which R$^{22}$ is H or C$_{1-4}$-alkyl, and R$^{23}$ and R$^{24}$ are H, C$_{1-4}$-alkyl, HO—C$_{1-3}$-alkyl or phenyl, phenyl which can be substituted by up to 3 identical or different radicals from the group of C$_{1-4}$-alkyl, CF$_3$, C$_{1-4}$-alkoxy, F or Cl, R$^{25}$R$^{26}$CH—, in which R$^{25}$ is C$_{1-6}$-alkyl, and R$^{26}$ is H or C$_{1-6}$-alkyl, R$^7$: H, C$_{1-12}$-alkyl, C$_{1-20}$-alkyl-CO—, R$^{19}$OOC—C$_{1-4}$-alkyl, R$^{19}$OOC—C$_{1-4}$-alkyl-CO—, R$^{20}$R$^{21}$N—CO—, HO$_3$S—C$_{1-4}$-alkyl-CO—, or the acyl radical of a natural or unnatural bile acid, R$^8$: C$_{3-8}$-cycloalkyl, where the aliphatic rings can be provided with up to 4 C$_{1-4}$-alkyl and/or CH$_3$O groups, and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl-C(CH$_3$)$_2$—, C$_{1-4}$-alkyl-C≡C—, R$^{22}$O—C(R$^{23}$R$^{24}$)—, in which R$^{22}$ is H or C$_{1-4}$-alkyl, and R$^{23}$ and R$^{24}$ are H, C$_{1-4}$-alkyl, HO—C$_{1-3}$-alkyl or phenyl, R$^9$: H, C$_{1-4}$-alkyl, phenyl or C$_{5-6}$-cycloalkyl (R$^9$ can in accordance with the formula IIc be a substituent on all ring positions apart from positions 1 and 2).

The structures IIa to IIc are preferably in the D configuration.

B:

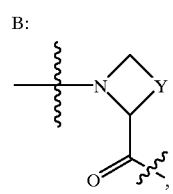

IIIa

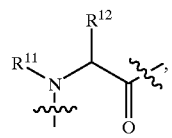

IIIb

-continued

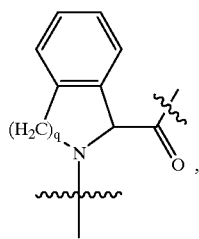

IIIc

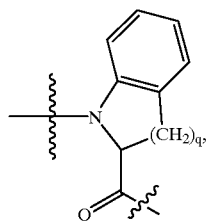

IIId

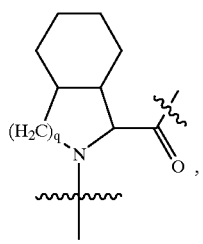

IIIe

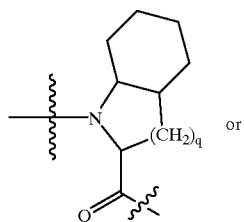  or

IIIf

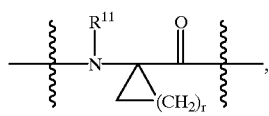

IIIg q: 1 or 2 r: 3 or 4

Y a methylene group,
an ethylene group in which the ring resulting therefrom can carry in position 4 a hydroxyl or $C_{1-4}$-alkoxy group, —CH=CH—, —CH$_2$—S—, —CH$_2$—O— or a propylene group, in which the rings resulting therefrom can carry on the carbon in position 3 and/or 4 a $C_{1-4}$-alkyl group, or in which a CH$_2$ group can be replaced by —O—, $R^{11}$: H or $C_{3-6}$-cycloalkyl, $R^{12}$: H, $C_{1-6}$-alkyl or $C_{5-6}$-cycloalkyl, $R^{16}$: H, F, Cl, $C_{1-4}$-alkyl, $R^{31}$—OOC—, in which $R^{31}$ is H or $C_{1-4}$-alkyl, or $R^{31}$—O—, $R^{17}$: H, F, Cl, $C_{1-4}$-alkyl, $R^{31}$—OOC— or $R^{31}$—O—, where $R^{16}$ and $R^{17}$ are not both H and not both F, and $R^{31}$ is H or $C_{1-4}$-alkyl.

X: =CH— or =N—.

The structures IIIa to IIIf are preferably in the L configuration.

Particularly preferred compound Id are those the substituents R, A, B and X have the following meanings:

$R^2$: H

A:

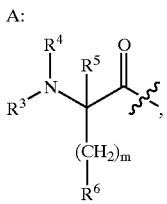

IIa

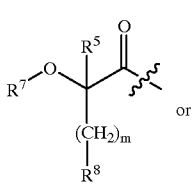  or

IIb

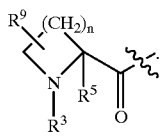

IIc m: 0 or 1, n: 2 or 3, $R^3$: H, $C_{1-6}$-alkyl, benzyl, $R^{19}$OOC—$C_{1-6}$-alkyl ($R^{19}$ is H, $C_{1-4}$-alkyl, benzyl), HO$_3$S—$C_{1-3}$alkyl, or $R^{20}R^{21}$N—CO— ($R^{20}$ and $R^{21}$ are identical or different and are H, $C_{1-6}$-alkyl or benzyl or $R^{20}$ and $R^{21}$ together are a —(CH$_2$)$_{4-5}$— group), $R^4$: H, $R^5$: H or CH$_3$, $R^6$: $C_{5-8}$-cycloalkyl, where the aliphatic rings can be substituted by up to 4 $C_{1-4}$-alkyl and/or CH$_3$O groups and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^7$: H, $C_{1-6}$-alkyl-CO— or $R^{19}$OOC—$C_{1-4}$-alkyl, $R^8$: $C_{5-8}$-cycloalkyl, where the aliphatic rings can be substituted by up to 4 $C_{1-4}$-alkyl and/or CH$_3$O groups and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^9$: H, $C_{1-4}$-alkyl, phenyl or $C_{5-6}$-cycloalkyl ($R^9$ can in accordance with the formula IIc be a substituent on all ring positions apart from positions 1 and 2).

The structures IIa to IIc are preferably in the D configuration.

IIIa

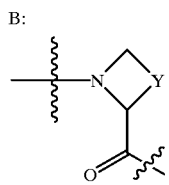

Y: a methylene group, an ethylene group —CH=CH—, —CH$_2$—S—, —CH$_2$—O— or a propylene group, R$^{16}$: H, Cl, C$_{1-4}$-alkyl or CH$_3$O, R$^{17}$: H, Cl, C$_{1-4}$-alkyl or CH$_3$O, where R$^{16}$ and R$^{17}$ are not both H, X: =CH— or =N—.

The structure IIIa is preferably in the L configuration.

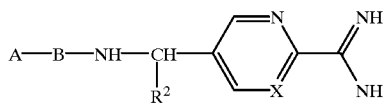

In this, the substituents R, the fragments A and B and X have the following meanings:

a)

R$^2$: H, C$_{1-4}$-alkyl, phenyl, phenyl-C$_{1-4}$-alkyl, R$^{18}$O—CH$_2$—, R$^{18}$—CO—, R$^{18}$—O—CH$_2$—CO—, R$^{18}$O—CO—CO—, R$^{18}$—NH—CO—CO—, in which R$^{18}$ is H or C$_{1-4}$-alkyl, or CF$_3$—CO— or C$_2$F$_5$—CO—, IIa

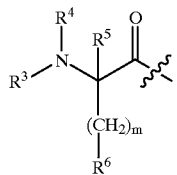

IIb

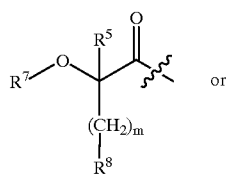 or

IIc

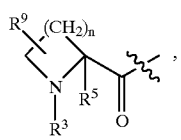, in which the substituents have the following meanings:

m: 0 or 1, n: 2 or 3,

R$^3$: H, C$_{1-12}$-alkyl, aryl-C$_{1-4}$-alkyl, R$^{19}$OOC—C$_{1-6}$-alkyl (R$^{19}$=H, C$_{1-4}$-alkyl, benzyl), HO$_3$S—C$_{1-3}$-alkyl, C$_{1-7}$-alkyl-OOC— or benzyl-OOC—, R$^{20}$R$^{21}$N—CO— (R$^{20}$ and R$^{21}$ are identical or different and are H, C$_{1-6}$-alkyl, aryl, aryl-C$_{1-4}$-alkyl, R$^{19}$OOC—C$_{1-4}$-alkyl and R$^{19}$—NH—CO—C$_{1-4}$-alkyl, or R$^{20}$ and R$^{21}$ together are a —(CH$_2$)$_{3-6}$— group), R$^4$: H, C$_{1-12}$-alkyl or aryl-C$_{1-4}$-alkyl, R$^5$ H or C$_{1-4}$-alkyl, R$^6$: C$_{5-8}$-cycloalkyl, where the aliphatic rings are provided with up to 4 C$_{1-4}$-alkyl and/or CH$_3$O groups and/or one or more CH$_2$ group(s) is(are) replaced by —O—, or phenyl which is substituted by 2 or 3 identical or different radicals from the group of C$_{1-4}$-alkyl, CF$_3$, C$_{1-4}$-alkoxy, F or Cl, adamantyl, norbornyl, 1-decalinyl, 1-tetralinyl, 2-tetralinyl, 1-indanyl, 2-indanyl, diphenylmethyl, dicyclohexylmethyl, dibenzosuberyl, phenyl-C(CH$_3$)$_2$—, C$_{1-4}$-alkyl-C≡C—, Me$_3$Si, or R$^{22}$O—C(R$^{23}$R$^{24}$)—, in which R$^{22}$ is H or C$_{1-4}$-alkyl and R$^{23}$ and R$^{24}$ are H, C$_{1-4}$-alkyl or phenyl, R$^7$: H, C$_{1-12}$-alkyl, C$_{1-20}$-alkyl-CO—, R$^{19}$OOC—C$_{1-4}$-alkyl, R$^{19}$OOC—C$_{1-4}$-alkyl-CO—, R$^{20}$R$^{21}$N—CO—, HO$_3$S—C$_{1-4}$-alkyl-CO—, or the acyl radical of a natural or unnatural bile acid, R$^8$: C$_{5-8}$-cycloalkyl, where the aliphatic rings are provided with up to 4 C$_{1-4}$-alkyl and/or CH$_3$O groups and/or one or more CH$_2$ group(s) is (are) replaced by —O—, or phenyl which is substituted by 2 or 3 identical or different radicals from the group of C$_{1-4}$-alkyl, CF$_3$, C$_{1-4}$-alkoxy, F or Cl, adamantyl, norbornyl, 1-decalinyl, 1-tetralinyl, 2-tetralinyl, 1-indanyl, 2-indanyl, diphenylmethyl, dicyclohexylmethyl, dibenzosuberyl, phenyl-C(CH$_3$)$_2$-13, C$_{1-4}$-alkyl-C≡C—, Me$_3$Si, R$^{22}$O—C(R$^{23}$R$^{24}$)—, R$^9$: C$_{1-4}$-alkyl, phenyl or C$_{5-6}$-cycloalkyl (R$^9$ can in accordance with the formula IIc be a substituent on all ring positions apart from position 1 and 2).

The structures IIa to IIc are preferably in the D configuration.

IIIa

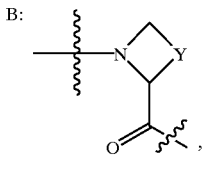,

IIIb

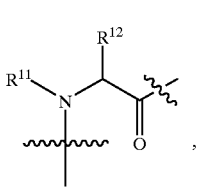,

IIIc

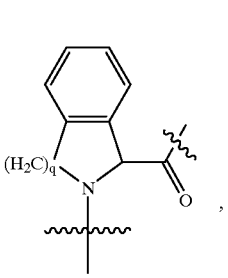

-continued

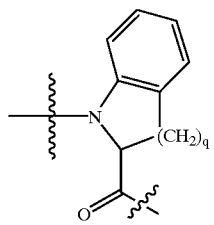
IIId

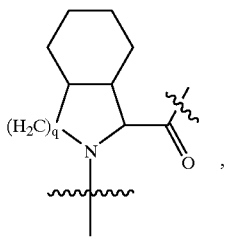
IIIe

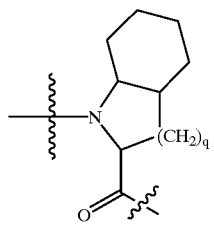
IIIf

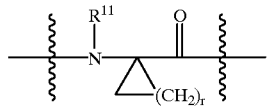
or

IIIg q: 1 or 2 r: 3 or 4

Y a methylene group, an ethylene group in which the ring resulting therefrom can carry in position 4 a hydroxyl or $C_{1-4}$-alkoxy group, —CH=CH—, —CH$_2$—S—, —CH$_2$—O— or a propylene group, in which the rings resulting therefrom can carry on the carbon in position 3 and/or 4 a $C_{1-4}$-alkyl group, or in which one CH$_2$ group can be replaced by —O—, $R^{11}$: H or $C_{3-6}$-cycloalkyl, $R^{12}$: H, $C_{1-6}$-alkyl or $C_{5-6}$-cycloalkyl, X: =CH— or =N—.

The structures IIIa to IIIf are preferably in the L configuration.

Particularly preferred compounds Ie listed under a) are those in which the substituents R, the fragments A and B and X have the following meanings:

$R^2$: H,

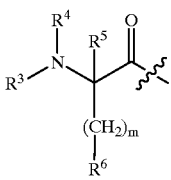
IIa

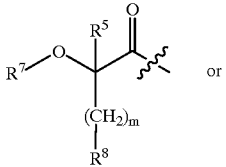
IIb
or

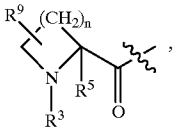
IIc in which the substituents have the following meanings:

m: 0 or 1, n: 2 or 3, $R^3$: H, $C_{1-6}$-alkyl, benzyl, $R^{19}$OOC—$C_{1-6}$-alkyl ($R^{19}$=H, $C_{1-4}$-alkyl, benzyl), HO$_3$S—$C_{1-3}$-alkyl, $R^{20}R^{21}$N—CO— ($R^{20}$ and $R^{21}$ are identical or different and are H, $C_{1-6}$-alkyl or benzyl, or $R^{20}$ and $R^{21}$ together are a —(CH$_2$)$_{4-5}$— group), $R^4$: H, $R^5$ H or CH$_3$, $R^6$: $C_{5-8}$-cycloalkyl, where the aliphatic rings are provided with up to 4 $C_{1-4}$-alkyl and/or CH$_3$O groups, and/or one CH$_2$ group is replaced by —O—, or phenyl which is substituted by 2 or 3 identical or different radicals from the group of CH$_3$, CF$_3$, CH$_3$O, F or Cl, adamantyl, norbornyl, 1-decalinyl, 1-tetralinyl, 2-tetralinyl, diphenylmethyl, dicyclohexylmethyl, Me$_3$Si or tert-butoxymethyl, $R^7$: H, $C_{1-6}$-alkyl—CO— or $R^{19}$OOC-$C_{1-4}$-alkyl, $R^8$: $C_{5-8}$-cycloalkyl, where the aliphatic rings are provided with up to 4 $C_{1-4}$-alkyl and/or CH$_3$O groups, and/or one CH$_2$ group is replaced by —O—, or phenyl which is substituted by 2 or 3 identical or different radicals from the group of CH$_3$, CF$_3$, CH$_3$O, F or Cl, adamantyl, norbornyl, 1-decalinyl, 1-tetralinyl, 2-tetralinyl, diphenylmethyl, dicyclohexylmethyl, Me$_3$Si or tert-butoxymethyl, $R^9$: $C_{1-4}$-alkyl, phenyl or $C_{5-6}$-cycloalkyl ($R^9$ can in accordance with the formula IIc be a substituent on all ring positions apart from positions 1 and 2).

The structures IIa to IIc are preferably in the D configuration.

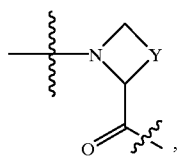
IIIa

Y: a methylene group, an ethylene group, —CH=CH—, —CH₂—S—, —CH₂—O— or a propylene group, X: =CH— or =N—.

The structure IIIa is preferably in the L configuration or in the compound Ie the substituents R, the fragments A and B and X have the following meanings:

b)

$R^2$: H, $C_{1-4}$-alkyl, phenyl, phenyl-$C_{1-4}$-alkyl, $R^{18}O$—$CH_2$—, $R^{18}$—CO—, $R^{18}$—O—$CH_2$—CO—, $R^{18}O$—CO—CO, $R^{18}$—NH—CO—CO—, in which $R^{18}$ is H and $C_{1-4}$-alkyl, or $CF_3$—CO— and $C_2F_5$—CO—,

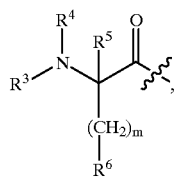
IIa

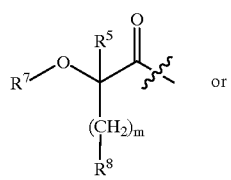
IIb  or

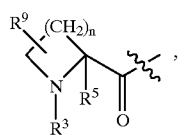
IIc in which the substituents have the following meanings:

m: 0 or 1, n: 2 or 3, $R^3$: H, $C_{1-12}$-alkyl, aryl-$C_{1-4}$-alkyl, $R^{19}OOC$-$C_{1-6}$-alkyl ($R^{19}$ is preferably H, $C_{1-4}$-alkyl, benzyl), $HO_3S$-$C_{1-3}$-alkyl, $C_{1-7}$-alkyl—OOC—, benzyl—OOC—, or $R^{20}R^{21}N$—CO— ($R^{20}$ and $R^{21}$ are identical or different and are H, $C_{1-6}$-alkyl, aryl, aryl-$C_{1-4}$-alkyl, $R^{19}OOC$-$C_{1-4}$-alkyl, $R^{19}$—NH—CO—$C_{1-4}$-alkyl or $R^{20}$ and $R^{21}$ together are a —$(CH_2)_{3-6-}$ group), $R^4$: H, $C_{1-12}$-alkyl or aryl-$C_{1-4}$-alkyl, $R^5$: H or $C_{1-4}$-alkyl, $R^6$: $C_{3-8}$-cycloalkyl which can be substituted by up to 4 $C_{1-4}$-alkyl and/or $CH_3O$ groups and in which one methylene group can be replaced by —O—, or adamantyl, norbornyl, 1-decalinyl, 1-tetralinyl, 2-tetralinyl, 1-indanyl, 2-indanyl, dibenzosuberyl, phenyl-$C(CH_3)_2$—, $C_{1-4}$-alkyl-C=C— or $R^{22}O$-C($R^{23}R^{24}$)—, in which $R^{22}$ is H or $C_{1-4}$-alkyl, and $R^{23}$ and $R^{24}$ are H, $C_{1-4}$-alkyl, HO-$C_{1-3}$-alkyl or phenyl, phenyl which can be substituted by up to 3 identical or different radicals from the group of $C_{1-4}$-alkyl, $CF_3$, $C_{1-4}$-alkoxy, F or Cl, $R^{25}R^{26}CH$—, in which $R^{25}$ is $C_{1-6}$-alkyl, $C_{5-8}$-cycloalkyl or phenyl which can be substituted by 1 to 3 F, Cl, $C_{1-3}$-alkyl, $C_{1-3}$-alkyl—O—, HO or $CF_3$, and $R^{26}$ is H or has one of the meanings stated for $R^{25}$, $R^7$: H, $C_{1-12}$-alkyl, $C_{1-20}$-alkyl—CO—, $R^{19}OOC$—$C_{1-4}$-alkyl, $R^{19}OOC$—$C_{1-4}$-alkyl—CO—, $R^{20}R^{21}N$—CO—, $HO_3S$—$C_{1-4}$-alkyl—CO—, or the acyl radical of a natural or unnatural bile acid, $R^8$: $C_{3-8}$-cycloalkyl, where the aliphatic rings can be provided with up to 4 $C_{1-4}$-alkyl and/or $CH_3O$ groups and one or more methylene group(s) can be replaced by —O—, $R^{25}R^{26}CH$—, in which $R^{25}$ is $C_{1-6}$-alkyl, $C_{6-8}$-cycloalkyl or phenyl which can be substituted by 1 to 3 identical or different radicals from the group of F, Cl, $C_{1-3}$-alkyl, $C_{1-3}$-alkyl—O—, HO or $CF_3$, or $R^{22}O$—$CH_2$—, in which $R^{22}$ has the abovementioned meanings, adamantyl, norbornyl, 1-decalinyl, 1-tetralinyl, 2-tetralinyl, 1-indanyl, 2-indanyl, dibenzosuberyl, which can be monosubstituted on one or both aromatic rings, $R^9$: H, $C_{1-4}$-alkyl, phenyl or $C_{5-6}$-cycloalkyl ($R^9$ can in accordance with the formula IIc be a substituent on all ring positions apart from positions 1 and 2), the structures IIa to IIc are preferably in the D configuration.

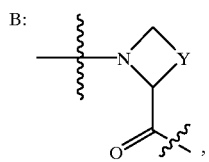
IIIa

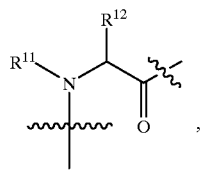
IIIb

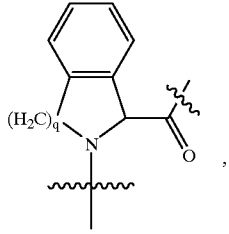
IIIc

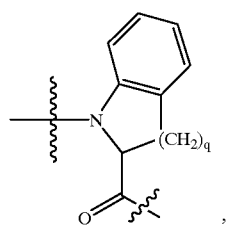
IIId

-continued

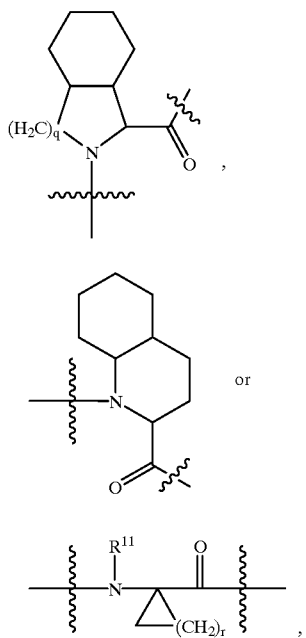
IIIe

IIIf

IIIg $R^{11}$: H or $C_{3-6}$-cycloalkyl $R^{12}$: $C_{1-6}$-alkyl or $C_{5-6}$-cycloalkyl—

Y: —CH=CH—, —CH$_2$—S—, —CH$_2$—O— or a propylene group in which the rings resulting therefrom can carry on the carbon atom in position 3 and/or 4 a $C_{1-4}$-alkyl group, or in which a CH$_2$ group can be replaced by —O—, X: =CH— or =N—.

Particularly preferred compounds Ie are those detailed under b), in which the substituents R and A and B have the following meanings:

$R^2$: H—,

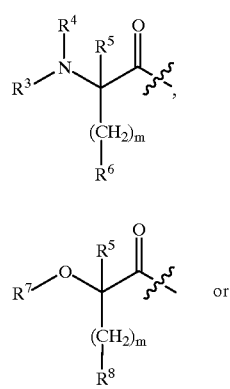
IIa

IIb

IIc in which the substituents have the following meanings:

m: 0 or 1, n: 2 or 3, $R^3$: H, $C_{1-6}$-alkyl, benzyl, $R^{19}$OOC—$C_{1-6}$-alkyl ($R^{19}$ is H, $C_{1-4}$-alkyl, benzyl), HO$_3$S-$C_{1-3}$-alkyl, or $R^{20}R^{21}$N—CO— ($R^{20}$ and $R^{21}$ are identical or different and are H, $C_{1-6}$-alkyl or benzyl or $R^{20}$ and $R^{21}$ together are a —(CH$_2$)$_{4-5}$— group), $R^4$: H, $R^5$: H or CH$_3$, $R^6$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl, which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^7$: H, $C_{1-6}$-alkyl—CO— or $R^{19}$OOC—$C_{1-4}$-alkyl, $R^8$: $C_{5-8}$-cycloalkyl, where the aliphatic rings can be substituted by up to 4 $C_{1-4}$-alkyl and/or CH$_3$O groups, and in which one methylene group can be replaced by —O—, or phenyl, which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, $R^9$: H, $C_{1-4}$-alkyl, phenyl or $C_{5-6}$-cycloalkyl ($R^9$ can in accordance with formula IIc be a substituent on all ring positions apart from positions 1 and 2).

The structures IIa to IIc are preferably in the D configuration.

B:

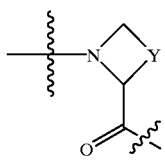
IIIa

Y: —CH=CH—, —CH$_2$—S—, —CH$_2$—O— or a propylene group,

X: =CH— or =N—.

The structure IIIa is preferably in the L configuration.

If:

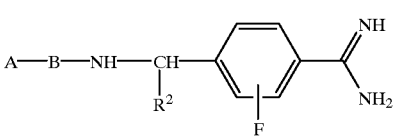

In this, the substituent R and A and B have the following meanings:

a)

$R^2$: H, $C_{1-4}$-alkyl, phenyl, phenyl-$C_{1-4}$-alkyl, $R^{18}$O—CH$_2$—, $R^{18}$—CO—, $R^{18}$—O—CO—, $R^{18}$—O—CH$_2$—CO—, $R^{18}$O—CO—CO—, $R^{18}$—NH—CO—CO—, where $R^{18}$ is H, $C_{1-4}$-alkyl, phenyl-$C_{1-4}$-alkyl or phenyl, or CF$_3$—CO—, C$_2$F$_5$—CO—,

A:

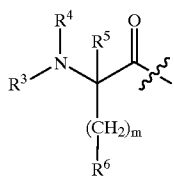
IIa

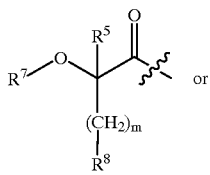   or
IIb

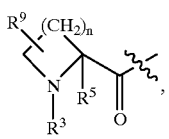
IIc in which the substituents have the following meanings:

m: 0 or 1, n: 2 or 3,

R$^3$: H, C$_{1-12}$-alkyl, aryl-C$_{1-4}$-alkyl, R$^{19}$OOC-C$_{1-6}$-alkyl (R$^{19}$=H, C$_{1-4}$-alkyl, benzyl), HO$_3$S-C$_{1-3}$-alkyl, C$_{1-7}$-alkyl—OOC—, benzyl—OOC—, R$^{20}$R$^{21}$N—CO— (R$^{20}$ and R$^{21}$ are identical or different and are H, C$_{1-6}$-alkyl, aryl, aryl-C$_{1-4}$-alkyl, R$^{19}$OOC-C$_{1-4}$-alkyl or R$^{19}$—NH—CO—C$_{1-4}$-alkyl or R$^{20}$ and R$^{21}$ together are a —(CH$_2$)$_{4-5}$— group), R$^4$: H, C$_{1-12}$-alkyl or aryl-C$_{1-4}$-alkyl, R$^5$ H or C$_{1-4}$-alkyl, R$^6$: C$_{5-8}$-cycloalkyl, where the aliphatic rings are provided with up to 4 C$_{1-4}$-alkyl and/or CH$_3$O groups and/or one or more —CH$_2$group(s) is(are) replaced by —O—, or phenyl which is substituted by 2 or 3 identical or different radicals from the group of C$_{1-4}$-alkyl, CF$_3$, C$_{1-4}$-alkoxy, F or Cl, adamantyl, norbornyl, 1-decalinyl, 1-tetralinyl, 2-tetralinyl, 1-indanyl, 2-indanyl, diphenylmethyl, dicyclohexylmethyl, dibenzosuberyl, phenyl-C(CH$_3$)$_2$—, C$_{1-4}$-alkyl-C≡C—, Me$_3$Si or R$^{22}$O—C(R$^{23}$R$^{24}$)—, in which R$^{22}$ is H or C$_{1-4}$-alkyl, and R$^{23}$ and R$^{24}$ are H, C$_{1-4}$-alkyl or phenyl, R$^7$: H—, C$_{1-12}$-alkyl, C$_{1-20}$-alkyl—CO—, R$^{19}$OOC-C$_{1-4}$-alkyl, R$^{19}$OOC-C$_{1-4}$-alkyl—CO—, R$^{20}$R$^{21}$N—CO—, HO$_3$S-C$_{1-4}$-alkyl—CO—, and the acyl radical of a natural or unnatural bile acid, R$^8$: C$_{5-8}$-cycloalkyl, where the aliphatic rings are provided with up to 4 C$_{1-4}$-alkyl and/or CH$_3$O groups and/or one or more —CH$_2$ group(s) is(are) replaced by —O—, or phenyl which is substituted by 2 or 3 identical or different radicals from the group of C$_{1-4}$-alkyl, CF$_3$, C$_{1-4}$-alkoxy, F or Cl, adamantyl, norbornyl, 1-decalinyl, 1-tetralinyl, 2-tetralinyl, 1-indanyl, 2-indanyl, diphenylmethyl, dicyclohexylmethyl, dibenzosuberyl, phenyl-C(CH$_3$)$_2$—, C$_{1-4}$-alkyl-C≡C—, Me$_3$Si or R$^9$: C$_{1-4}$-alkyl, phenyl or C$_{5-6}$-cycloalkyl (R$^9$ can in accordance with formula IIc be a substituent on all ring positions apart from positions 1 and 2), the structures IIa to IIc are preferably in the D configuration.

B:

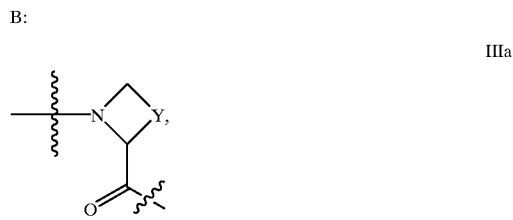
IIIa

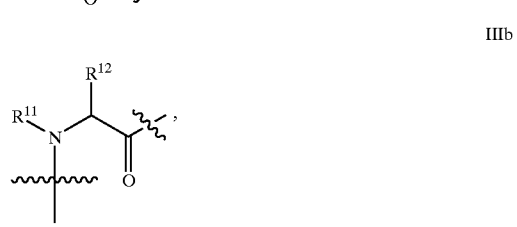
IIIb

IIIc

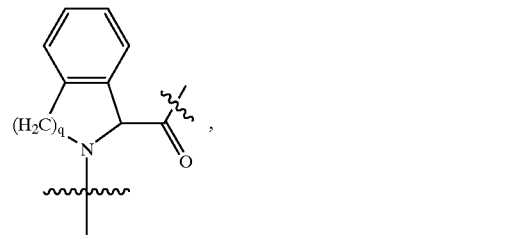
IIId

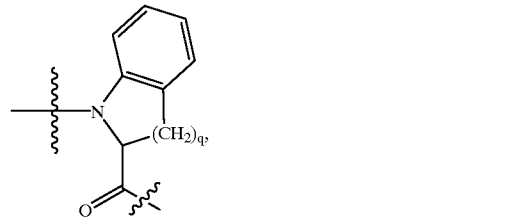
IIIe

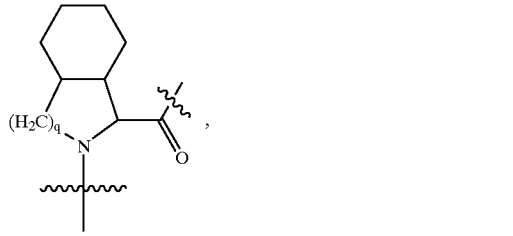
IIIf

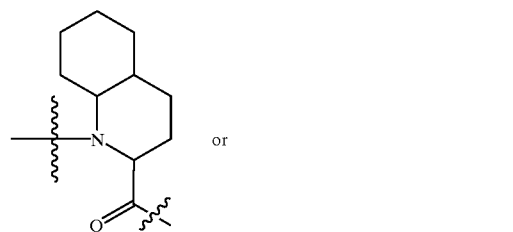   or

IIIg

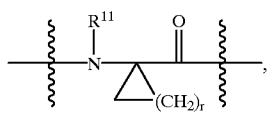

q: 1 or 2 r: 3 or 4

Y a methylene group, an ethylene group in which the ring resulting therefrom can carry in position 4 a hydroxyl or $C_{1-4}$-alkoxy group,
—CH=CH—, —CH$_2$—S—, —CH$_2$—O— or a propylene group, in which the rings resulting therefrom can carry on the carbon atom in position 3 and/or 4 a $C_{1-4}$-alkyl group, or in which one —CH$_2$— group can be replaced by —O—, $R^{11}$: H or $C_{3-6}$-cycloalkyl, $R^{12}$: H, $C_{1-6}$-alkyl or $C_{5-6}$-cycloalkyl.

The structures IIIa to IIIf are preferably in the L configuration.

Particularly preferred compounds If are those listed under a) in which the substituents R and the fragments A and B have the following meanings:

$R^2$: H,

A:

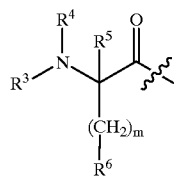

IIa

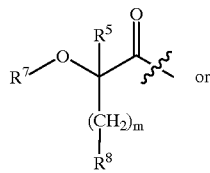

IIb or

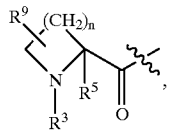

IIc in which the substituents have the following meanings:

m: 0 or 1, n: 2 or 3, $R^3$: H, $C_{1-6}$-alkyl, benzyl, $R^{19}$OOC-$C_{1-6}$-alkyl ($R^{19}$=H, $C_{1-4}$-alkyl, benzyl), HO$_3$S-$C_{1-3}$-alkyl,
$R^{20}R^{21}$N—CO— ($R^{20}$ and $R^{21}$ are identical or different and are H, $C_{1-6}$-alkyl or benzyl, or $R^{20}$ and $R^{21}$ together are a —(CH$_2$)$_{4-5}$- group), $R^4$: H, $R^5$ H or CH$_3$, $R^6$: $C_{5-8}$-cycloalkyl, where the aliphatic rings are provided with up to 4 $C_{1-4}$-alkyl and/or CH$_3$O groups, and/or a CH$_2$ group is replaced by —O—, or phenyl which is substituted by 2 or 3 identical or different radicals from the group of CH$_3$, CF$_3$, CH$_3$O, F or Cl, adamantyl, norbornyl, 1-decalinyl, 1-tetralinyl, 2-tetralinyl, diphenylmethyl, dicyclohexylmethyl, Me$_3$Si- or tert-butoxymethyl, $R^7$: H, $C_{1-6}$-alkyl—CO— or $R^{19}$OOC-$C_{1-4}$-alkyl, $R^8$: $C_{5-8}$-cycloalkyl, where the aliphatic rings are provided with up to 4 $C_{1-4}$-alkyl and/or CH$_3$O groups, and/or a CH$_2$ group is replaced by —O—, or phenyl which is substituted by 2 or 3 identical or different radicals from the group of CH$_3$, CF$_3$, CH$_3$O, F or Cl, adamantyl, norbornyl, 1-decalinyl, 1-tetralinyl, 2-tetralinyl, diphenylmethyl, dicyclohexylmethyl, Me$_3$Si— or tert-butoxymethyl, $R^9$: $C_{1-4}$-alkyl, phenyl or $C_{5-6}$-cycloalkyl ($R^9$ can in accordance with formula IIc be a substituent on all ring positions apart from positions 1 and 2).

The structures IIa to IIc are preferably in the D configuration.

B:

IIIa

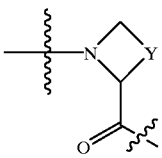

Y: a methylene group, an ethylene group, —CH=CH—, —CH$_2$—S—, —CH$_2$—O— or a propylene group.

The structure IIIa is preferably in the L configuration, in the compound the substituents R and the fragments A and B have the following meanings:

b)

$R^2$: H, $C_{1-4}$-alkyl, phenyl, phenyl-$C_{1-4}$-alkyl, $R^{18}$O—CH$_2$—, $R^{18}$—CO—, $R^{18}$—O—CH$_2$—CO—, $R^{18}$O—CO—CO, $R^{18}$—NH—CO—CO—, in which $R^{18}$ is H and $C_{1-4}$-alkyl, or CF$_3$—CO— and $C_2F_5$—CO—,

A:

IIa

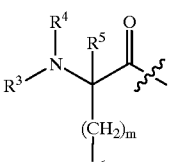

IIb

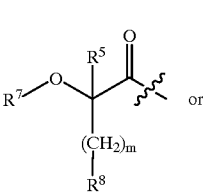

or

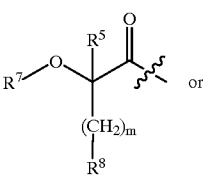

-continued

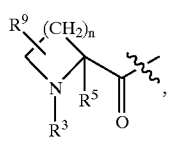
IIc in which the substituents have the following meanings:

m: 0 or 1, n: 2 or 3, $R^3$: H, $C_{1-12}$-alkyl, aryl-$C_{1-4}$-alkyl, $R^{19}$OOC-$C_{1-6}$-alkyl ($R^{19}$ is preferably H, $C_{1-4}$-alkyl, benzyl), $HO_3S$-$C_{1-3}$-alkyl, $C_{1-7}$-alkyl—OCC—, benzyl—OOC—, or $R^{20}R^{21}$N—CO— ($R^{20}$ and $R^{21}$ are identical or different and are H, $C_{1-6}$-alkyl, aryl, aryl-$C_{1-4}$-alkyl, $R^{19}$OOC-$C_{1-4}$-alkyl, $R^{19}$—NH—CO—$C_{1-4}$-alkyl or $R^{20}$ and $R^{21}$ together are a —(CH$_2$)$_{4-5}$— group), $R^4$: H, $C_{1-12}$-alkyl or aryl-$C_{1-4}$-alkyl, $R^5$: H or $C_{1-4}$-alkyl, $R^6$: $C_{3-8}$-cycloalkyl, where the aliphatic rings can be provided with up to 4 $C_{1-4}$-alkyl and/or $CH_3O$ groups and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl—C(CH$_{32}$—, $C_{1-4}$-alkyl—C=C—, $R^{22}$O—C($R^{23}R^{24}$)—, in which $R^{22}$ is H or $C_{1-4}$-alkyl, and $R^{23}$ and $R^{24}$ are H, $C_{1-4}$-alkyl, HO-$C_{1-3}$-alkyl or phenyl phenyl which can be substituted by up to 3 identical or different radicals from the group of $C_{1-4}$-alkyl, $CF_3$, $C_{1-4}$-alkoxy, F or Cl, $R^{25}R^{26}$CH—, in which $R^{25}$ is $C_{1-6}$-alkyl and $R^{26}$ is H or $C_{1-6}$-alkyl, $R^7$: H, $C_{1-12}$-alkyl, $C_{1-20}$-alkyl—CO—, $R^{19}$OOC—$C_{1-4}$-alkyl, $R^{19}$OCC—$C_{1-4}$-alkyl—CO—, $R^{20}R^{21}$N—CO—, $HO_3S$-$C_{1-4}$-alkyl—CO—, or the acyl radical of a natural or unnatural bile acid, $R^8$: $C_{3-8}$-where the aliphatic rings can be provided with up to 4 $C_{1-4}$-alkyl and/or $CH_3O$ groups and one or more methylene group(s) can be replaced by —O—, or adamantyl, norbornyl, 1-decalinyl, 1-tetralinyl, 2-tetralinyl, 1-indanyl, 2-indanyl, dibenzosuberyl, which can be monosubstituted on one or both aromatic rings, diphenylmethyl which can be monosubstituted on one or both rings, dicyclohexylmethyl, phenyl—C(CH$_{32}$—, $C_{1-4}$-alkyl—C=C—, $R^{22}$O—C($R^{23}R^{24}$)—, in which $R^{22}$ is H or $C_{1-4}$-alkyl, and $R^{23}$ and $R^{24}$ are H, $C_{1-4}$-alkyl, HO-$C_{1-3}$-alkyl or phenyl, phenyl which can be substituted by up to 3 identical or different radicals from the group of $C_{1-4}$-alkyl, $CF_3$, $C_{1-4}$-alkoxy, F or Cl, $R^{25}R^{26}$CH—, in which $R^{25}$ is $C_{1-6}$-alkyl and $R^{26}$ is H or $C_{1-6}$-alkyl, $R^9$: H, $C_{1-4}$alkyl, phenyl or $C_{5-6}$-cycloalkyl ($R^9$ can in accordance with formula IIc be a substituent on all ring positions apart from positions 1 and 2).

The structures IIa to IIc are preferably in the D configuration.

B:

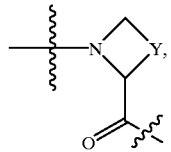
IIIa

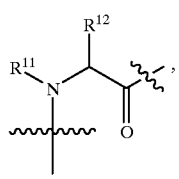
IIIb

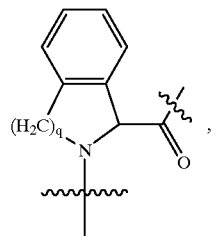
IIIc

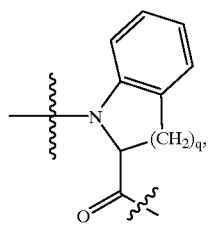
IIId

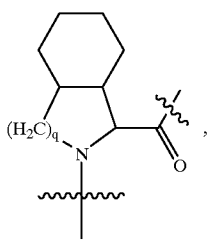
IIIe

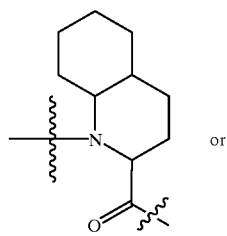
or
IIIf

-continued

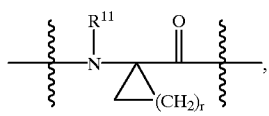
IIIg q: 1 or 2 r: 3 or 4

Y —CH=CH—, —CH$_2$—S—, —CH$_2$—O— or a propylene group, in which the rings resulting therefrom can carry on the carbon in position 3 and/or 4 a C$_{1-4}$-alkyl group, or in which —CH$_2$ group can be replaced by —O—, R$^{11}$: H or C$_{3-6}$- cycloalkyl, R$^{12}$: H, C$_{1-6}$-alkyl or C$_{5-6}$-cycloalkyl, The structures IIIa to IIIf are preferably in the L configuration.

Particularly preferred compounds If listed under b) are those in which the substituents R, the fragments A and B and X have the following meanings:

b)

R$^2$: H,

A:

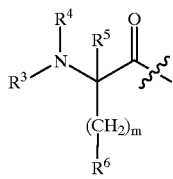
IIa

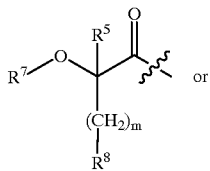
IIb or

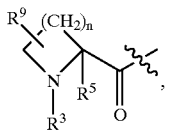
IIc in which the substituents have the following meanings:

m: 0 or 1, n: 2 or 3,

R$^3$: H, C$_{1-6}$-alkyl, benzyl, R$^{19}$OOC-C$_{1-6}$-alkyl (R$^{19}$ is H, C$_{1-4}$-alkyl, benzyl), HO$_3$S-C$_{1-3}$-alkyl, or R$^{20}$R$^{21}$N—CO— (R$^{20}$ and R$^{21}$ are identical or different and are H, C$_{1-6}$-alkyl or benzyl or R$^{20}$ and R$^{21}$ together are a —(CH$_2$)$_{4-5}$— group),

R$^4$: H,

R$^5$: H or CH$_3$,

R$^6$: C$_{5-8}$-cycloalkyl, where the aliphatic rings can be substituted by up to 4 C$_{1-4}$-alkyl and/or CH$_3$O groups and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, R$^7$: H, C$_{1-6}$-alkyl—CO— or R$^{19}$OOC-C$_{1-4}$-alkyl, R$^6$: C$_{5-8}$-cycloalkyl, where the aliphatic rings can be substituted by up to 4 C$_{1-4}$-alkyl and/or CH$_3$O groups and in which one methylene group can be replaced by —O—, or phenyl which can be substituted by 1 to 3 identical or different radicals from the group of F, Cl, CH$_3$ or CH$_3$O, diphenylmethyl, dicyclohexylmethyl, isopropyl, tert-butyl, neopentyl, tert-butoxymethyl, phenoxymethyl, adamantyl, norbornyl, 1-decalinyl, 1-tetralinyl, 2-tetralinyl or (CH$_3$)$_3$Si—, R$^9$: H, C$_{1-4}$-alkyl, phenyl or C$_{5-6}$-cycloalkyl (R$^9$ can in accordance with formula IIc be a substituent on all ring positions apart from positions 1 and 2).

The structures IIa to IIc are preferably in the D configuration.

B:

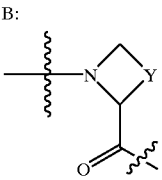
IIIa

Y: —CH=CH—, —CH$_2$—S—, —CH$_2$—O— or a propylene group.

The structure IIIa is preferably in the L configuration.

Ig:

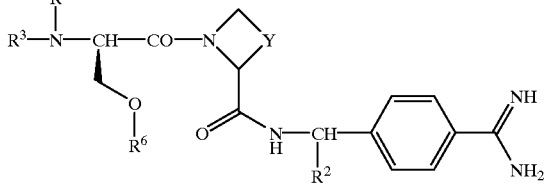

In this, the substituents R and the function of Y have the followed meanings:

a)

R$^2$: H, C$_{1-4}$-alkyl, phenyl, phenyl-C$_{1-4}$-alkyl, R$^{18}$O—CH$_2$—, R$^{18}$—CO—, R$^{18}$—O—CH$_2$—CO—, R$^{18}$—NH—CO—CO—, where R$^{18}$ is H or C$_{1-4}$-alkyl, or CF$_3$—CO— or C$_2$F$_5$—CO—, R$^3$: R$^{19}$OOC-C$_{1-4}$-alkyl (R$^{19}$=H—, C$_{1-4}$-alkyl, benzyl), HO$_3$S-C$_{1-3}$-alkyl, or R$^{20}$R$^{21}$N—CO— (R$^{20}$ and R$^{21}$ are identical or different and are H, C$_{1-6}$-alkyl, aryl, aryl-C$_{1-2}$-alkyl, or R$^{20}$ and R$^{21}$ together are a —(CH$_2$)$_{4-5}$— group), R$^4$: H, C$_{1-12}$-alkyl or aryl-C$_{1-2}$-alkyl, R$^6$: H, C$_{1-12}$-alkyl and Y: —CH$_2$—, —CH$_2$—CH$_2$— or —CH$_2$—CH$_2$—CH$_2$—.

The amino acid containing Y is preferably in the L configuration.

Particularly preferred compounds Ig listed under a) are those in which the substituents R and the function of Y have the following meanings:

a) $R^2$: H, $R^3$: $R^{19}$OOC-$C_{1-4}$-alkyl ($R^{19}$=H—, $C_{1-4}$-alkyl, benzyl), HO$_3$S-$C_{1-3}$-alkyl, or $R^{20}R^{21}$N—CO— ($R^{20}$ and $R^{21}$ are identical or different and are H, $C_{1-6}$-alkyl, or benzyl, or $R^{20}$ and $R^{21}$ together are a —(CH$_2$)$_{4-5}$— group), $R^4$: H, $R^6$: H, $C_{1-4}$-alkyl and Y: —CH$_2$—, —CH$_2$—CH$_2$— or —CH$_2$—CH$_2$—CH$_2$—.

The amino acid containing Y is preferably in the configuration.

or in the compound Ig, the substituents R and Y have the following meanings:

b)

$R^2$: H, $C_{1-4}$-alkyl, phenyl, phenyl-$C_{1-4}$-alkyl, $R^{18}$O—CH$_2$—, $R^{18}$—CO—, $R^{18}$—O—CH$_2$—CO—, $R^{18}$NH—CO—CO—, where $R^{18}$ is H or $C_{1-4}$-alkyl, or CF$_3$—CO— or C$_2$F$_5$—CO—, $R^3$: H, $C_{1-12}$-alkyl, aryl-$C_{1-2}$-alkyl, $R^{19}$OOC-$C_{1-4}$-alkyl ($R^{19}$=H, $C_{1-4}$-alkyl, benzyl), HO$_3$S-$C_{1-3}$-alkyl, $C_{1-4}$-alkyl-OOC—, benzyl—OOC— or $R^{20}R^{21}$N—CO— ($R^{20}$ and $R^{21}$ are identical or different and are H, $C_{1-6}$-alkyl, aryl, aryl-$C_{1-2}$-alkyl, or $R^{20}$ and $R^{21}$ together are a —(CH$_2$)$_{4-5}$— group), $R^4$: H, $C_{1-12}$-alkyl and Y: an ethylene group in which the ring resulting therefrom carries in position 4 a hydroxyl or $C_{1-4}$-alkoxy group, or —CH$_2$—S—, —CH$_2$—O—, —CH=CH— or a propylene group in which one CH$_2$ group is replaced by —O— or —S—.

The amino acid containing Y is preferably in the L configuration.

Particularly preferred compounds Ig listed under b) are those in which the substituents R and the function of Y have the following meanings:

$R^2$: H, $R^3$: H, $C_{1-6}$-alkyl, benzyl, $R^{19}$OCC-$C_{1-4}$-alkyl ($R^{19}$=H, $C_{1-4}$-alkyl, benzyl), HO$_3$S-$C_{1-3}$-alkyl, or $R^{20}R^{21}$N—CO— ($R^{20}$ and $R^{21}$ are identical or different and are H, $C_{1-6}$-alkyl, aryl or benzyl, or $R^{20}$ and $R^{21}$ together are a —(CH$_2$)$_{4-5}$— group), $R^4$: H, $C_{1-12}$-alkyl or aryl-$C_{1-2}$-alkyl, $R^6$: H, $C_{1-4}$-alkyl and Y: —CH$_2$—s—, —CH$_2$—O— or —CH=CH—.

The amino acid containing Y is preferably in the L configuration.

Ih:

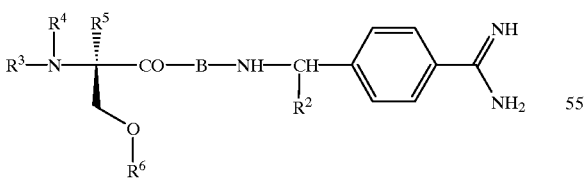

In this, the substituents R and B have the following meanings:

$R^2$: H, $C_{1-4}$-alkyl, phenyl, phenyl-$C_{1-4}$-alkyl, $R^{18}$O—CH$_2$—, $R^{18}$—CO—, $R^{18}$—O—CH$_2$—CO—, $R^{18}$—NH—CO—CO—, where $R^{18}$ is H or $C_{1-4}$-alkyl, or CF$_3$—CO— or C$_2$F$_5$—CO—, $R^3$: H, $C_{1-12}$-alkyl, aryl-$C_{1-2}$-alkyl, $R^{19}$OOC—$C_{1-4}$-alkyl ($R^{19}$=H, $C_{1-4}$-alkyl, benzyl), HO$_3$S—$C_{1-3}$-alkyl, $C_{1-4}$-alkyl-OOC—, benzyl-OOC— or $R^{20}R^{21}$N—CO— ($R^{20}$ and $R^{21}$ are identical or different and are H, $C_{1-6}$-alkyl, aryl, aryl-$C_{1-2}$-alkyl, or $R^{20}$ and $R^{21}$ together are a —(CH$_2$)$_{4-5}$— group), $R^4$: H, $C_{1-12}$-alkyl or aryl-$C_{1-2}$-alkyl, $R^5$: $C_{1-4}$-alkyl, $R^6$: H, $C_{1-12}$-alkyl.

B:

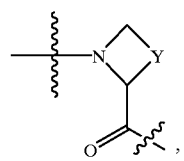
IIIa

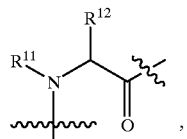
IIIb

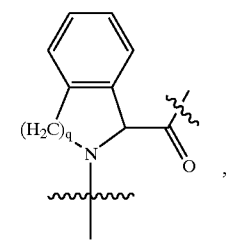
IIIc

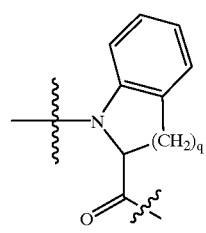
IIId

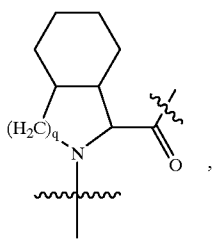
IIIe

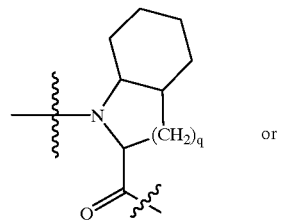
IIIf or

-continued

IIIg

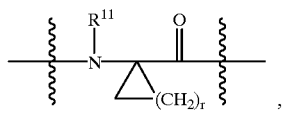

q: 1 or 2
r: 3 or 4
$R^{11}$: H or $C_{3-6}$-cycloalkyl,
$R^{12}$: H, $C_{1-6}$-alkyl or $C_{5-6}$-cycloalkyl,
Y: a methylene group,
 an ethylene group in which the ring resulting therefrom can carry in position 4 a hydroxyl or $C_{1-4}$-alkoxy group. —$CH_2$—S—, —$CH_2$—O—, —CH=CH— or a propylene group in which one —$CH_2$— group can be replaced by —O— or —S—.
The structures IIIa to IIIf are preferably in the L configuration.

Particularly preferred compounds Ia are those in which the substituents R and B have the following meanings:
$R^2$: H,
$R^3$: H, $C_{1-6}$-alkyl, benzyl, $R^{19}$OOC—$C_{1-4}$-alkyl ($R^{19}$=H, $C_{1-4}$-alkyl, benzyl), $HO_3S$—$C_{1-3}$-alkyl, or $R^{20}R^{21}N$—CO— ($R^{20}$ and $R^{21}$ are identical or different and are H, $C_{1-6}$-alkyl or benzyl, or $R^{20}$ and $R^{21}$ together are a —$(CH_2)_{4-5}$— group),
$R^4$: H,
$R^5$: $CH_3$,
$R^6$: H, $C_{1-4}$-alkyl.

B:
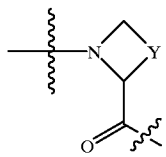
IIIa

Y: a methylene group, an ethylene group,
 —$CH_2$—S—, —$CH_2$—O—, —CH=CH— or a propylene group.
The structure IIIa is preferably in the L configuration.

Ii:
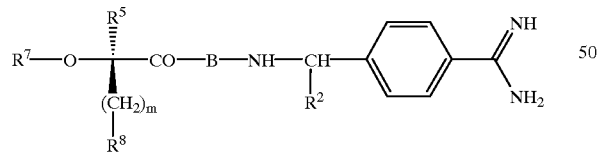

In this, the substituents R, the fragment B and m have the following meanings:
m: 0, 1
$R^2$: H, $C_{1-4}$-alkyl, phenyl, phenyl-$C_{1-4}$-alkyl, $R^{18}$O—$CH_2$—, $R^{18}$—CO—, $R^{18}$—O—$CH_2$—CO—, $R^{18}$—NH—CO—CO—, where $R^{18}$ is H or $C_{1-4}$-alkyl, or $CF_3$—CO— or $C_2F_5$—CO—,
$R^5$: H or $C_{1-4}$-alkyl,
$R^7$: H, $C_{1-12}$-alkyl, $C_{1-20}$-alkyl-CO—, $R^{19}$OOC—$C_{1-4}$-alkyl ($R^{19}$=H, $C_{1-4}$-alkyl, benzyl), $R^{19}$OOC—$C_{1-4}$-alkyl-CO—, $R^{20}R^{21}N$—CO—, $HO_3S$—$C_{1-4}$-alkyl, and the acyl radical of a natural or unnatural bile acid ($R^{20}$, $R^{21}$ are identical or different and are H, $C_{1-6}$-alkyl or benzyl, or $R^{20}$ and $R^{21}$ together are a —$(CH_2)_{4-5}$— group), $R^8$: $C_{3-8}$-cycloalkyl, where the aliphatic rings are provided with up to 4 $C_{1-4}$-alkyl and/or $CH_3O$ groups, and/or one or more methylene group(s) is (are) replaced by —O—, or phenyl which is substituted by 2 or 3 identical or different radicals from the group of $C_{1-4}$-alkyl, $CF_3$, $C_{1-4}$-alkoxy, F or Cl, adamantyl, norbornyl, 1-decalinyl, 1-tetralinyl, 2-tetralinyl, 1-indanyl, 2-indanyl, $(CH_3)_3Si$—, diphenylmethyl, dicyclohexylmethyl or dibenzosuberyl, which can be monosubstituted on one or both aromatic rings,

B:

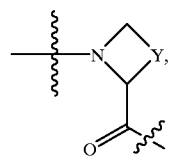
IIIa

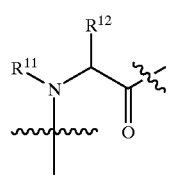
IIIb

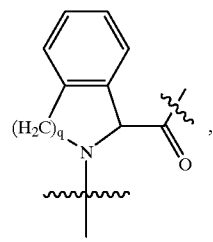
IIIc

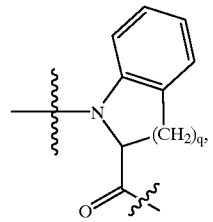
IIId

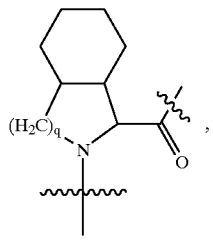
IIIe

-continued

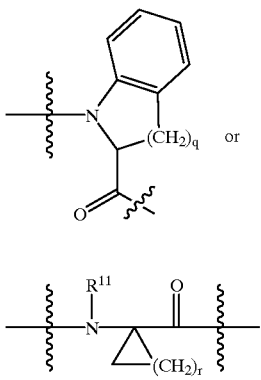

IIIf

IIIg q: 1 or 2
r: 3 or 4
Y: a methylene group,
  an ethylene group in which the ring resulting therefrom can carry in position 4 a hydroxyl or $C_{1-4}$-alkoxy group, —$CH_2$—S—, —$CH_2$—O—, —CH═CH— or a propylene group in which one —$CH_2$ group can be replaced by —O— or —S—.
$R^{11}$: H or $C_{3-6}$-cycloalkyl
$R^{12}$: H, $C_{1-6}$-alkyl, $C_{5-6}$-cycloalkyl.
The structures IIIa or IIIf are preferably in the L configuration.

Particularly preferred compounds Ii are those in which the substituents R and the fragment B have the following meanings:
$R^2$: H,
$R^5$: H or $CH_3$,
$R^7$: H, $C_{1-6}$-alkyl-CO—, $R^{19}$OOC—$C_{1-4}$-alkyl, ($R^{19}$=H, $C_{1-4}$-alkyl, benzyl)
$R^8$: $C_{5-8}$-cycloalkyl, where the aliphatic rings are substituted by up to 4 $CH_3$ and/or $CH_3O$ groups, and/or one methylene group is replaced by —O—, or phenyl, which is substituted by 2 or 3 identical or different radicals from the group of $CH_3$, $CF_3$, $CH_3O$, F or Cl, adamantyl, norbornyl, 1-decalinyl, 1-tetralinyl, 2-tetralinyl, diphenylmethyl, dicyclohexylmethyl, $Me_3Si$ or tert-butoxymethyl,

B:

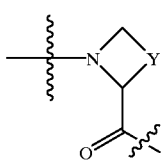

IIIa

Y: a methylene group, an ethylene group,
  —$CH_2$—S—, —$CH_2$—O—, —CH═CH— or a propylene group.
The structure IIIa is preferably in the L configuration.

The term "alkyl" used above describes straight-chain and branched carbon frameworks. Aryl means carbo- and heterocyclic aromatic systems which can be mono- or bicyclic.

Preferred structures of the invention are:
(D)-(Cyclohexyl)Hyac-Pro-NH-3-(6-am)-pico
(D)-(Cyclohexyl)Hyac-Pro-NH-4-amb
(D)-(Cyclohexyl)Hyac-Pro-NH-(2-MeO)-4-amb
(D)-(Cyclohexyl)Hyac-Aze-NH-4-amb
(D)-(3-Phenyl)Hyac-Pro-NH-4-amb
(D,L)-(1-Tetralinyl)Hyac-Pro-NH-3-(6-am)-pico
(D,L)-(1-Tetralinyl)Hyac-Pro-NH-4-amb
O-Acetyl-(D)-(Cyclohexyl)Hyac-Pro-NH-3-(6-am)-pico
O-Acetyl-(D)-(Cyclohexyl)Hyac-Pro-NH-4-amb
O-Hexanoyl-(D)-(Cyclohexyl)Hyac-Pro-NH-4-amb
O-Hydroxycarbonyl-methyl-(D)-(Cyclohexyl)Hyac-Pro-NH-3-(6-am)-pico
(D)-(β-Cyclohexyl)Hypr-Pro-NH-3-(6-am)-pico
(D)-(β-Cyclohexyl)Hypr-Pro-NH-4-amb
(D)-(β-Cyclohexyl)Hypr-Pro-NH-(2-MeO)-4-amb
(D,L)-(β,β-Diphenyl)Hypr-Pro-NH-3-(6-am)-pico
(D,L)-(β,β-Diphenyl)Hypr-Pro-NH-4-amb
(D,L)-(β,β-Dicyclohexyl)Hypr-Pro-NH-3-(6-am)-pico
H-(D)-Chg-Aze-NH-3-(6-am)-pico
H-(D)-Chg-Pic-NH-3-(6-am)-pico
H-(D)-Cha-Pro-NH-3-(6-am)-pico
H-(D)-(tert.Butyl)Ser-Pro-NH-3-(6-am)-pico
H-(D)-Chg-Hyp-NH-3-(6-am)-pico
H-(D)-Chg-1-Tic-NH-3-(6-am)-pico
H-(D)-Chg-3-Tic-NH-3-(6-am)-pico
H-(D)-Chg-2-Phi-NH-3-(6-am)-pico
H-(D,L)-Chea-Pro-NH-3-(6-am)-pico
H-(D)-(α-Me)Cha-Pro-NH-3-(6-am)-pico
H-D,L-4-Tetrahydropyranyl)-Gly-Pro-NH-3-(6-am)-pico
H-(±)-(threo)-(β-Hydroxy)-Phe-Pro-NH-3-(6-am)-pico
H-(D,L)-(2-Norbornyl)Gly-Pro-NH-3-(6-am)-pico
H-(D,L)-(1-Adamantyl)Gly-Pro-NH-3-(6-am)-pico
H-(D,L)-(1-Tetralinyl)Gly-Pro-NH-3-(6-am)-pico
H-(D,L)-($Me_3$Si)Ala-Pro-NH-3-(6-am)-pico
H-(D,L)-(3,4,5-Trimethoxy)Phe-Pro-NH-3-(6-am)-pico
H-(D,L)-(3-Phenyl)Pro-Pro-NH-3-(6-am)-pico
H-(D,L)-(4-Me)Pic-Pro-NH-3-(6-am)-pico
H-(D)-Cha-Pyr-NH-3-(6-am)-pico
H-(D)-Chg-(N-Cyclopropyl)Gly-NH-3-(6-am)-pico
H-(D)-Chg-(Cyclo)Leu-NH-3-(6-am)-pico
H-(D)-Chg-Pro-NH-5-(2-am)-pym
H-(D)-Chg-Pro-NH-2-(5-am)-pym
H-(D)-Chg-Pro-NH-(4-am)-napme
H-(D,L)-Thpg-Pro-NH-(2-MeO)-4-amb
H-(D,L)-Dpa-Pro-NH-(2-MeO)-4-amb
H-(D,L)-(2-Norbornyl)Gly-Pro-NH-(2-MeO)-4-amb
H-(D,L)-(1-Tetralinyl)Gly-Pro-NH-(2-MeO)-4-amb
H-(D,L)-Cog-Pro-NH-(2-MeO)-4-amb
H-(D)-(α-Me)Cha-Pro-NH-(2-MeO)-4-amb
H-(D,L)-(Debenzosuberyl)Gly-Pro-NH-(2-MeO)-4-amb
H-(D,L)-(3,4,5-Trimethoxy)Phe-Pro-NH-(2-MeO)-4-amb
H-(D,L)-($Me_3$Si)Ala-Pro-NH-(2-MeO)-4-amb
H-(±threo)-(3-Hydroxy)Phe-Pro-NH-(2-MeO)-4-amb
H-(D)-(tert-Butyl)Ser-Pro-NH-(2-MeO)-4-amb
H-(D,L)-(3-Phenyl)Pro-Pro-NH-(2-MeO)-4-amb
H-(D)-Chg-Pic-NH-(2-MeO)-4-amb
H-(D)-Chg-Pyr-NH-(2-MeO)-4-amb
H-(D)-Chg-(N-cyclopropyl)Gly-NH-(2-MeO)-4-amb
H-(D)-Chg-1-Tic-NH-(2-MeO)-4-amb
H-(D)-Cha-Pic-NH-(2-MeO)-4-amb
H-(D)-Chg-Pro-NH-(2-EtO)-4-amb
H-(D)-Chg-Pro-NH-(2-I)-4-amb
H-(D)-Chg-(Cyclo)Leu-NH-(2-MeO)-4-amb
H-(D)-Chg-Pro-NH-(2-OH)-4-amb
H-(D)-Chg-Pro-NH-(2,6-Dimethoxy)-4-amb
H-(D)-Chg-Pro-NH-(3-MeO)-4-amb
H-(D)-Chg-Pro-NH-(3-OH)-4-amb
H-(D)-Chg-Pro-NH-(3-Cl)-4-amb
H-(D)-Chg-Pro-NH-(2-COOH)-4-amb
H-(D)-Chg-Pro-NH-(2-$NH_2$)-4-amb H-(D)-Chg-Pro-NH-(2-OCH$_2$-COOH)-4-amb
HOOC-CH$_2$-(D)-Cha-Pro-NH-(2-MeO)-4-amb
MeOOC-Ch$_2$-(D)-Cha-Pro-NH-(2-MeO)-4-amb
HOOC-CH$_2$-CH$_2$-(D)-Chg-Pro-NH-(2-MeO)-4-amb
tBuOOC-CH$_2$-(D,L)-Cog-Pro-NH-(2-MeO)-4-amb
HOOC-CH$_2$-(D,L)-Cog-Pro-NH-(2-MeO)-4-amb
HOOC-CH$_2$-(D,L)-Dpa-Pro-NH-(2-MeO)-4-amb
Cbz-(D)-(tert-Butyl)Ser-Pro-NH-(2-MeO)-4-amb
HOOC-CH$_2$-(D)-Cha-Pic-NH-(2-MeO)-4-amb
Ph-CH$_2$-(D)-Chg-Pro-NH-(2-MeO)-4-amb
HOOC-CH$_2$-(D)-Chg-Pro-NH-(2-OH)-4-amb
HOOC-CH$_2$-(D)-Cha-Pro-NH-(2-OH)-4-amb
HOOC-CH$_2$-(D)-Chg-Pro-NH-(2-Cl)-4-amb
HOOC-CH$_2$-(D,L)-(4-Me)Chg-Pro-NH-3-(6-am)-pico
HOOC-CH$_2$-(D,L)-(4-iPr)Chg-Pro-NH-3-(6-am)-pico
HOOC-CH$_2$-(D,L)-(4-tBu)Chg-Pro-NH-3-(6-am)-pico
HOOC-CH$_2$-(D,L)-Dch-Pro-NH-3-(6-am)-pico
HOOC-CH$_2$-(D,L)-(3,3-Dimethyl)Chg-Pro-NH-3-(6-am)-pico
HOOC-CH$_2$-(D)-(tert-Butyl)Ser-Pro-NH-3-(6-am)-pico
HOOC-CH$_2$-(D,L)-Cpg-Pro-NH-3-(6-am)-pico
HOOC-CH$_2$-(D,L)-(1-Tetralinyl)Gly-Pro-NH-3-(6-am)-pico
HOOC-CH$_2$-(D,L)-(2-norbornyl)Gly-Pro-NH-3-(6-am)-pico
HOOC-CH$_2$-(D,L)-(Thpg)-Pro-NH-3-(6-am)-pico
HOOC-CH$_2$-(D,L)-(Thpa)-Pro-NH-3-(6-am)-pico
tBuOOC-CH$_2$-(D,L)-(Thpg)-Pic-NH-3-(6-am)-pico
HOOC-CH$_2$-(L)-(Thpg)-Pic-NH-3-(6-am)-pico
HOOC-CH$_2$-(D)-(Thpg)-Pic-NH-3-(6-am)-pico
HOOC-CH$_2$-(D,L)-(Thpg)-Oxp-NH-3-(6-am)-pico
HOOC-CH$_2$-(D,L)-(Thpa)-Oxp-NH-3-(6-am)-pico
HOOC-CH$_2$-(D,L)-Chg-Thia-NH-3-(6-am)-pico
tBuOOC-CH$_2$-(D)-Chg-Pro-NH-3-(6-ham)-pico
BnOOC-CH$_2$-(D)-Chg-Pro-NH-3-(6-ham)-pico
MeOOC-CH$_2$-(D)-Chg-Pro-NH-3-(6-methoxycarbonyl-am)-pico
tBuOOC-CH$_2$-(D)-(tBu)Gly-Pic-NH-3-(6-am)-pico
HOOC-CH$_2$-(D)-(tBu)Gly-Pic-NH-3-(6-am)-pico
tBuOOC-CH$_2$-(D)-(neo-Pentyl)Gly-Pic-NH-3-(6-am)-pico
HOOC-CH$_2$-(D)-(neo-Pentyl)Gly-Pic-NH-3-(6-am)-pico
HOOC-CH$_2$-CH$_2$-(D)-Chg-Pro-NH-3-(6-am)-pico
HOOC-CH$_2$-(D)-(3,4,5-Trimethoxy)Phe-Pro-NH-3-(6-am)-pico
HOOC-CH$_2$-(D)-Chg-Pro-NH-3-(6-am-2-MeO)-pico
HOOC-CH$_2$-(D)-Cha-Pro-NH-3-(6-am-2-Me)-pico
HOOC-CH$_2$-(D)-Chg-Pro-NH-3-(6-am-4-MeO)-pico
HOOC-CH$_2$-(D)-Chg-Pro-NH-(6-am-4-Me)-pico
HOOC-CH$_2$-(D)-Cha-Pyr-NH-(2-MeO)-4-amb
HOOC-CH$_2$-(D)-Cha-Pyr-NH-3-(6-am)-pico
HOOC-CH$_2$-(D,L)-(Thpa)-Pyr-NH-3-(6-am)-pico
iPrOOC-CH$_2$-(D)-Chg-Pyr-NH-3-(6-am)-pico
HOOC-CH$_2$-(D,L)-(γ-Me)Cha-Pyr-NH-3-(6-am)-pico
HOOC-CH$_2$-(D,L)-Chea-Pyr-NH-3-(6-am)-pico
tBuOOC-CH$_2$-(D)-Chg-Oxp-NH-3-(6-am)-pico
HOOC-CH$_2$-(D)-Chg-Oxp-NH-3-(6-am)-pico
tBuOOC-CH$_2$-(D)-Cha-Oxp-NH-3-(6-am)-pico
HOOC-CH$_2$-(D)-Cha-Oxp-NH-3-(6-am)-pico
tBuOOC-CH$_2$-(D)-Chg-Pro-NH-3-(6-am)-pico
MeOOC-CH$_2$-(D)-Chg-Pro-NH-3-(6-am)-pico
CyclohexylOOC-CH$_2$-(D)-Chg-Pro-NH-3-(6-am)-pico
(tBuOOC-CH$_2$)$_2$-(D)-Chg-Pro-NH-3-(6-am)-pico
(HOOC-CH$_2$)$_2$-(D)-Chg-Pro-NH-3-(6-am)-pico
H$_2$NCO-CH$_2$-(D)-Chg-Pro-NH-3-(6-am)-pico
tBuNHCO-CH$_2$-(D)-Chg-Pro-NH-3-(6-am)-pico
tBuOOC-CH$_2$-(D)-Chg-Aze-NH-3-(6-am)-pico
HOOC-CH$_2$-(D)-Chg-Aze-NH-3-(6-am)-pico
tBuOOC-CH$_2$-(D)-Chg-Pic-NH-3-(6-am)-pico
HOOC-CH$_2$-(D)-Chg-Pic-NH-3-(6-am)-pico
tBuOOC-CH$_2$-(D)-Cha-Pro-NH-3-(6-am)-pico
HOOC-CH$_2$-(D)-Cha-Pro-NH-3-(6-am)-pico
tBuOOC-CH$_2$-(D)-Cha-Pic-NH-3-(6-am)-pico
HOOC-CH$_2$-(D)-Cha-Pic-NH-3-(6-am)-pico
HOOC-CH$_2$-(D,L)-Cog-Pro-NH-5-(2-am)-pym List of abbreviations:
AIBN: Azobisisobutyronitrile
Ac: Acetyl
Ala: Alanine
am: Amidino
4-amb: 4-Amidinobenzyl
Asp: Aspartic acid
Aze: Azetidinecarboxylic acid
Bn: Benzyl
Boc: tert-Butyloxycarbonyl
Bu: Butyl
Cbz: Benzyloxycarbonyl
Cha: Cyclohexylalanine
Chea: Cycloheptylalanine
Chg: Cyclohexylglycine
Cog: Cyclooctylglycine
Cpa: Cyclopentylalanine
Cpg: Cyclopentylglycine
(Cyclo)Leu: 1-Aminocyclopentane-1-carboxylic acid
TLC: Thin-layer chromatography
DCC: Dicyclohexylcarbodiimide
Dch: Dicyclohexylalanine
Dcha: Dicyclohexylamine
DCM: Dichloromethane
DMF: Dimethylformamide
DIPEA: Diisopropylethylamine
Dpa: Diphenylalanine
Et: Ethyl
Eq: Equivalents
Gly: Glycine
ham: Hydroxyamidino
HOSucc: Hydroxysuccinimide
HPLC: High-performance liquid chromatography
Hyac: Hydroxyacetyl
Hyp: Hydroxyproline
Hypr: 2-Hydroxypropionyl
2-Ind: 2-Dihydroindolecarboxylic acid
iPr: Isopropyl
Leu: Leucine
Me: Methyl
MPLC: Medium pressure liquid chromatography
MTBE: Methyl tert-butyl ether
napme: naphthylmethyl
NBS: N-Bromosuccinimide
Oxp: Oxaproline (1,3-oxazolidine-4-carboxylic acid)
Ph: Phenyl
Phe: Phenylalanine
2Phi: 2-Perhydroindolecarboxylic acid
Pic: Pipecolic acid
pico: picolyl
pim: piperidinylmethyl
PPA: Propanephosphonic anhydride
Pro: Proline
Py: Pyridine
5-pym: 5-Pyrimidylmethyl
2-Pym: 2-Pyrimidylmethyl
Pyr: 3,4-Dehydroproline
RT: Room temperature
t: tertiary
tBu: tertiary-butyl tert: tertiary
TBAB: Tetrabutylammonium bromide
TEA: Triethylamine
TFA: Trifluoroacetic acid
TFFA: Trifluoroacetic anhydride
Thia: Thiaproline (1,3-thiazolidine-4-carboxylic acid)
Thpa: 4-Tetrahydropyranylalanine
Thpg: 4-Tetrahydropyranylglycine
1Tic: 1-Tetrahydroisoquinolinecarboxylic acid
3Tic: 3-Tetrahydroisoquinolinecarboxylic acid
Z: Benzyloxycarbonyl The invention furthermore relates to the compounds of the formulae

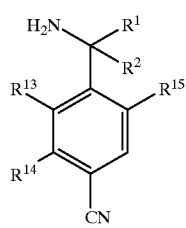

V

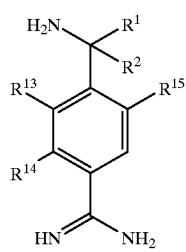

VI

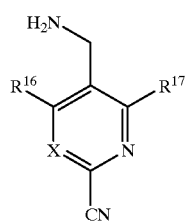

VII

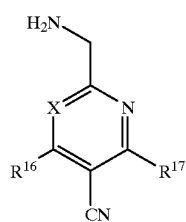

VIII

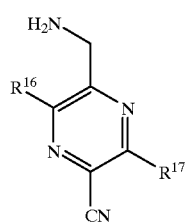

IX

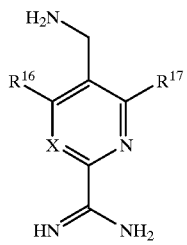

X

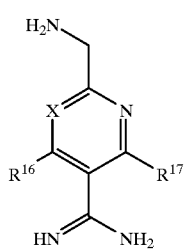

XI

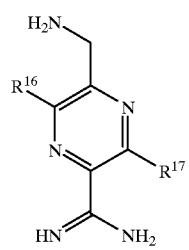

XII

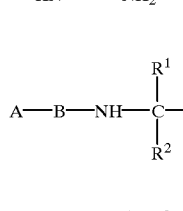

and

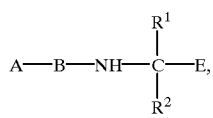

XIII where A, B, X, $R^1$, $R^2$, $R^{13}$, $R^{14}$, $R^{15}$, $R^{16}$ and $R^{17}$ have the stated meaning, and E is

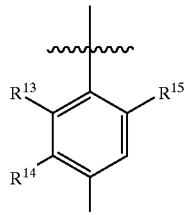 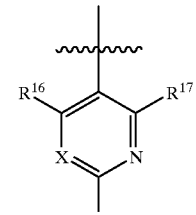

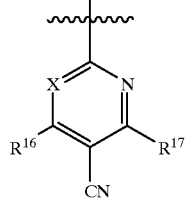

and in which the amidino functionality in formulae VI, X, XI and XII can be in mono- or diprotected form.

Particularly suitable protective groups for the protected form are the Cbz and Boc groups.

The novel intermediates are used to prepare the compounds I and are valuable building blocks for synthesizing serine protease inhibitors.

The structural fragment of the formula XIV

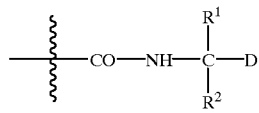

XIV in which D has the abovementioned meaning, is novel and is valuable as constituent of serine protease inhibitors and in particular of thrombin inhibitors.

The compounds of the formula I may exist as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The novel compounds can be used for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are furthermore suitable for combination therapy with thrombolytics such as streptokinase, urokinase, prourokinase, t-PA, APSAC and other plasminogen activators for shortening the reperfusion time and prolonging the reocclusion time.

Other areas of use are the prevention of thrombin-dependent early reocclusion and late restenosis after percutaneous transluminal coronary angioplasty, the prevention of thrombin-induced proliferation of smooth muscle cells, the prevention of the accumulation of active thrombin in the CNS (eg. in Alzheimer's disease), the control of tumors and the prevention of mechanisms which lead to adhesion and metastasis of tumor cells.

Their particular advantage is that they are also effective after oral administration.

The compounds according to the invention can be administered in a conventional manner orally or parenterally (subcutaneously, intravenously, intramuscularly, intraperitoneally, rectally). Administration can also take place with vapors or sprays through the nasopharyngeal space.

The dosage depends on the age, condition and weight of the patient and on the mode of administration. As a rule, the daily dose of active ingredient per person is about 10–2000 mg on oral administration and about 1–200 mg on parenteral administration. This dose can be given in 2 to 4 single doses or once a day as depot form.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active ingredients can for this purpose be mixed with conventional pharmaceutical auxiliaries such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 0.1 to 99 percent by weight of active ingredient.

Experimental part:

The compounds of the formula I can be prepared starting from the N-terminally protected α-amino acids or α-hydroxy carboxylic acids A—OH, The α-amino acid B—OH and the building block $H_2N$—$C(R^1R^2)$—E as shown in scheme 1 and 2. Classical methods of protective group and coupling chemistry are used for this purpose.

The radicals $R^3$ and $R^4$ or $R^7$ can alternatively be introduced after the coupling of the building blocks A—OH, B—OH and $H_2N$—$C(R^1R^2)$—E to give A—B—N—$C(R^1R^2)$—E after cleavage of the protective group from A or are a constituent of A—OH from the outset.

Scheme 1

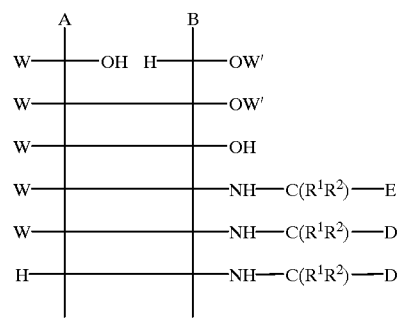

Scheme 2

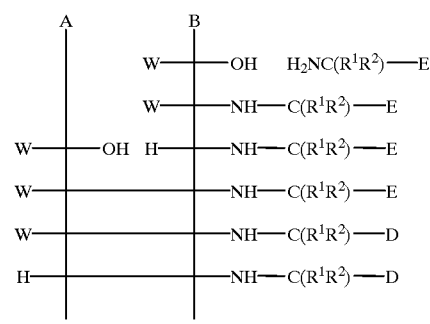

where W is one of the conventional N-terminal protective groups (preferably Boc or Cbz) and W' is methyl, ethyl, tert-butyl or benzyl.

The required coupling reactions and the conventional reactions for introducing and eliminating protective groups are carried out under standard conditions of peptide chemistry (see M. Bodanszky, A. Bodanszky "The Practice of Peptide Synthesis", 2nd edition, Springer Verlag Heidelberg, 1994).

Boc protective groups are eliminated using dioxane/HCl or TFA/DCM, and Cbz protective groups are eliminated by hydrogenolysis or with HF. The hydrolysis of ester functionalities takes place with LiOH in an alcoholic solvent or in dioxane/water. t-Butyl esters are cleaved with TFA.

N-terminal alkyl radicals (see $R^3$ and $R^4$) are introduced by reductive alkylation or direct N-alkylation.

Alkanoyl radicals (see $R^7$) are introduced by standard coupling reactions or esterification reactions.

The amidino functionality can be prepared from a nitrile functionality by several methods:

One method is classical Pinner synthesis (R. Boder, D. G. Neilson Chem. Rev. 61 (1961) 179) or a modified Pinner synthesis which passes through imino thioester salts as intermediate (H. Vieweg et al. Pharmazie 39 (1984), 226). Catalytic hydrogenation of N-hydroxyamidines, which are obtainable by addition of hydroxylamine onto the cyano group, with Raney nickel or Pd/C in alcoholic solvents likewise results in amidines (B. J. Broughton et al. J.Med. Chem. 18 (1975), 1117) and is particularly valuable for the synthesis of pharmaceutically active compounds.

The reactions were checked by TLC, normally using the following mobile phases:

| A. | DCM/MeOH | 95:5 |
| B. | DCM/MeOH | 9:1 |
| C. | DCM/MeOH | 8:2 |
| D. | DCM/MeOH/50% HOAc | 40:10:5 |
| E. | DCM/MeOH/50% HOAc | 35:15:5 |

Where separations by column chromatography are mentioned, these were separations on silica gel using the abovementioned mobile phases.

Reversed phase HPLC separations were carried out with acetonitrile/water and HOAc buffer.

The starting compounds can be prepared by the following methods:

A wide variety of possibilities is available in the literature for the general and specific synthesis of amino acids. A summary thereof is provided, inter alia, by Houben-Weyl, volume E16d/part 1, pages 406 et seq.

Frequently used precursors were N-(diphenylmethylene) glycine ethyl ester, diethyl acetamidomalonate and ethyl isocyanoacetate.

Various glycine and alanine derivatives were prepared, for example, starting from ethyl isocyanoacetate and an appropriate ketone or aldehyde (see H.-J. Prätorius, J. Flossdorf, M.-R. Kula Chem. Ber. 108 (1975) 3079).

Boc-Cyclooctylglycine, Boc-2-norbornylglycine, Boc-adamantylalanine, Boc-γ-methylcyclohexylalanine and Boc-(4-Me)cyclohexylglycine were synthesized via the corresponding ethyl 2-formylaminoacrylates (U. Schöllkopf and R. Meyer, Liebigs Ann. Chem. (1977) 1174) starting from ethyl isocyanoacetate with the respective carbonyl compounds cyclooctanone, 2-norbornanone, 1-formyladamantane, 1-formyl-1-methylcyclohexane, and 4-methylcyclohexanone by the following general methods:
General method for synthesizing the ethyl 2-formylaminoacrylates A solution of 100 mmol of ethyl isocyanoacetate in 50 ml of THF is added dropwise to 100 mmol of potassium tert-butoxide in 150 ml of THF at 0 to −10° C. After 15 min, 100 mmol of the appropriate carbonyl compound in 50 ml of THF is added at the same temperature, the reaction mixture is slowly allowed to rise to RT and the solvent is stripped off in a rotary evaporator. The residue is mixed with 50 ml of water, 100 ml of acetic acid and 100 ml of DCM and the product is extracted with DCM. The DCM phase is dried over $Na_2SO_4$, and the solvent is stripped off in a rotary evaporator. The resulting products are almost pure and can, if required, be further purified by column chromatography on silica gel (mobile phase: ethyl/petroleum ether mixtures).
General method for amino acid hydrochlorides starting from the ethyl 2-formylaminoacrylates 100 mmol of ethyl 2-formylaminoacrylates are hydrogenated with Pd/C (10%)/hydrogen in 200 ml of glacial acetic acid until conversion is complete. The catalyst is then filtered off, the acetic acid is stripped off as far as possible in a rotary evaporator, and the residue is refluxed in 200 ml of 50% concentrated hydrochloric acid for 5 h. The hydrochloric acid is stripped off in a rotary evaporator, and the product is dried at 50° C. under reduced pressure and washed several times with ether. The hydrochlorides result as slightly colored crystals.

25.0 g of cyclooctylglycine hydrochloride were obtained starting from 18.9 g (150 mmol) of cyclooctanone. 26.6 g of 2-norbornylglycine hydrochloride were obtained starting from 16.5 g (150 mmol) of 2-norbornanone. 26.0 g of adamantylalanine hydrochloride were obtained starting from 19.7 g (120 mmol) of 1-formyladamantane. 16.6 g of γ-methylcyclohexylalanine hydrochloride were obtained starting from 12.6 g (100 mmol) of 1-formyl-1-methylcyclohexane. 25.9 g of 4-methylcyclohexylglycine hydrochloride were obtained starting from 16.8 g (150 mmol) of 4-methylcyclohexanone.

The amino acid hydrochlorides were converted by conventional processes using di-tert-butyl dicarbonate in water/dioxane into the Boc-protected form in each case and subsequently recrystallized from ethyl acetate/hexane mixtures or purified by column chromatography on silica gel (mobile phase: ethyl acetate/petroleum ether mixtures).
N-tert-Butyloxycarbonyl-(D)-α-methyl-cyclohexylalanine 3.4 g (12.2 mmol) of Boc-(D)-α-methyl-Phe-OH were hydrogenated in 100 ml of MeOH at 50° C. in the presence of 250 mg of 5% Rh on $Al_2O_3$ under 10 bar of hydrogen for 24 h. Filtration and stripping-off of the solvent resulted in 2.8 g of Boc-(D)-α-Methyl-Cha-OH.

$^1$H-NMR (DMSO-d$^6$, δ in ppm): 12 (very broad signal, COOH); 1.7–0.8 (25 H; 1.35 (s, Boc), 1.30 (s,Me))
Preparation of Boc-trimethylsilylalanine The preparation took place both in optically active form as described by B. Weidmann, Chimica 46 (1992) 312 and in racemic form from N-(diphenylmethylene)glycine ethyl ester and trimethylsilylmethyl iodide.
N-tert-Butyloxy-(D,L)-trimethylsilylalanine 5.67 g (21.2 mol) of N-(diphenylmethylene)glycine ethyl ester in 35 ml of THF were deprotonated with a THF solution of LDA under standard conditions. To this were added dropwise at −70° C. 5.0 g (23.4 mmol) of trimethylsilyl methyl iodide in 10 ml of THF, and the reaction mixture was allowed to rise slowly to RT. Workup resulted in 7.2 g of N-(diphenylmethylene)trimethylsilylalanine ethyl ester, which was cleaved with 0.5 N HCl without further purification. The resulting hydrochloride was converted with $NaHCO_3$ solution into 3.4 g of trimethylsilylalanine ethyl ester and converted under conventional conditions with di-tert-butyl dicarbonate into the Boc-protected compound almost quantitatively. The ethyl ester was hydrolyzed with dilute sodium hydroxide solution in methanol, the resulting salt was protonated with dilute hydrochloric acid, and the product was extracted with ethyl acetate/ether 1:1. 4.0 g of Boc-trimethylsilylalanine were obtained.

$^1$H-NMR (DMSO-d$^6$, δ in ppm): ~12 (very broad signal, COOH); 7.00 (d,1H,NH), 1.35 (s,9H,3 $CH_3$), 0.95 (d,2H, $CH_2$).

Boc-N-Cyclopropylglycine was prepared from N-cyclopropylglycine ethyl ester, ethyl bromoacetate and cyclopropylamine (similar to J. W. Skiles et al., J. Med. Chem. 35 (1992) 641) and then converted under standard conditions into the Boc-protected form, then hydrolyzed with MeOH/2N NaOH and finally acidified with 1N HCl.

Boc-Suberylglycine was synthesized in a similar way to the literature method (O. P. Goel et al. Tetrahedron Lett. 34 (1993) 953).

Adamantylglycine can also be prepared by the method of Y. N. Belokon et al. Zhu. Org. Khi, 21, (1985) 1327.

Boc-(3-Ph)-Pro-OH was synthesized by a method similar to that of J. Y. L. Chung et al. (J.Org.Chem. 55 (1990) 270).

Preparation of Boc-1-tetralinylglycine

Boc-1-Tetralinylglycine was prepared starting from 1,2-dihydronaphthalene, which was initially converted with HBr into 1-tetralyl bromide (similar to J. Med. Chem. 37 (1994) 1586). The bromide was then reacted with diethyl acetamidomalonate, and the α-amino acid obtained after hydrolytic cleavage was converted under standard conditions into the Boc-protected form. Another possible preparation is described by E. Reimann and D. Voss (Arch. Pharm 310, (1977) 102).

Preparation of Boc-cycloleucine

Boc-Cycloleucine was prepared by the method of E. C. Jorgensen (J. Med. Chem. 14 (1971) 904).

Preparation of Boc-1-(D,L)-Tic-OH

Boc-1-(D,L)Tic-OH was prepared by a method of R. T. Shuman et al. (J. Med. Chem. 36 (1993) 314).

Preparation of Boc-(D,L)-Dch-OH

Boc-(D,L)-Dpa-OH (1 mmol) was hydrogenated in 12 ml of MeOH together with catalytic amounts of 5% Rh/$Al_2O_3$ under 5 bar. Filtration and removal of the solvent under reduced pressure resulted in the product in quantitative yield.

Preparation of 4-isopropylcyclohexylglycine and 3,3-dimethylcyclohexylglycine

These amino acids were prepared by reacting the ketones 4-isopropylcyclohexanone and 3,3-dimethylcyclohexanone with ethyl isocyanoacetate by a method of H.-J. Prätorius, J. Flossdorf and M. Kula (Chem. Ber. 108 (1975) 3079).

Boc-(D,L)-(3,4,5-(MeO)$_3$)Phe-OH was prepared by alkylation of N-(diphenylmethylene)glycine ethyl ester with trimethoxybenzyl chloride, followed by introduction of the Boc protective group and ester hydrolysis.

Preparation of Boc-D,L-Chea-OH 4.0 g of cycloheptylmethyl methanesulfonate (19.39 mmol), prepared from cycloheptylmethanol and methanesulfonyl chloride, were refluxed together with 4.9 g of N-(diphenylmethylene)glycine ethyl ester (18.47 mmol), 8.9 g of dry, finely powdered potassium carbonate (64.65 mmol) and 1 g of tetrabutylammonium bromide (3 mmol) in 50 ml of dry acetonitrile under an inert gas atmosphere for 10 h. The potassium carbonate was then filtered off, the filtrate was evaporated to dryness, and the crude product was immediately hydrolyzed with 20 ml of 2N hydrochloric acid in 40 ml of ethanol by stirring at RT for 1.5 h. The reaction solution was diluted and then benzophenone was extracted with ethyl acetate in the acid range, and subsequently H-D,L-Chea-OEt was extracted with DCM in the alkaline range (pH=9), and the solution was dried over magnesium sulfate and evaporated in a rotary evaporator. Yield: 3.7 g=95% of theory.

The conversion to Boc-D,L-Chea-OH took place in a conventional way via Boc-D,L-Chea-OC$_2$H$_5$ and subsequent ester hydrolysis.

Preparation of 4-tetrahydropyranylglycine (a) 5-(4-Tetrahydropyranyl)hydantoin 90 g (0.774 mol) of 4-formyltetrahydropyran were added dropwise to a solution of 84.6 g (0.813 mol) of sodium bisulfite in 250 ml of water. The mixture was then diluted with 500 ml of ethanol and, at 20° C., 300 g of ammonium carbonate and 100 g of potassium cyanide were added. The reaction mixture was stirred at 50° C. for 5 h and at RT overnight.

For workup, the ethanol was stripped off under reduced pressure. The product was deposited in the form of colorless crystals after acidification of the aqueous phase with conc. hydrochloric acid. 141 g of the hydantoin were obtained.

(b) 4-Tetrahydropyranylglycine 10 g (54.3 mmol) of the hydantoin prepared above were heated with 25.7 g (81.5 mmol) of barium hydroxide in 130 ml of water under autogenous pressure in an autoclave at 165° C. for 5 h. The resulting suspension was neutralized with dry ice at 50° C. After cooling to 20° C., the mixture was acidified with conc. sulfuric acid, and the barium sulfate precipitate was filtered off. The aqueous solution was neutralized with ammonia and left to stand for crystallization. 5.3 g of 4-tetrahydropyranylglycine were obtained.

(c) Boc-4-Tetrahydropyranylglycine 3.20 g (20.1 mmol) of 4-tetrahydropyranylglycine were Boc-protected with 4.39 g (20.1 mmol) of di-tert-butyl dicarbonate by a conventional process. Workup resulted in 4.8 g of Boc-4-tetrahydropyranylglycine. $^1$H-NMR (DMSO-d$^6$, δ in ppm) –12.5 (broad signal, 1H, COOH), 7.05 (d,1H,NH), 3.9–3.7 (3H, CH and 1H from each of 2CH$_2$), 3.3–3.1 (2H, 1H from each of 2CH$_2$), 1.85 (m, 1H, CH), 1.5–1.2 (13H, 2CH$_2$ and Boc)

N-tert-Butyloxycarbonyl-(D,L)-4-tetrahydropyranylalanine

4-Bromomethyltetrahydropyran, which was prepared by reacting 4-hydroxymethyltetrahydropyran (see DE 92 42 33 430) with PBr$_3$, and diethyl acetamidomalonate, previously deprotonated with NaH in DMF, were converted into diethyl acetamido(4-tetrahydropyranylmethyl) malonate, and the esters and the acetyl group were then hydrolyzed, with simultaneous decarbonylation, with 6N HCl and glacial acetic acid at 100° C. to give 4-tetrahydropyranylalanine hydrochloride.

The amino group was protected with a Boc group by a process known from the literature. The crude product was taken up in ethyl acetate, extracted with 0.5N NaOH, the aqueous phase was acidified with 1N HCl, and the product was extracted with DCM. After drying over Na$_2$SO$_4$, the solvent was completely stripped off. Pure N-tert-butyloxycarbonyl-(D,L)-4-tetrahydropyranylalanine was obtained.

$^1$H-NMR (DMSO-d$^6$, δ in ppm): –12.5 (broad signal, 1H, COOH), 7.10 (d, 1H, NH), 3.95 (m, 1H), 3.80 (m, 2H, 1H from each of 2 CH$_2$ groups), 3.20 (m, 2H, 1H from each of 2 CH$_2$ groups), 1.75–1.0 (16H, 3×CH$_2$, CH and Boc).

Hydroxyacetic acid derivatives were prepared either by methods similar to that of S. Bajusz (WO 93/18060) or starting from corresponding methyl acetate derivatives by α-hydroxylation using Davis' reagent (F. A. Davis, L. C. Vishwkarma, J. M. Billmers J.Org.Chem. 49 (1984) 3241).

The H$_2$N—C(R$^1$R$^2$)—D' building blocks were prepared in the following way:

1. Preparation of 6-cyano-3-picolylamine:
   (a) 6-Cyano-3-picolyl azide
      14.5 g (0.07 mol) of TFAA dissolved in 20 ml of DCM were added dropwise to a solution of 8.8 g (0.07 mol) of 6-cyano-3-picolyl alcohol and 6.9 g of TEA in 200 ml of DCM at RT and the mixture was then stirred for 2 h. The residue after removal of the DCM by distillation was dissolved in a mixture of toluene and 50 ml of DMSO, 11.2 g (0.17 mol) of NaN$_3$ and 0.7 g of TBAB were added, and the mixture was stirred at RT overnight.

The reaction mixture was poured into 300 ml of water and extracted several times with ether. After drying with Na$_2$SO$_4$ and removal of the solvent under reduced pressure, 6.8 g of yellowish crystals remained and were used without further purification in the next reaction.

(b) 6-Cyano-3-picolylamine

The compound obtained in (a) was dissolved in 45 ml of THF and 1.2 ml of water and, while stirring, 11.2 g of triphenylphosphine were added in portions. The reaction mixture was left to stand at RT overnight.

After removal of the solvent by distillation, the residue was taken up in 100 ml of ether, the precipitated triphenylphosphine oxide was filtered off with suction, and the filtrate was adjusted to pH 2 with ethereal hydrochloric acid. The precipitated hydrochloride was filtered off with suction, washed with ether and digested successively with toluene and hot isopropanol. 4.7 g of hydrochloride were isolated, melting point 253–256° C. (decomposition).

2. Preparation of 5-aminomethyl-2-cyanopyrimidine:

(a) 2-Methylthio-5-hydroxycarbonylpyrimidine

1 Eq. of 2-methylthio-5-ethoxycarbonylpyrimidine were dissolved in dioxane and, after addition of 2 eq. of 2N LiOH, stirred overnight. The solvent was then removed under reduced pressure, and the residue was dissolved in EtOH. After addition of a stoichiometric amount of ethereal HCl, the solution was again evaporated to dryness. Water which was still present was removed by azeotropic drying with toluene once.

(b) 2-Methylthio-5-hydroxymethylpyrimidine

The acid obtained in 2.(a) was reduced to the alcohol by a method of A. I. Meyers et al. (Org.Synth. Coll. Vol. VII, 530). Yield: 40%. FAB-MS (M$^+$)=156

(c) 2-Methylthio-5-aminomethylpyrimidine

The resulting alcohol was converted into the amine and isolated as hydrochloride as described above. Yield: 30%. FAB-MS (M$^+$)=155

(d) N-Boc-5-aminomethyl-2-methylthiopyrimidine

5-Aminomethyl-2-methylthiopyrimidine hydrochloride was protected with a Boc group under standard conditions (see M. Bodanszky, A. Bodanszky "The Practice of Peptide Synthesis", 2nd edition, Springer Verlag Heidelberg, 1994). Yield: 73%. FAB-MS (M$^+$)=255

(e) N-Boc-5-aminomethyl-2-methylsulfonylpyrimidine

1 Eq. of N-Boc-5-aminomethyl-2-methylthiopyrimidine was introduced into acetic acid at 70–80° C. Then 2.5 eq. of $H_2O_2$ (50% strength) were slowly added dropwise. After conversion of the precursor was complete, the reaction mixture was concentrated to one third of the volume and poured into water. The precipitated solid was filtered off and dried in a desiccator over phosphorus pentoxide. Yield: 37%. FAB-MS (M$^+$)=283

(f) N-Boc-5-aminomethyl-2-cyanopyrimidine

1 Eq. of N-Boc-5-aminomethyl-2-methylsulfonylpyrimidine was dissolved in DMF and introduced into a reflux apparatus. After addition of 2 eq. of KCN and catalytic amounts of 18-crown-6, the reaction mixture was stirred at 60° C. for 4 h. The suspension was then concentrated and poured into 200 ml of water. The precipitated solid was filtered off with suction and dissolved in ethyl acetate. The solution was washed with water and saturated NaCl solution, dried and evaporated in a rotary evaporator. N-Boc-5-aminomethyl-2-cyanopyrimidine was used as crude product without further purification in the next reaction. Yield: 46%.

(g) 5-Aminomethyl-2-cyanopyrimidine hydrochloride

1 Eq. of N-Boc-5-aminomethyl-2-cyanopyrimidine was introduced into dioxane at RT and, after addition of dioxane/HCl (5M), stirred at RT for 3 h. After conversion of the precursor was complete (TLC check: mobile phase A), the reaction mixture was concentrated and poured into ether. The precipitated solid was filtered off with suction, again dissolved in MeOH and poured into ether. The product was filtered off with suction and dried under high vacuum to afford 89% of the theoretical yield of 5-aminomethyl-2-cyanopyrimidine hydrochloride. FAB-MS (M$^+$)=134

3. Preparation of 4-aminomethyl-3-methoxybenzonitrile (a) 3-Nitro-4-methylbenzonitrile 399 g (2.56 mol) of p-toluonitrile were added over the course of 90 minutes to 1 l of fuming nitric acid at −10° C. 1 h after the addition, the mixture was poured onto 2.5 l of ice/$H_2O$, whereupon a solid precipitated and was removed on a suction filter funnel and washed to neutral pH with water. The yield of the product was 363 g (88%). $^1$H-NMR (CDCl$_3$; δ in ppm): 8.3 (d, 1H); 7.8 (dd, 1H); 7.5 (dd, 1H); 2.7 (s, 3H)

(b) 3-Amino-4-methylbenzonitrile:

120 g of 3-nitro-4-methylbenzonitrile were suspended in 1.2 l of EtOH and hydrogenated with 50 l of hydrogen at RT in the presence of 7 g of Pd/C (10%). After removal of the catalyst on Celite, the solvent was stripped off to result in 95 g of pure product (97%). $^1$H-NMR (DMSO-d$^6$; δ in ppm): 7.1 (dd, 1H); 6.90 (d, 1H); 6.85 (dd, 1H); 5.35 (s, 2H, NH$_2$); 2.15 (s, 3H)

(c) 3-Hydroxy-4-methylbenzonitrile:

A solution of 49.2 g (0.72 mol) of NaNO$_2$ in 217 ml of water was added dropwise over the course of 30 min to 85 g (0.72 mol) of 3-amino-4-methylbenzonitrile in 1.8 l of 6N HCl at 0–5° C. The mixture was then stirred at 0–5° C. for a further 30 min and then at the boiling point for 1 h. After the solution had cooled it was possible to extract the product with ethyl acetate and, from this, the phenolate with ice-cold 5N NaOH. The aqueous phase was then acidified to pH 3 with 6N HCl and the product was extracted with ethyl acetate. 41 g (43%) of the phenol were obtained. $^1$H-NMR (DMSO-d$^6$; δ in ppm): 10.3 (s, OH); 7.25 (dd, 1H); 7.15 (d, 1H); 7.1 (dd, 1H); 2.20 (s, 3H)

(d) 3-Methoxy-4-methylbenzonitrile:

15 g (0.11 mol) of 3-hydroxy-4-methylbenzonitrile dissolved in 30 ml of DMF were added dropwise to a suspension of 0.11 mol of NaH and 30 ml of DMF, and the mixture was stirred until no further $H_2$ evolution was observed. Then 10.6 ml (0.17 mol) of methyl iodide were added dropwise, and the mixture was stirred at RT for 1 h. The solution was poured into ice-water, and the product was extracted with ether/ethyl acetate 7:1. After the solvent had been stripped off, the product began slowly to crystallize. 14.8 g (89%) of the product were obtained. $^1$H-NMR (CDCl$_3$; δ in ppm): 7.2 (m, 2H); 7.02 (s, 1H); 3.85 (s, 3H); 2.25 (s, 3H)

(e) 4-Bromomethyl-3-methoxybenzonitrile:

14.7 g (0.1 mol) of 3-methoxy-4-methylbenzonitrile were dissolved in 210 ml of 1,2-dichloroethane, bromination was carried out at 82° C. in the presence of catalytic amounts of AIBN with 19.1 g (0.11 mol) of NBS in portions over the course of 1 h and, after the addition was complete, the mixture was stirred at 82° C. for a further 30 min. Addition of n-heptane was followed by removal of precipitated succinimide, and the solvent was stripped off. The product contained, besides small amounts of precursor, also traces of the corresponding benzal bromide. $^1$H-NMR (DMSO-d$^6$; δ in ppm): 7.60 (dd, 1H); 7.50 (d, 1H); 7.40 (dd, 1H); 4.68 (s, 2H); 3.96 (s, 3H)

(f) 4-Phthalimidomethyl-3-methoxybenzonitrile:

24.4 g (108 mol) of 4-bromomethyl-3-methoxybenzonitrile dissolved in 125 ml of DMF and 20.0 g of potassium phthalimide were stirred at RT for 24 h and then at 50° C. for 1 h. The mixture was poured into water, whereupon the product precipitated as solid. 21.5 g (68%) of the product were obtained. $^1$H-NMR (DMSO-d$^6$; δ in ppm): 7.9 (m, 4H); 7.5 (d, 1H); 7.35–7.25 (m, 2H); 7.78 (s, 2H); 3.92 (s, 3H)

(g) 4-Aminomethyl-3-methoxybenzonitrile:

10.6 ml of hydrazine hydrate were added to 21.2 g (73 mmol) of 4-phthalimidomethyl-3-methoxybenzonitrile dissolved in 290 ml of THF, and the mixture was stirred at RT for 20 h. Then 180 ml of 2N HCl were added dropwise and, after 1.5 h, the solvent was completely stripped off. The residue was taken up in MTBE, extracted with 1N HCl, adjusted to pH 9–10 with 2N NaOH and extracted with DCM. 8.0 g (68%) of the product were obtained. $^1$H-NMR (DMSO-d$^6$; δ in ppm): 7.55 (dd, 1H); 7.40 (dd, 1H); 7.37 (d, 1H); 3.85 (s, 3H); 3.70 (s, 2H); 2.5–1.6 (NH$_2$).

4. Preparation of 4-aminomethyl-3-ethoxybenzonitrile:

(a) 3-Ethoxy-4-methylbenzonitrile 10 g (75 mmol) of 4-methyl-3-hydroxybenzonitrile were deprotonated with 1 eq. of NaH in 100 ml of DMF and then ethylated on the oxygen with 112 mmol of iodoethane. 8.8 g of product were obtained.

$^1$H-NMR (DMSO-d$^6$, δ in ppm): 7.4–7.25 (3H), 4.10 (q, 2H), 2.22 (s, 3H), 1.35 (t, 3H)

(b) 4-Bromomethyl-3-ethoxybenzonitrile

Preparation took place as in Example 3.(e) with NBS. $^1$H-NMR (DMSO-d$^6$, δ in ppm): 7.59 (1H), 7.50 (1H), 7.40 (1H), 4.65 (s, 2H), 4.20 (q, 2H), 1.35 (t, 3H)

(c) 4-Aminomethyl-3-ethoxybenzonitrile hydrochloride

Synthesis took place via the stage of the corresponding phthalimide as in Example 3.(f) and to give the hydrochloride product by cleavage with hydrazine and treatment with HCl as in Example 3.(g). Starting from 10 g of precursor (a), 5.1 g of the product were obtained. $^1$H-NMR (DMSO-d$^6$, δ in ppm): 8.5 (broad signal, NH$_3^+$), 7.65–7.45 (3H), 4.18 (q, 2H), 4.05 (s, 2H), 1.38 (t, 3H).

5. Preparation of 4-aminomethyl-3-benzyloxybenzonitrile:

(a) 3-Benzyloxy-4-hydroxymethylbenzonitrile 33.1 g of 4-formyl-3-hydroxybenzonitrile (Liebigs Ann. Chem. (1982) 1836) were O-benzylated with 1 eq. each of benzyl bromide and K$_2$CO$_3$ and, after workup, reduced with NaBH$_4$ in 100 ml of MeOH/THF 2:3 at −10° C. to 0° C. to give the alcohol. 22.4 g were obtained. The product could be crystallized from DCM/petroleum ether. $^1$H-NMR (CDCl$_3$, δ in ppm): 7.48 (1H), 7.40–7.3 (5H), 7.20 (1H), 7.08 (1H), 5.05 (s, 2H), 4.75 (s, 2H), 2.85 (1H, OH)

(b) 3-Benzyloxy-4-bromomethylbenzonitrile:

4.3 g (18 mmol) of the alcohol (a) underwent substitution in 40 ml of THF with 7.9 g (24 mmol) of CBr$_4$ and 6.3 g (24 mmol) of PPh$_3$, which was added in portions over the course of 30 min. The reaction mixture was stirred at RT for 20 h. The product was purified by column chromatography (mobile phase: t-butyl methyl ether/petroleum ether 2:1). 4.6 g were obtained. $^1$H-NMR (DMSO-d$^6$, δ in ppm): 7.70–7.25 (8H), 5.30 (s, 2H), 4.70 (s, 2H)

(c) 4-Aminomethyl-3-benzyloxybenzonitrile

Synthesis took place via the stage of the corresponding phthalimide as in Example 3.(f). The hydrazine cleavage was carried out as in Example 3.(g). The free amine was generated at pH 9–10 from the initially produced hydrochloride and was extracted from the aqueous solution with ether. $^1$H-NMR (DMSO-d$^6$, δ in ppm): 7.65–7.25 (8H), 5.20 (s, 2H), 3.80 (s, 2H), ca. 3.0 (broad signal, NH$_2$)

6. Preparation of 4-aminomethyl-3-iodobenzonitrile:

(a) 3-Iodo-4-methylbenzonitrile 25.3 g (0.15 mol) of 3-amino-4-methylbenzonitrile hydrochloride (Example 3.(b)) were converted in a Sandmeyer reaction into 22.1 g of product. $^1$H-NMR (DMSO-d$^6$, δ in ppm): 8.30 (1H), 7.78 (1H), 7.50 (1H), 2.45 (3H)

(b) 4-Bromomethyl-3-iodobenzonitrile

Preparation took place as in Example 3.(e) with NBS.

$^1$H-NMR (DMSO-d$^6$, δ in ppm): 8.38 (1H), 7.89 (1H), 7.77 (1H), 4.78 (2H)

(c) 4-Aminomethyl-3-iodobenzonitrile hydrochloride 12.1 g (37.6 mmol) of 4-bromomethyl-3-iodobenzonitrile in 200 ml of MeOH/THF 1:1 were slowly added dropwise to 200 ml of conc. ammonia solution/MeOH (saturated with NH$_3$) 1:1, simultaneously passing NH$_3$ into the reaction mixture. The temperature was maintained at 50° C. After 4 h, the solvent was stripped off, and the product was taken up in DCM, dried and precipitated with ethereal HCl. 8.6 g of 4-aminomethyl-3-iodobenzonitrile hydrochloride were obtained. $^1$H-NMR (DMSO-d$^6$, δ in ppm): 8.8 (broad signal, NH$_3^+$), 8.43 (1H), 7.98 (1H), 7.70 (1H), 4.13 (2H)

7. Preparation of 4-aminomethyl-2-methoxybenzonitrile:

(a) 2-Methoxy-4-methylbenzonitrile 10.7 g (78.6 mmol) of 4-methylsalicylaldehyde (J. C. S. Perkin I (1980) 1862) were methylated with 5.8 ml of MeI in the presence of 13 g of K$_2$CO$_3$ in 40 ml of DMF. The reaction mixture was poured into ice-water, and the product (11.5 g) was extracted with ether. The aldehyde was converted into the nitrile by a method similar to that in Synthesis (1978) 11. $^1$H-NMR (DMSO-d$^6$, δ in ppm): 7.60 (d, 1H), 7.05 (s, 1H), 6.90 (d, 1H), 3.90 (s, 3H), 2.40 (s, 3H)

(b) 4-Bromomethyl-2-methoxybenzonitrile 4.6 g (31.3 mmol) of 4-methyl-2-methoxybenzonitrile were brominated with 34.7 mmol of N-bromosuccinimide in the presence of catalytic amounts of azobisisobutyronitrile in 60 ml of 1,2-dichloroethane under reflux. 2.5 g of the product were obtained. $^1$H-NMR (DMSO-d$^6$, δ in ppm): 7.75 (d, 1H), 7.35 (s, broad, 1H), 7.15 (d, broad, 1H), 4.73 (s, 2H), 3.95 (s, 3H)

(c) 4-Aminomethyl-2-methoxybenzonitrile 2.5 g of the bromide (b) were introduced into 10 ml of MeOH, and NH$_3$ was passed in during dropwise addition of 38 ml of conc. ammonia/MeOH 1:1. After 2 h, the solvent was stripped off, the product was taken up in DCM and washed with water, and the organic phase was dried over Na$_2$SO$_4$. The product was precipitated as hydrochloride with ethereal HCl. $^1$H-NMR (DMSO-d$^6$, δ in ppm): 8.6 (broad signal, NH$_3^+$), 7.79 (1H), 7.55 (1H), 7.20 (1H), 4.10 (s, 2H), 3.93 (s, 3H)

8. Preparation of 4-aminomethyl-2-benzyloxybenzonitrile:

(a) 2-Benzyloxy-4-hydroxymethylbenzonitrile 41 ml (41 mmol) of a 1 molar BBr$_3$ solution in DCM were added dropwise to 5.5 g (37.4 mmol) of 2-methoxy-4-methylbenzonitrile (Example 7(a)) in 100 ml of DCM at 0° C., and the mixture was stirred at 0° C. for 1 h and at RT for a further 2 days. The mixture was poured into 10% strength ammonia solution, and the 2-hydroxy-4-methylbenzonitrile was extracted with DCM. The formyl group was generated from the methyl group by the method in Liebigs Ann. Chem. (1982) 1836, and the 4-formyl-2-hydroxybenzonitrile was converted into 2.1 g of 2-benzyloxy-4-hydroxymethylbenzonitrile as in Example 5.(a).

(b) 4-Aminomethyl-2-benzyloxybenzonitrile 2.1 g (8.8 mmol) of the benzyl alcohol (a) were converted as in Example 5.(b) with CBr$_4$ and PPh$_3$ into 2.2 g of 2-benzyloxy-4-bromomethylbenzonitrile. The benzylamine was synthesized as in Example 3.(f) and 3.(g) via the stage of the phthalimide to give 4-aminomethyl-2-benzyloxybenzonitrile.

9. Preparation of 4-aminomethyl-2-chlorobenzonitrile:

11.75 g (77.2 mmol) of 4-methyl-2-nitroaniline underwent a Sandmeyer reaction in a conventional process by diazotization and substitution with NaCN and CuSO$_4$ to give 9.6 g of crude 4-methyl-2-nitrobenzonitrile. $^1$H-NMR (DMSO-d$^6$, δ in ppm): 8.25 (1H), 8.05 (1H), 7.80 (1H), 2.50 (3H)

The nitro group was hydrogenated as in Example 3.(b), and the resulting 2-amino-4-methylbenzonitrile was subjected to another Sandmeyer reaction to give 2-chloro-4-methylbenzonitrile. The subsequent reactions to give 4-bromomethyl-2-chlorobenzonitrile, 2-chloro-4-phthalimidomethylbenzonitrile and finally 4-aminomethyl-2-chlorobenzonitrile took place as in Examples 3.(e), 3.(f) and 3.(g).

10. Preparation of 6-carbamoyl-3-picolylamine dihydrochloride:

67 g (0.46 mol) of 5-cyanopyridine-2-carboxamide (Chem. Ber. 117 (1984) 1259) were suspended in 1 l aqueous methanol (1/1) and 84.7 ml (1.9 equivs.) of conc. HCl, 21,4 g of 10% strength Pd/C were added and hydrogenation was carried out in a shaken vessel at room temperature for 5 h (H$_2$ uptake: 23.2 l; theory: 22.3 l). The product dissolved during the hydrogenation (and the catalyst changed from gray to black). TLC (CH$_2$Cl$_2$/MeOH 9/1, NH$_3$-saturated) revealed only traced of starting material.

The catalyst was filtered off with suction and washed with water, and the filtrate was evaporated under reduced pressure, finally with the addition of toluene and ethanol.

The moist residue was briefly refluxed in about 400 ml of MeOH, after cooling and stirring in an ice bath for about 30 minutes, filtered off with suction and washed with methyl t-butyl ether.

78 g (76.5%) of dihydrochloride were isolated as white crystals, melting point>260° C.

EXAMPLE 1

3-Phenyl-(D)-lactylproline p-amidinobenzylamide acetate:

(a) 3-Phenyl-(D)-lactylproline p-cyanobenzylamide:

5.5 g (20.4 mmol) of O-tetrahydropyranyl-3-phenyl-(D)-lactic acid (WO 93/18060) were dissolved in 30 ml of DMF, and 5.4 g (20.4 mmol), N-(p-cyanobenzyl)prolineamide, 3.3 g (20.4 mmol) of N-hydroxybenzotriazole, 3.0 g of DIPEA and 4.33 g (20.6 mmol) of dicyclohexylcarbodiimide were successively added. The mixture was stirred at RT for 48 h. The precipitated urea was filtered off with suction and then the solvent was substantially removed under reduced pressure, 50 ml of water were added to the residue, and extraction was carried out with ethyl acetate. After washing with water and NaHCO$_3$ solution and drying over Na$_2$SO$_4$, the ethyl acetate was distilled off, and the remaining oily residue was dissolved in methanol and adjusted to pH 2 with p-toluenesulfonic acid. This solution was left to stand at RT for 6 h. The methanol was then distilled off, the residue was taken up in ethyl acetate, and the solution was washed with water, 5% strength citric acid and NaHCO$_3$ solution. The residue obtained after drying over Na$_2$SO$_4$ and removal of the solvent by distillation was purified by column chromatography (eluent: methylene chloride/acetone/methanol, 45/5/2). 2.5 g of white crystals were obtained, and these melted at 108–110° C. after crystallization from an ether/hexane mixture.

(b) 3-Phenyl-(D)-lactylproline p-amidinobenzylamide acetate:

2.0 g of the above compound and 3 ml of triethylamine were dissolved in 30 ml of pyridine, saturated with H$_2$S at 0° C. and left to stand at RT overnight. A TLC check (CH$_2$Cl$_2$/MeOH, 9/1) showed that conversion to the thioamide was complete. For isolation, the pyridine was substantially removed by distillation under reduced pressure, and the residue was taken up in 250 ml of ethyl acetate and washed with brine, 5% strength citric acid and NaHCO$_3$ solutions. Drying and removal of the solvent by distillation resulted in 2.3 g of amorphous thioamide.

The thioamide was dissolved in 40 ml of acetone and, after addition of 4 ml of methyl iodide, left to stand at RT for 6 h. The solvent was stripped off and then the amorphous residue was stirred with dry ether and subsequently dried. The methyl S-methylthioimidate hydroiodide was dissolved in 50 ml of ethanol, 15 ml of 10% strength ammonium acetate solution were added and the mixture was heated at 60° C. for 3 h. For isolation, the solvent was stripped off, the residue was dissolved in 100 ml of CH$_2$Cl$_2$, the insoluble constituents were filtered off and then the CH$_2$Cl$_2$ was distilled off. Digestion with an ethyl acetate/diethyl ether mixture removed the impurities soluble therein. The remaining mixed iodide/acetate salt was dissolved in acetone/water (3/2) and converted into the pure acetate using IRA acetate ion exchanger and subsequently purified by column chromatography (eluent: methylene chloride/methanol/50% strength acetic acid 40/10/1.5). The pure fractions were freeze-dried after removal of the eluent. 1.1 g of white powder remained, melting point 185–187° C., FAB-MS: 394 (M+).

EXAMPLE 2

(D)-2-Cyclohexyl-2-hydroxyacetylproline 6-amidino-3-picolylamide:

(a) (D)-2-Cyclohexyl-2-hydroxyacetylproline 6-cyano-3-picolylamide:

2.25 g of isobutyl chloroformate were added dropwise to a solution of 4.4 g (13 mmol) of O-tetrahydropyranyl-(D)-2-cyclohexyl-2-hydroxyacetylproline (WO 93/18060) and 1.6 g of N-methylmorpholine in 25 ml of DMF at −15° C. After 10 min, a solution of 2.2 g (13 mmol) of 2-cyano-5-(aminomethyl)-pyridine hydrochloride (WO 95/35309) in 20 ml of DMF and 70 ml of $CH_2Cl_2$ and 3.5 g of triethylamine were added dropwise, and the reaction mixture was then stirred for 1 h, during which the temperature rose from −15° C. to 0° C.

Addition of 150 ml of water was followed by extraction several times with ethyl acetate, an the ethyl acetate phase was washed with water, 5% strength $NaHCO_3$ and 5% strength citric acid solutions and dried over $Na_2SO_4$, and the ethyl acetate was distilled off. The remaining oily residue was dissolved in methanol, adjusted to pH 2 with p-toluenesulfonic acid and left to stand at RT for 6 h.

The residue after removal of the methanol by distillation was taken up in ethyl acetate, washed with water, 5% strength citric acid and $NaHCO_3$ solution and dried over $Na_2SO_4$. The residue obtained after removal of the solvent by distillation was purified by column chromatography (eluent: methylene chloride/acetone/methanol 45/5/2). 3.0 g (62% of theory) of white amorphous powder were isolated; FAB-MS (M+H$^+$): 371.

(b) (D)-2-Cyclohexyl-2-hydroxyacetylproline 6-amidino-3-picolylamide acetate:

The compound was prepared as in Example 1 from 2.55 g of (D)-2-cyclohexyl-2-hydroxyacetylproline 6-cyano-3-picolylamide acetate. 0.99 g of (D)-2-cyclohexyl-2-hydroxyacetylproline 6-amidino-3-picolylamide acetate was obtained as a white amorphous powder; FAB-MS (M+H$^+$): 388

EXAMPLE 3

(D)-2-Cyclohexyl-2-hydroxyacetylproline p-amidinobenzylamide acetate:

(a) (D)-2-Cyclohexyl-2-hydroxyacetylproline p-cyanobenzylamide:

4.9 g (20.4 mmol) of (D)-2-cyclohexyl-2-tetrahydropyranyloxyacetic acid (WO 93/18060) were dissolved in 30 ml of DMF, and 5.4 g (20.4 mmol) of N-(p-cyanobenzyl)prolinamide, 3.3 g (20.4 mmol) of N-hydroxybenzotriazole, 3.0 g of DIPEA and 4.33 g (20.6 mmol) of dicyclohexylcarbodiimide were successively added. The mixture was stirred at RT for 48 h. The precipitated urea was filtered off with suction and then the solvent was substantially removed under reduced pressure, 50 ml of water were added to the residue, and extraction was carried out with ethyl acetate. After washing with water and $NaHCO_3$ solution and drying over $Na_2SO_4$, the ethyl acetate was distilled off, and the remaining oily residue was dissolved in methanol and adjusted to pH 2 with p-toluenesulfonic acid. This solution was left to stand at RT for 6 h. The methanol was then distilled off, the residue was taken up in ethyl acetate, and the solution was washed with water, 5% strength citric acid and $NaHCO_3$ solution. The residue obtained after drying over $Na_2SO_4$ and removal of the solvent by distillation was purified by column chromatography (eluent: methylene chloride/acetone/methanol, 45/5/2). 2.5 g of white amorphous powder were obtained; FAB-MS (M+H$^+$): 370.

(b) (D)-2-Cyclohexyl-2-hydroxyacetylproline p-amidinobenzylamide acetate:

Amidine formation took place as in Example 1b. Freeze-drying resulted in white crystals of the acetate. Melting point 216–218° C.; FAB-MS (M+H$^+$): 387.

EXAMPLE 4

(D)-2-Cyclohexyl-2-hydroxyacetylproline 2-methoxy-4-amidinobenzylamide acetate:

was obtained as in Example 3 by reacting (D)-2-cyclohexyl-2-tetrahydropyranyloxyacetic acid with N-(4-cyano-2-methoxybenzyl)prolinamide (WO 95/35309) as white amorphous powder; FAB-MS (M+H$^+$): 417.

EXAMPLE 5

(D)-2-Cyclohexyl-2-hydroxyacetylazetidine-2-carboxylic acid 4-amidinobenzylamide:

(a) Methyl (D)-2-cyclohexyl-2-tetrahydropyranyloxyacetyl-azetidine-2-carboxylate:

2.0 ml (16.2 mmol) of pivaloyl chloride were added dropwise to a solution of 3.92 g (16.2 mmol) of (D)-2-cyclohexyl-2-tetrahydropyranyloxyacetic acid and 2.26 ml (16.2 mmol) of triethylamine in 25 ml of toluene and 5 ml of DMF while cooling in ice and, after stirring for 30 min, a mixture of 2.5 g (16.2 mmol) of methyl azetidine-2-carboxylate hydrochloride and 2.26 ml (16 mmol) of triethylamine in 25 ml of DMF was added dropwise. The mixture was stirred overnight, during which the temperature rose to RT, and was diluted with water and extracted several times with toluene. After the combined toluene phases had been washed with 5% strength $KHSO_4$, 10% strength $Na_2CO_3$ and sodium chloride solutions, the solvent was removed by distillation and the remaining pale yellow oil was hydrolyzed without further purification.

(b) (D)-2-Cyclohexyl-2-tetrahydropyranyloxyacetylazetidine-2-carboxylic acid:

The methyl ester (stage a) was dissolved in 50 ml of THF, a solution of 5 g of LiOH in 50 ml of water was added, and the mixture was stirred at RT overnight. After removal of the THF by distillation, the aqueous phase was acidified with $KHSO_4$ solution and extracted several times with ethyl acetate. The combined ethyl acetate phases were washed with brine, dried over $Na_2SO_4$ and then evaporated to dryness. 4.1 g (78% of theory) of white crystals were isolated; FAB-MS (M+H$^+$): 326.

(c) (D)-2-Cyclohexyl-2-hydroxyacetylazetidine-2-carboxylic acid p-cyanobenzylamide:

8.12 g of diisopropylethylamine, and then 11 ml (15 mmol) of propanephosphonic anhydride (50% strength solution in ethyl acetate), were added dropwise to a suspension of 2.1 g (12.5 mmol) of p-cyanobanzylamine hydrochloride and 4.1 g (12.5 mmol) of the carboxylic acid isolated in stage (b) in 70 ml of $CH_2CH_2$ at −5° C. The mixture was stirred for 2 h, allowing the temperature to rise to 20° C. The organic phase was washed with water, 5% strength $NaHCO_3$ and 5% strength citric acid solutions, dried over $Na_2SO_4$ and evaporated to dryness.

The remaining oily residue was dissolved in methanol, adjusted to pH 2 with p-toluenesulfonic acid and left to stand at RT for 6 h. The methanol was then distilled off, and the residue was taken up in ethyl acetate and washed with water, 5% strength citric acid and NaHCO$_3$ solutions. The residue obtained after drying over Na$_2$SO$_4$ and removal of the solvent by distillation was purified by column chromatography (eluent: methylene chloride/acetone/methanol 45/5/2. 3.7 g (82%) of white amorphous powder were isolated; FAB-MS (M+H$^+$): 357.

(d) (D)-2-Cyclohexyl-2-hydroxyacetylazetidine-2-carboxylic acid p-amidinobenzylamide acetate:

Amidine formation took place as in Example 1b. Freeze-drying resulted in a white amorphous powder of the acetate; FAB-MS: (M+H$^+$) 374.

EXAMPLE 6

(D,L)-2-(1,2,3,4-Tetrahydro-1-naphthyl)-2-hydroxyacetyl-proline 6-amidino-3-picolylamide:

(a) Methyl (1,2,3,4-tetrahydro-1-naphthyl)glycolate:

4.12 g (20 mmol) of 1,2,3,4-tetrahydro-1-naphthylglycolic acid (Chem. Ber. 117 (1984) 332–325) were dissolved in 30 ml of dry methanol, 4 drops of conc. H$_2$SO$_4$ were added and the mixture was refluxed for 3 h. The methanol was distilled out under reduced pressure at RT, and the residue was taken up in CH$_2$Cl$_2$ and washed with NaHCO$_3$ solution and water until neutral. After drying over Na$_2$SO$_4$ and removal of the solvent by distillation, the methyl ester was obtained as a colorless oil in quantitative yield.

(b) O-Tetrahydropyranyl-1,2,3,4-tetrahydro-1-naphthylglycolic acid:

The above methyl ester was dissolved in 20 ml of CH$_2$Cl$_2$ and, while stirring, 2 ml (22 mmol) of dihydropyran and 0.3 ml of 10% strength hydrochloric acid solution in ethyl acetate were added dropwise. After standing overnight, the mixture was diluted with methylene chloride and washed with NaHCO$_3$solution and water until neutral, and the solvent was removed by distillation at RT.

The residue was dissolved in 40 ml of methanol, 20 ml of 1 N LiOH solution were added, the mixture was left to stand at RT overnight and then the methanol was substantially removed by distillation at RT. The slightly cloudy solution was extracted with CH$_2$Cl$_2$, adjusted to pH 3 with 1 M KHSO$_4$ solution while cooling, and extracted several times with CH$_2$Cl$_2$. The combined CH$_2$Cl$_2$ extracts were washed with water, dried over Na$_2$SO$_4$ and distilled at RT. The oily residue was reacted immediately in the next stage.

(c) N-(6-Cyano-3-picolyl)prolinamide:

25.3 g (0.15 mmol) of 2-cyano-5-aminomethylpyridine hydrochloride ((WO 95/35309) were added to a solution of 32.5 g (0.15 mol) of Boc-Pro-OH in 500 ml of CH$_2$Cl$_2$. A clear solution was obtained by adding 97 g (0.75 mol) of diisopropylethylamine at −5° C., and then 150 ml of a 50% strength solution of propanephosphonic anhydride in ethyl acetate were added dropwise. The mixture was stirred for 2 h, during which the temperature rose to 20° C. The organic phase was washed with water, 5% strength NaHCO$_3$ and 5% strength citric acid solutions, dried over Na$_2$SO$_4$ and evaporated to dryness. 40 g (81%) of colorless oil remained. 36 g (0.11 mol) were dissolved in 400 ml of isopropanol and, at RT, a solution of 20 g of HCl in 150 ml of isopropanol was added. The solution was heated at 50° C. for 5 h, during which a white precipitate separated out and this, after cooling, was filtered off with suction and washed until free of acid with cold isopropanol and finally with diisopropyl ether. 19.8 g of hydrochloride were isolated, melting point 226–228° C. (decomposition); TLC: CH$_2$Cl$_2$/MeOH/50% strength acetic acid, 85/15/2.

(d) The compound of stages b and c were coupled as in Example 3a and converted into the amidine by method 1b. The acetate was obtained as a white amorphous powder; FAB-MS (M+H$^+$): 436.

EXAMPLE 7

(D,L)-2-(1,2,3,4-Tetrahydro-1-naphthyl)-2-hydroxyacetyl-proline 4-amidinobenzylamide:

The compound was prepared as in Example 6 by coupling O-tetrahydropyranyl-1,2,3,4-tetrahydro-1-naphthylprolinamide hydrochloride (WO 95/35309), subsequent elimination of protective groups and conversion to the amidine. The acetate was in the form of a white amorphous powder after freeze-drying; FAB-MS (M+H$^+$): 435.

EXAMPLE 8

(D)-2-Cyclohexyl-2-acetoxyacetylproline 6-amidino-3-picolylamide:

(a) (D)-2-Cyclohexyl-2-acetoxyacetylproline 6-cyano-3-picolylamide:

3.7 g (10 mmol) of (D)-2-cyclohexyl-2-hydroxacetylproline 6-cyano-3-picolylamide (see Example 1a for preparation), 1.5 g (15 mmol) of triethylamine and 30 mg of DMAP were dissolved in 30 ml of CH$_2$Cl$_2$ and, while cooling, 1.1 g (11 mmol) of acetic anhydride were added. The reaction mixture was left to stand at RT overnight and then washed with water, 5% strength citric acid and 5% strength NaHCO$_3$ solutions, dried over Na$_2$SO$_4$ and evaporated to dryness. The remaining residue was used without further purification for the next reaction; FAB-MS (M+H$^+$): 413.

(b) Amidine formation

Amidine formation took place as in Example 1b. The acetate was isolated after freeze-drying in the form of a white amorphous powder; FAB-MS (M+H$^+$): 430.

EXAMPLE 9

(D)-2-Cyclohexyl-2-acetoxyacetylproline 4-amidinobenzylamide:

The compound was isolated as in Example 8 by reacting (D)-2-cyclohexyl-2-acetoxyacetylproline 6-cyano-3-picolylamide (stage 8a) with N-(4-cyanobenzyl)prolinamide hydrochloride (WO 95/35309) and subsequent amidation as a white amorphous acetate; FAB-MS (M+H$^+$): 429.

EXAMPLE 10

(D)-2-Cyclohexyl-2-hexanoyloxyacetylproline 4-amidinobenzylamide:

The compound was obtained as in Example 8 by reacting (D)-2-cyclohexyl-2-hydroxyacetylproline p-cyanobenzylamide with hexanoyl chloride followed by amidation. Acetate: white amorphous powder; FAB-MS (M+H$^+$): 468.

EXAMPLE 11

O-Hydroxycarbonylmethyl-(D)-2-cylohexyl-2-hydroxyacetylproline 6-amidino-3-picolylamide:

(a) Methyl O-t-butoxycarbonylmethyl-(D)-2-cyclohexyl-2-hydroxyacetate:

1.7 g of methyl (D)-2-cyclohexyl-2-hydroxyacetate (WO 93/18060) were added to a stirred suspension, free of mineral oil, of 480 mg of NaH (55% dispersion in mineral oil, 10 mmol) in 20 ml of DMF.

After evolution of gas had ceased, a solution of 1.95 g (10 mmol) of t-butyl bromoacetate in 2 ml of DMF was added dropwise, and the mixture was stirred overnight.

The reaction product was poured into water and extracted several times with ether, the combined ether extracts were washed with water and dried over $Na_2SO_4$, and the ether was distilled off. The remaining oily residue was purified by column chromatography (ether/n-hexane 1/1) yield: 80%.

(b) O-t-Butoxycarbonylmethyl-(D)-2-cyclohexyl-2-hydroxyacetic acid:

The ester was hydrolyzed with 1 N LiOH as in Example 6b. The crude acid was used immediately in the subsequent coupling.

(c) O-t-Butoxycarbonylmethyl-(D)-2-cyclohexyl-2-hydroxyacetylproline 6-cyano-3-picolylamide:

The above acid was coupled as in Example 2a with N-(6-cyano-3-picolyl)prolinamide hydrochloride (stage 6c). White amorphous powder; FAB-MS (M+H$^+$): 485.

(d) O-t-Butoxycarbonylmethyl-(D)-2-cyclohexyl-2-hydroxyacetylproline 6-amidino-3-picolylamide acetate:

Conversion into the amidine took place as in 1b. White amorphous powder; FAB-MS (M+H$^+$): 502.

(e) O-Hydroxycarbonylmethyl-(D)-2-cyclohexyl-2-hydroxyacetylproline 6-amidino-3-picolylamide:

The above t-butyl ester was dissolved in trifluoroacetic acid and left to stand at RT overnight. The trifluoroacetic acid was removed by distillation under reduced pressure at 20° C. finally with addition of toluene, and the residue was treated with ether, resulting in a white crystalline powder. This was converted by chromatography on silica gel with a methanol/conc. $NH_3$ eluent (50/2) to the free betaine which, after the eluent had been stripped off, was freeze-dried. White amorphous powder; FAB-MS (M+H$^+$): 446.

EXAMPLE 12

3-Cyclohexyl-(D)-lactylproline 6-amidino-3-picolylamide:

The compound was obtained by reacting O-tetrahydropyranyl-3-cyclohexyl-(D)-lactic acid (WO 93/18060) with N-(6-cyano-3-picolyl)prolinamide (Example 6c) as in Example 3a, followed by amidine formation as in 1b. White amorphous powder; FAB-MS (M+H$^+$): 402.

EXAMPLE 13

3-Cyclohexyl-(D)-lactylproline 4-amidinobenzylamide acetate:

(a) 3-Cyclohexyl-(D)-lactylproline 4-cyanobenzylamide:

2.25 g of isobutyl chloroformate were added dropwise to a solution of 3.3 g (13 mmol) of O-tetrahydropyranyl-3-cyclohexyl-(D)-lactic acid (WO 93/18060) and 1.6 g of N-methylmorpholine in 25 ml of DMF at −15° C. After 10 min, a solution of 3.5 g (13 mmol) of N-(4-cyanobenzyl) prolinamide hydrochloride in 20 ml of DMF and 70 ml of $CH_2Cl_2$ and 3.5 g of triethylamine were added dropwise. The reaction mixture was then stirred for 1 h, during which the temperature rose from −20° C. to 0° C., and subsequently poured into 100 ml of water. Further workup took place as in 1a. Purification by column chromatography resulted in isolation of 2.7 g of white powder which melted at 122° C. after crystallization from an ether/hexane mixture.

(b) Conversion into the amidine took place as in 1b. The acetate melted at 136–140° C.; (FAB-MS (M+H$^+$): 401.

EXAMPLE 14

3-Cyclohexyl-(D)-lactylproline 2-methoxy-4-amidinobenzylamide:

As in Example 1, O-tetrahydropyranyl-3-cyclohexyl-(D)-lactylproline was reacted with 4-aminomethyl-3-methoxybenzonitrile (WO 95/35309) and subsequently converted into the amidine. The acetate was isolated as a white amorphous powder after freeze-drying; FAB-MS (M+H$^+$): 431.

EXAMPLE 15

3,3-Diphenyl-(D,L)-lactylproline 6-amidino-3-picolylamide:

As in Example 1, O-tetrahydropyranyl-3,3-diphenyl-(D, L)-lactylproline was reacted with 2-cyano-5-aminomethyl) pyridine hydrochloride (WO 95/35309) and subsequently converted into the amidine. Acetate: white amorphous powder, FAB-MS (M+H$^+$): 472.

EXAMPLE 16

3,3-Diphenyl-(D,L)-lactylproline 4-amidinobenzylamide acetate:

As in Example 1, O-tetrahydropyranyl-3,3-diphenyl-(D, L)-lactylproline was reacted with p-cyanobenzylamine and subsequently converted into the amidine. The mixture of diastereomeric acetates melted at 99–106° C.; FAB-MS (M+H$^+$): 471.

EXAMPLE 17

(D)-Cyclohexylalanylproline 6-amidino-3-picolylamide:

(a) Boc-(D)-Cha-Pro-OH 30.7 g (0.113 mol) of Boc-(D)-Cha-OH and 18.7 g (0.113 mol) of H-Pro-OCH$_3$ HCl were suspended in 300 ml of $CH_2Cl_2$ and dissolved by dropwise addition of 58.3 g (0.45 mol) of diisopropylethylamine. After cooling to −15° C., 113 ml (0.147 mol) of propanephosphonic anhydride (50% strength solution in ethyl acetate) were added dropwise, and the mixture was stirred at RT for 1 hour.

After addition of 200 ml of water, the organic phase was separated off and washed with aqueous $K_2CO_3$ solution, 0.5 N hydrochloric acid and 5% strength $NaHCO_3$ solution. After drying with $Na_2SO_4$, the solvent was distilled off, and the oily residue (42 g) was dissolved in 400 ml of ethanol, mixed with 120 ml of 1 N NaOH and stirred at RT for 2 h.

The alcohol was distilled off and then the aqueous phase was diluted with water and extracted several times with methyl tert-butyl ether. The aqueous phase was acidified with $KHSO_4$ solution and extracted 3× with $CH_2Cl_2$. After drying and removal of the methylene chloride by distillation, the oily residue was crystallized from diisopropyl ether/n-hexane (1/3). 29 g of white crystals were isolated.

(b) Boc-(D)-Cha-Pro-NH-3-(6-CN)-pico:

27.6 g (0.075 mol) of Boc-(D)-Cha-Pro-OH and 12.7 g (0.075 mol) of 6-cyano-3-picolylamine hydrochloride were suspended in 300 ml of $CH_2Cl_2$, and 47 g (0.364 mol) of diisopropylethylamine were added. Then, at −10° C., 66 ml of propanephosphonic anhydride (50% strength solution in ethyl acetate) were added dropwise, the mixture was stirred at RT for 1 hour, 200 ml of water were added, and the $CH_2Cl_2$ phase was separated off. The organic phase was washed with 0.1 N sodium hydroxide solution and water and then dried, and the solvent was distilled off. The residue was taken up in 100 ml of ethyl acetate, whereupon crystallization rapidly started and was completed by adding 150 ml of n-hexane. Filtration with suction and drying resulted in 32.4 g (89% of theory) of white crystals being isolated.

(c) Boc-(D)-Cha-Pro-NH-3-(6-am)-pico:

1.15 g (16.5 mmol) of hydroxylamine hydrochloride were suspended in 5 ml of ethanol, 1.2 g of 25% strength ammonia solution were added and the mixture was stirred for 10 min. The salt which precipitated after addition of 45 ml of ethanol was filtered off with suction, and 3.18 g (6.6 mmol) of the above compound (stage c) were added to the solution. The hydroxyamidine compound separated out after a short time and, after stirring for 30 min, was filtered off with suction and washed with a little cold water and ethanol. The residue moist with ethanol was dissolved in 40 ml of ethanol and 8 ml of glacial acetic acid, 250 mg of 10% Pd/C were added and hydrogenation was carried out at about 50° C. After 5 h, TLC ($CH_2Cl_2$/MeOH/50% strength acetic acid, 20/5/1) showed no detectable starting material.

The catalyst was removed by filtration with suction through a Celite layer and then the solvent was removed by distillation, adding toluene towards the end. Addition of 50 ml of acetone was followed by crystallization of the amidine acetate, and it was filtered off. White crystals, FAB-MS ($M+H^+$): 501.

(d) H-(D)-Cha-Pro-NH-3-(6-am)-pico:

The Boc group was eliminated from compound c) under standard conditions. Dihydrochloride: white crystals, FAB-MS ($M+H^+$): 401.

EXAMPLE 18

(D)-Cyclohexylglycylazetidine-2-carboxylic acid 6-amidino-3-picolylamide:

By a method similar to that described above, Boc-(D)-cyclohexylglycine was coupled to methyl azetidine-2-carboxylate hydrochloride, hydrolyzed with LiOH to the free dipeptide acid and again coupled with 6-cyano-3-picolylamine hydrochloride. Addition of hydroxylamine onto the cyano group, catalytic hydrogenation of the N-hydroxyamidine with Raney nickel or Pd/C in dioxane/HCl or $CF_3COOH/CH_2Cl_2$ led to the title compound. The dihydrochloride was obtained as white powder; FAB-MS ($M+H^+$): 373.

EXAMPLE 19

(D)-Cyclohexylglycylpiperidine-2-carboxylic acid 6-amidino-3-picolylamide:

The required product was obtained by the above procedure starting from Boc-(D)-cyclohexylglycine and methyl (L)-piperidine-2-carboxylate hydrochloride. Acetate: white amorphous powder; FAB-MS $(M+H)^+$: 401.

EXAMPLE 20

H-(D)-(O-tert-butyl)serylproline 6-amidino-3-picolylamide:

As in Example 17, Z-Ser(tBu)-OH was coupled with H-Pro-$OCH_3$·HCl to give the dipeptide Z-Ser(tBu)-Pro-$OCH_3$, the ester was hydrolyzed, coupling was carried out with 6-cyano-3-picolylamine dihydrochloride to give Z-Ser(tBu-Pro-NH-3-(6-CN)-pico, and the cyano group was converted via the hydroxyamidine stage into the amidine. This hydrogenation simultaneously eliminated the Z protective group.

H-(D)-Ser(tBu)-Pro-NH-3-(6-am)-pico dihydrochloride was obtained as white amorphous powder. FAB-MS $(M+H)^+$: 391.

EXAMPLE 21

(D)-Cyclohexylglycylhydroxyproline 6-amidino-3-picolylamide:

(a) 2.5 g of Fmoc-Hyp(tBu)-OH, 0.9 g of 3-aminomethyl-6-cyanopyridine dihydrochloride and 4.7 ml of DIPEA were introduced into 20 ml of DCM at 0° C. Then 5 ml of PPA (50% strength in ethyl acetate) were added and the reaction mixture was stirred at 0° C. for 1 h. Then the temperature was allowed to rise to RT over the course of 18 h. For workup, the reaction mixture was diluted with 100 ml of ethyl acetate, and the organic phase was extracted 5× with aqueous $NaHSO_4$ solution (20% strength), 5× with saturated $NaHCO_3$ solution and 1× with NaCl solution. The organic phase was dried and concentrated under reduced pressure. 2.2 g of the crude product remained and were used without further purification in the next reaction.

(b) 2.2 g of Fmoc-Hyp(tBu)-NH-3-(6-CN)-pico were dissolved in 38.8 ml of DMF and 4.2 ml of diethylamine and left to stand at RT for 2 h. The solution was then concentrated under reduced pressure. The crude product H-Hyp(tBu)-NH-3-(6-CN)-pico (1.3 g) was used without further workup in the next reaction.

(c) 1.3 g of H-Hyp(tBu)-NH-3-(6-CN)-pico were introduced together with 3.9 ml of DIPEA and 1 g of Boc-(D)-Chg-OH into 20 ml of methylene chloride at 0° C. Then 4 ml of PPA (50% strength in ethyl acetate) were added and the reaction mixture was stirred at 0° C. for 1 h. Then the temperature was allowed to rise to RT over the course of 18 h. For workup, the reaction mixture was diluted with 100 ml of ethyl acetate, and the organic phase was extracted 5× with aqueous $NaHSO_4$ solution (20% strength), 5× with saturated $NaHCO_3$ solution and 1× with NaCl solution. The organic phase was dried and concentrated under reduced pressure. 2.4 g of the crude product Boc-(D)-Chg-Hyp(tBu)-NH-3-(6-CN)-pico remained and were used without further purification in the next reaction.

(d) 2.4 g of the crude product were dissolved in 14 ml of pyridine and 6.4 ml of triethylamine. Then $H_2S$ was passed into the solution for 30 min. The solution was left to stand at RT for 18 h. The reaction mixture was then added to 1 l of 5% strength citric acid, and the precipitated product was filtered off. The aqueous phase was then extracted 2× with methylene chloride. The filtered product was dissolved in methylene chloride and combined with the organic extraction phases. The combined product phases were then extracted 1× with 20% strength aqueous $NaHSO_4$ solution and 1× with 1 N HCl and dried. The organic phase was concentrated under reduced pressure. The residue of crude thioamide was dissolved in 14 ml of acetone and, after addition of 2.4 ml of iodomethane, stirred at RT for 18 h. The reaction mixture was then concentrated in a rotary evaporator. The residue was dissolved in 5.5 ml of anhydrous MeOH and, after addition of 5.5 ml of a methanolic $NH_4OAc$ solution, stirred at RT for 18 h. For work-up, the reaction mixture was concentrated under reduced pressure and taken up in methylene chloride, and the organic phase was washed with water. The organic phase was dried with magnesium sulfate and then the solvent was removed under reduced pressure. The residue was dissolved in a little MeOH and then precipitated in diisopropyl ether. The precipitated product was filtered off.

(e) To remove the protective groups, the product was stirred in dioxane/HCl at RT for 18 h, the reaction mixture was concentrated under reduced pressure, and the remaining product was taken up in water and lyophilized. 63 mg remained. FAB-MS ($M^+$): 460.

EXAMPLE 22

H-(D,L)-Cycloheptylalanylproline 6-amidino-3-picolylamide:

As in Example 17, Boc-(D,L)-Chea-OH (see above for preparation) was coupled with H-Pro-$OCH_3$·HCl to give the dipeptide Boc-(D,L)-Chea-Pro-$OCH_3$, the ester was hydrolyzed, coupling was carried out with 6-cyano-3-picolylamine dihydrochloride to give Boc-(D,L)-Chea-Pro- NH-3-(6-CN)-pico, and the cyano group was converted via the hydroxyamidine stage into the amidine. The Boc protective group was eliminated with HCl.

H-(D,L)-Chea-Pro-NH-3-(6-am)-pico dihydrochloride was obtained as white powder. FAB-MS (M+H)$^+$: 415

EXAMPLE 23

(D)-(α-Methyl)cyclohexylalanylproline 6-amidino-3-picolylamide:

(a) H-Pro 6-carbamoyl-3-picolylamide:

100 ml of diisopropylethylamine and 30 g (133.8 mmol) of 6-carbamoyl-3-picolylamine dihydrochloride (se the preparation of the precursors in Example 10) were added to 28.8 g (133.8 mmol) of Boc-Pro—OH in 300 ml of DCM at −5° C. Then 100 ml of PPA (50% strength ethyl acetate solution) in 100 ml of DCM were added dropwise at −5° C. over the course of 1 h, and the mixture was stirred at 0° C. for a further 2 h. The mixture was washed with 0.5 N sodium hydroxide solution, with KHSO$_4$ solution and then with water, and the organic phase was dried over Na$_2$SO$_4$. The solvent was stripped off to result in 44.4 g of Boc-Pro 6-carbamoyl-3-picolylamide.

30 g of the Boc-protected compound (86 mmol) were dissolved in 370 ml of isopropanol, and the protective group was cleaved by adding 430 mmol of HCl (isopropanolic HCl) at 50° C. 28 g of H-Pro 6-carbamoyl-3-picolylamide hydrochloride were obtained.

$^1$H-NMR (DMSO-d$^6$, δ in ppm): 10.35 (m,1H); 9.65 (t,1H); 8.70–8.55 (2H); 8.38 (1H); 8.20 (1H); 8.10 (1H); 7.88 (1H); 4.50 (d,2H); 4.30 (m,1H); 3.30–3.10 (2H); 2.37 (m,1H); 2.00–1.80(3H).

(b) (D)-(α-Methyl)cyclohexylalanylproline (6-amidino)-3-picolylamide:

5.00 g of diisopropylethylamine and then 6.7 ml (9.2 mmol) of PPA (50% strength solution in ethyl acetate) were added dropwise to a solution of 2.20 g (7.7 mmol) of Boc-(D)-(α-methyl)-Cha—OH and 2.19 g (7.7 mmol) of H-Pro 6-carbamoyl-3-picolylamide hydrochloride in 60 ml of DCM at −5° C. The mixture was stirred for 2 h, during which the temperature rose from −5° C. to 20° C. The organic phase was washed with 5% strength NaHCO$_3$, 50% strength citric acid solution and water, dried over Na$_2$SO$_4$ and evaporated to dryness. 2.98 g of Boc-(D)-(α-methyl)-Cha-Pro 6-carbamoyl-3-picolylamide were obtained.

2.9 g (5.6 mmol) of carbamoyl derivative were reacted in 50 ml of DCM and 2.4 ml of diisopropylethylamine at 0° C. with 0.9 ml of trifluoroacetic anhydride to give the corresponding nitrile. After 2 h, the solvent was stripped off, leaving 2.7 g of solid. This was stirred in 50 ml of DCM/MeOH 1:1 with 375 mg (5.4 mmol) of hydroxylamine hydrochloride and 3.7 ml of diisopropylethylamine at 40° C. for 5 h. The solvent was stripped off, the resulting hydroxyamidine derivative was taken up in DCM, and the organic phase was washed and dried over strength sodium bicarbonate solution and water and dried over Na$_2$SO$_4$. The solvent was stripped off to result in 2.61 g of solid, which was hydrogenated win 50 ml of MeOH and one mole equivalent of acetic acid with 200 mg of Raney nickel until the theoretically required amount of hydrogen had been taken up. The temperature was generally kept at from 20° C. to 40° C. during this. The catalyst was then filtered off, and the solvent was removed in a rotary evaporator.

The product was purified by column chromatography on silica gel (mobile phase: DCM/20% MeOH/3.5% HOAc (50% strength)) to result in 1.53 g of Boc-(D)-(α-methyl)-Cha-Pro 6-amidino-3-picolylamide hydroacetate (HPLC purity: 96.8%); FAB-MS (M+H)$^+$: 515.

The Boc protective group was eliminated in isopropanolic HCl (5 equivalents of HCl) at 50° C. 1.41 mg of H-(D)-(α-methyl)-Cha-Pro 6-amidino-3-picolylamide dihydrochloride were obtained; FAB-MS (M+H$^+$): 415.

EXAMPLE 24

(D,L)-(4-Tetrahydropyranyl)glycylproline 6-amidino-3-picolylamide:

As in Example 23, 270 g (10.4 mmol) of H-(D,L)-Thpg—OH and 2.96 g (10.4 mmol) of H-Pro 6-carbamoyl-3-picolylamide hydrochloride resulted in 1.60 g of Boc-(D,L)-Thpg-Pro 6-amidino-3-picolylamide hydroacetate (HPLC purity: 95%); FAB-MS (M+H$^+$): 489. Cleavage of the Boc protective group resulted in 1.33 g of H-(D,L)-Thpg-Pro 6-amidino-3-picolylamide dihydrochloride; FAB-MS (M+H$^+$): 389.

EXAMPLE 25

(D,L)-2-Norbornylglycylproline 6-amidino-3-picolylamide:

As in Example 17, Boc-(D,L)-(2-norbornyl)Gly—OH (see above for preparation) was coupled with H-Pro—OCH$_3$.HCl to give the dipeptide Boc-(D,L)-(2-norbornyl) Gly-Pro—OCH$_3$, the ester was hydrolyzed, coupling was carried out with 6-cyano-3-picolylamine dihydrochloride to give Boc-(D,L)-(2-norbornyl)Gly-Pro—NH—3-(6—CN)-pico, and the cyano group was converted via the hydroxyamidine stage into the amidine. Elimination of the Boc protective group with HCl resulted in H-(D,L)-(2-norbornyl) Gly-Pro—NH-3-(6-am)-pico dihydrochloride as white amorphous powder. FAB-MS (M+H$^+$): 399.

EXAMPLE 26

(D,L)-1-Adamantylglycylproline 6-amidino-3-picolylamide:

As in Example 17, Boc-(D,L)-(1-adamantyl)Gly—OH (see above for preparation) was coupled with H-Pro—OCH$_3$.HCl to give the dipeptide Boc-(D,L)-(1-adamantyl) Gly-Pro—OCH$_3$, the ester was hydrolyzed, coupling was carried out with 6-cyano-3-picolylamine dihydrochloride to give Boc-(D,L)-(1-adamantyl)Gly-Pro—NH—3-(6-CN)-pico, and the cyano group was converted via the hydroxyamidine stage into the amidine. Elimination of the Boc protective group with HCl resulted in H-(D,L)-(1-adamantyl)Gly-Pro—NH—3-(6-am)-pico dihydrochloride as white amorphous powder. FAB-MS (M+H$^+$): 439.

EXAMPLE 27

H-(D,L)-1-Tetralinylglycylproline 6-amidino-3-picolylamide:

As in Example 17, Boc-(D,L)-(1-tetralinyl)Gly—OH (see above for preparation) was coupled with H-Pro—OCH$_3$.HCl to give the dipeptide Boc-(D,L)-(1-tetralinyl)Gly-Pro—OCH$_3$, the ester was hydrolyzed, coupling was carried out with 6-cyano-3-picolylamine dihydrochloride to give Boc-(D,L)-(1-tetralinyl)Gly-Pro—NH—-3-(6-CN)-pico, and the cyano group was converted via the hydroxyamidine stage into the amidine. Elimination of the Boc protective group with HCl resulted in H-(D,L)-(1-tetralinyl)Gly-Pro—NH—3-(6-am)-pico dihydrochloride as white solid substance. FAB-MS (M+H$^+$): 435.

EXAMPLE 28
(D,L)-(Trimethylsilyl)alanylproline 6-amidino-3-picolylamide:

As in Example 23, 1.88 g (7.2 mmol) of Boc-(D,L)-triethylsilyl)Ala—OH and 2.05 g (7.2 mmol) of H-Pro 6-carbamoyl-3-picolylamide hydrochloride resulted in 1.45 g of Boc-(D,L)-trimethylsilyl)Ala-Pro 6-amidino-3-picolylamide hydroacetate as 1:1 mixture of diastereomers with a purity of 96% (HPLC); FAB-MS (M+H$^+$): 491.

Cleavage of the Boc protective group resulted in 1.22 g of H-(D,L)-(trimethylsilyl)Ala-Pro 6-amidino-3-picolylamide dihydrochloride; FAB-MS (M+H$^+$): 391.

EXAMPLE 29
(D,L)-(3,4,5-Trimethoxy)phenylalanylproline 6-amidino-3-picolylamide:

As in Example 17, Boc-(D,L)-(3,4,5-trimethoxy)Phe—OH (see above for preparation) and H-Pro-Me.HCl were used to prepared the dipeptide Boc-(D,L)-(3,4,5-trimethoxy)Phe-Pro-oCH$_3$, the ester was hydrolyzed, coupling was carried out with 6-cyano-3-picolylamine dihydrochloride to give Boc-(D,L)-(3,4,5-(OCH$_3$)$_3$)Phe-Pro—NH—3-(6-CN)-pico, and the cyano group was converted via the hydroxyamidine stage into the amidine. The Boc protective group was eliminated with HCl.

H-(D,L)-(3,4,5-trimethoxy)Phe-Pro—NH—3-(6-am)-pico dihydrochloride was obtained as white amorphous powder. FAB-MS (M+H$^+$): 485

EXAMPLE 30
(D,L)-(3-Phenyl)prolylproline 6-amidino-3-picolylamide:

As in Example 23, 1.50 g (5.1 mmol) of Boc-(D,L)-(3-phenyl)Pro—OH (the trans-amino acid described in J. Org. Chem. 55 (1990) 270 was used) and 1.45 g (5.1 mmol) of H-Pro-(6-carbamoyl)-3-picolylamide hydrochloride resulted in 1.01 g of Boc-(D,L)-(3-phenyl)Pro-Pro 6-amidino-3-picolylamide hydroacetate with a purity of 98% (HPLC): FAB-MS (M+H$^+$): 521.

Cleavage of the Boc protective group resulted in 0.92 g of H-(D,L)-(3-phenyl)Pro-Pro 6-amidino-3-picolylamide dihydrochloride; FAB-MS (M+H$^+$): 421.

EXAMPLE 31
(D,L)-(4-Methyl)pipecolylproline 6-amidino-3-picolylamide:

As in Example 23, 1.50 g (6.2 mmol) of trans-(D,L)-(4-methyl)-Pic—OH (literature: Biochem. Biophys. Res. Commun. (1981) 440) and 1.76 g (6.2 mmol) of H-Pro 6-carbamoyl-3-picolylamide hydrochloride resulted in 1.08 g of Boc-(D,L)-(4-methyl)Pic-Pro 6-amidino-3-picolylamide hydroacetate in a purity of 95% (HPLC); FAB-MS (M+H$^+$): 473.

Cleavage of the Boc protective group resulted in 0.90 g of H-(D,L)-(4-methyl)Pic-Pro 6-amidino-3-picolylamide dihydrochloride; FAB-MS (M+H$^+$): 373.

EXAMPLE 32
(D)-Cyclohexylalanyl-3,4-dehydroproline 6-amidino-3-picolylamide:
(a) Boc-Pyr—NH—3-(6—CONH$_2$)-pico:

5.0 g of Boc-Pyr—OH (23.4 mmol) were suspended together with 5.25 g of 6-carbamoyl-3-picolylamine dihydrochloride and 32.1 ml of diisopropylethylamine (187 mmol) in 50 ml of CH$_2$Cl$_3$ and, while stirring at 0–5° C., 23.5 ml of propanephosphonic anhydride (50% strength solution in ethyl acetate) were added dropwise. The mixture was then stirred at RT overnight. The solution was diluted to 150 ml with CH$_2$CL$_2$, extracted successively with 20% strength sodium bisulfate solution and 5% strength citric acid solution until no diisopropylethylamine was detectable by TLC, dried over sodium sulfate and concentrated in a rotary evaporator. The aqueous phases were then back-extracted three times with CH$_2$Cl$_2$, and the organic phase was dried, concentrated in a rotary evaporator and used together with the above product but without further purification in the next reaction. Propanephosphonic acid was also present as subsidiary component.

(b) H-Pyr—NH—3-(6—CONH$_2$)-pico hydrochloride:

The crude product from above was dissolved in 10 ml of CH$_2$Cl$_2$ and after addition of 10 ml of 5 M hydrochloric acid in ether, stirred at RT for 2 h (TLC check). The crude product after complete concentration and codistillation with toluene under reduced pressure was recrystallized from 200 ml of ethanol. This resulted in 5.03 g and, after concentration of the mother liquor, a further 0.3 g of product (80.4% of theory). Elemental analysis showed that the product was in the form of the monohydrochloride.

(c) Boc-(D)-CHa-Pyr—NH—3-(6—CONH$_2$)-pico:

5.06 g of Boc-(D)-Cha—OH (18.66 mmol) were stirred together with 5.28 g of H-Pyr—NH—3-(6—CONH$_2$)-pico hydrochloride (18.66 mmol) and 9.55 ml of diisopropylethylamine (56 mmol) in 75 ml of CH$_2$Cl$_2$ and, at 0–5° C. 18.6 ml of propanephosphonic anhydride (50% strength solution in ethyl acetate) were added dropwise. The mixture was then stirred at RT overnight, during which a precipitate separated out. The precipitate was filtered off with suction and the solution was extracted five times with 25 ml of 5% strength citric acid each time (TLC showed no diisopropylethylamine left in the organic phase) and then washed several times with saturated sodium bicarbonate solution, dried over sodium sulfate and concentrated under reduced pressure. To minimize the propanephosphonic acid byproduct, the residue was taken up in ethyl acetate, extracted several times with saturated NaHCO$_3$ solution and then dried over sodium sulfate and concentrated in a rotary evaporator. Yield 7.0 g of product as solid foam (75% of theory).

(d) Boc-(D)-Cha-Pyr—NH—3-(6—CN)-pico:

7.0 g of Boc-(D)-Cha-Pyr—NH—3-(7—CONH$_2$)-pico (14 mmol) were dissolved together with 9.5 ml of diisopropylethylamine (56 mmol) in 100 ml of CH$_2$Cl$_2$ and cooled to 0–5° C., and 3.5 ml of trifluoroacetic anhydride (25.2 mmol) were added dropwise. After stirring at RT for 2 h, the precursor was completely converted. The solution was then extracted three times with 20% strength sodium sulfate, three times with saturated sodium bicarbonate and once with saturated sodium chloride solution, dried over sodium sulfate and concentrated in a rotary evaporator. Yield: 6.6 g (98% of theory).

(e) H-(D)-Cha-Pyr—NH—3-(6-am)-pico:

The nitrile functionality in Boc-(D)-Cha-Pyr—NH—3-(6—CN)-pico was converted as in Example 93 (c–e) into the thioamide with H$_2$S, into the imino thiomethylester with methyl iodide and subsequently into the amidine with ammonium acetate. The Boc protective group was eliminated with ethereal hydrochloric acid in methylene chloride. FAB-MS (M+H$^+$): 398.

EXAMPLE 33

(D)-Cyclohexylglycol-(N-cyclopropyl)glycine 6-amidino-3-picolylamide:

(a) H-(N-Cyclopropyl)Gly 6-carbamoyl-3-picolylamide:

As in Example 23(a), 12.5 g of Boc-(N-cyclopropyl) Gly—OH (58 mmol) were reacted with 13.0 (58 mmol) of 6-carbamoyl-3-picolylamine dihydrochloride to give 11.3 g of H-(N-cyclopropyl)Gly 6-carbamoyl-3-picolylamide hydrochloride; (FAB-MS) (M+H$^+$): 249.

(b) H-(D)-Chg-(N-Cyclopropyl)Gly 6amidino-3-picolylamide:

As in Example 23(b), 2.5 g (8.8 mmol) of H-(N-cyclopropyl)Gly 6-carbamoyl-3-picolylamide hydrochloride and 2.3 g (8.8 mmol) of Boc-(D)-Chg—OH resulted in 1.88 g of Boc-(D)-Chg-(N-cyclopropyl)Gly 6-amidino-3-picolylamide hydroacetate; FAB-MS (M+H$^+$): 487.

Elimination of the Boc protective group resulted in 1.73 g of H-(D)-Chg-(N-cyclopropyl)Gly 6-amidino-3-picolylamide dihydrochloride; FAB-MS (M+H$^+$): 387.

EXAMPLE 34

(D)-Cyclohexylglycylproline 4-amidino-1-naphthylmethylamide dihydrochloride:

1-Azidomethyl-4-cyanonaphthalene:

24.6 g (0.1 mol) of 1-bromomethyl-4-cyanonaphthalene (M. J. S. Dewar, P. J. Grisdale, J. Amer. Chem. Soc. 84 (1962) 3541) were dissolved in 100 ml of dimethylformamide, 98 g (0.15 mol) of sodium azide were added and the mixture was stirred at RT overnight.

After addition of 100 ml of water and 100 ml of an ethyl acetate/methyl t-butyl ether mixture (1/1), the organic phase was separated off, washed twice with water and dried over MgSO$_4$, and the solvent was distilled off under reduced pressure. The resulting pale yellowish crude product was used without further purification in the next reaction.

1-Aminomethyl-4-cyanonaphthalene hydrochloride:

The azide dissolved in 30 ml of THF was slowly added dropwise to a solution of 26.2 g (1 mol) of triphenylphosphine in 70 ml of THF at 10° C. (evolution of nitrogen). After the addition was complete, 2.75 ml (0.15 mol) of water were added dropwise and the reaction mixture was stirred at RT overnight. The residue after stripping off the solvent was taken up in dilute hydrochloric acid, the insoluble constituents were filtered off with suction, and the filtrate was washed several times with toluene, to remove the triphenylphosphine oxide completely. The acid phase was adjusted to pH 9 with 1 N NaOH and then extracted with ethyl acetate several times, the combined ethyl acetate phases were dried with MgSO$_4$ and, after reduction to about one half of the initial volume, acidified with ethereal hydrochloric acid solution. Filtration with suction and drying resulted in 19.5 g (87% of theory) of hydrochloride being isolated. White crystals, m.p.>240° C.

Boc-(D)-Cyclohexylglycylproline 4-amidino-1-naphthylmethylamide acetate:

Boc-(D)-Cyclohexylglycylproline, prepared by reacting Boc-(D)-cyclohexylglycine with proline methyl ester and subsequent hydrolysis, was coupled by general method 2 with 1-amino-methyl-4-cyanonaphthalene hydrochloride and then the cyano group was converted into the amidine functionality by general method 1. The acetate was isolated in the form of white crystals. m.p. 144–147° C.; FAB-MS (M+H$^+$): 526.

(D)-Cyclohexylglycylproline 4-amidino-1-naphthylmethylamide dihydrochloride:

The Boc group was eliminated from the above compound using isopropanolic hydrochloric acid to afford the dihydrochloride in the form of white crystals. m.p. 228–232° C.; FAB-MS (M+H$^+$): 436.

EXAMPLE 35

(D,L)-(4-Tetrahydropyranyl)glycylproline 2-methoxy-4-amidinobenzylamide:

(a) Boc-(D,L)-Thpg-Pro (2-MeO—4—CN)benzylamide:

2.9 g (11.2 mmol) of Boc-(D,L)-Thpg—OH were reacted as in Example 26(b) with 3.3 g (11.2 mmol) of H-Pro 2-MeO—4—CN—benzylamide hydrochloride. 4.8 g of product were obtained.

$^1$H-NMR (DMSO-D$^6$; δ in ppm): 8.40 and 7.95 (1H, NH (2 diastereomers or 2 rotamers)), 7.5–6.9 (m,4H), 4.45–3.95 (m,3H), 3.90–3.70 (m,6H), 3.65–3.05 (m,4H), 2.2–1.1 (m,18H)

(b) (D,L)-(4-Tetrahydropyranyl)glycylproline 2-methoxy-4-amidinobenzylamide:

2.0 g (4.0 mmol) of the nitrile were reacted as in Example 26(b) with hydroxylamine hydrochloride (10 mmol) and DIPEA (24 mmol) to give 2.0 g of the corresponding hydroxyamidine. Hydrogenation of the hydroxyamidine with Raney nickel/H$_2$ in MeOH and one equivalent of acetic acid and subsequent purification by column chromatography on silica gel (mobile phase: DCM/15% MeOH/5% HOAc (50% strength)) resulted in 1.3 g (60%) of the Boc-protected product in the form of 2 diastereomers (in the ratio 1:1) and of an HPLC purity of 99%.

The Boc protective group was eliminated in DCM/hydrogen chloride. 1.1 g of the product were obtained with an HPLC purity of 99%; FAB-MS (M+H$^+$): 418.

EXAMPLE 36

(D,L)-β,β-Diphenylalanylproline 2-methoxy-4-amidinobenzylamide:

(a) Boc-(D,L)-Dpa-Pro 2-MeO—4—CN—benzylamide:

6.0 g (17.6 mmol) of Boc-(D,L)-Dpa—OH and 5.2 g (17.6 mmol) of H-Pro 2-MeO—4—CN—benzylamide hydrochloride were converted as in Example 23 (b) with subsequent purification by column chromatography on silica gel (mobile phase: DCM/4.5% MeOH) into 5.6 g of product.

$^1$H-NMR (DMSO-d$^6$; δ in ppm): 8.45 and 9.95 (1H,NH (2 diastereomers or rotamers)), 7.5–6.9 (m,14H), 5.35–4.95 (m,1H), 4.5–4.1 (m,3H), 4.0–3.0 (m,3H), 3.90 and 3.85 (s,3H (2 diastereomers)), 2.1–1.1 (m,13H).

(b) Boc-(D,L)-Dpa-Pro—NH—(2-MeO)-4-amb:

The hydroxyamidine was obtained by reacting the nitrile with hydroxylamine hydrochloride as in Example 26(b). $^1$H-NMR (DMSO-d$^6$): 5.90–5.78 ppm (2s, 1H, OH (2 diastereomers)).

(c) H-(D,L)-Dpa-Pro—NH—(2-MeO)-4-amb:

Cleavage of the OH group by hydrogenolysis as in Example 26(b) and subsequent purification by column chromatography on silica gel (mobile phase: DCM/10%–20% MeOH/3% HOAc (50% strength)) resulted in Boc-(D,L)-Dpa-Pro—NH—2-MeO)-4-amb dihydroacetate as 1:1 mixture of diastereomers in a purity of almost 100% (HPLC). The Boc protective group was eliminated in DCM with gaseous hydrogen chloride, and the product was obtained as dihydrochloride with the same purity and same diastereomer ratio as the previous stage.

$^1$H-NMR (DMSO-d$^6$; δ in ppm): 9.70–9.25 (4H, amidine), 8.9–8.4 (4H, NH and NH$_3^\oplus$), 7.7–7.0 (13H), 5.2–4.9 (m, 1H), 4.5–3.7 (8H), 3.25 (m, 1H), 2.95 (m, 1H), 2.2–1.2 (4H).

EXAMPLE 37
(D,L)-(2-Norbornyl)glycylproline 2-methoxy-4-amidinobenzylamide:

3.0 g (11.1 mmol) of Boc-(D,L)-(2-norbornyl)Gly—OH and 3.3 g (11.1 mmol) of H-Pro 2-MeO—4—CN—benzylamide hydrochloride were condensed as in Example 23(b) to give 5.0 g of Boc-(D,L)-(2-norbornyl)Gly-Pro 2-MeO—4—CN—benzylamide and further converted via the hydroxyamidine stage with subsequent hydrogenation into 3.1 g of Boc-(D,L)-(2-norbornyl)Gly-Pro 2-MeO—4—am-benzylamide. The Boc protective group was eliminated in DCM/gaseous hydrogen chloride, and the corresponding amidine dihydrochloride resulted after the solvent was stripped off; FAB-MS (M+H$^+$): 428.

EXAMPLE 38
(D,L)-(1-Tetralinyl)glycylproline 2-methoxy-4-amidinobenzylamide:

3.0 g (9.8 mmol) of Boc-(D,L)-(1-tetralinyl)Gly—OH and 2.9 g (9.8 mmol) of H-Pro 2-MeO—4—CN—benzylamide hydrochloride were condensed as in Example 23(b) to give 4.2 g of Boc-(D,L)-(1-tetralinyl)Gly-Pro 2-MeO—4—CN—benzylamide and further converted via the hydroxyamidine stage with subsequent hydrogenation into 2.6 g of the corresponding amidine hydroacetate.

The amidine dihydrochloride was obtained after cleavage of the Boc protective group in DCM with gaseous hydrogen chloride; FAB/MS (M+H$^+$): 464.

EXAMPLE 39
(D,L)-Cyclooctylglycylproline 2-methoxy-4-amidinobenzylamide:

(a) 4.8 g (16 mmol) of Boc-(D,L)-Cog-—OH and 5.0 g (16.9 mmol) of H-Pro 2-MeO—4—CN—benzylamide hydrochloride were condensed as in Example 23(b) to give 4.7 g of Boc-(D,L)-Cog-Pro 2-MeO—4—CN—benzylamide. $^1$H-NMR (DMSO-d$^6$, δ in ppm): 8.35 and 7.95 (t,1H,NH (2 diastereomers)), 7.50–7.25 (3H), 7.10 and 6.85 (d,1H, NH (2 diastereomers)), 4.45–3.95 (4H), 3.85 (s,3H,OMe), 3.90–3.50 (4H), 2.20–1.15 (28H).

(b) 2.0 g of the nitrile were further converted as in Example 23(b) via the hydroxyamidine stage with subsequent hydrogenation and cleavage of the Boc protective group into 1.7 g of H-(D,L)-Cog-Pro 2-Me-4-am-benzylamide dihydrochloride.
$^1$H-NMR (DMSO-d$^6$, δ in ppm): 9.60 and 9.30 (4H, amidine (2 diastereomers)), 8.80 (NH), 8.60 and 8.30 (NH$_3^\oplus$ (2 diastereomers)), 7.60–7.25 (3H), 4.50–4.10 (4H), 4.00–3.40 (4H), 3.90 (s,3H), 2.20–1.20 (19H).

EXAMPLE 40
(D)-(α-Methyl)cyclohexylalanylproline 2-methoxy-4-amidinobenzylamide:

2.7 g (9.5 mmol) of Boc-(D)-(α-methyl)-Cha—OH and 2.8 g (9.5 mmol) of H-Pro 2-MeO—4—CN—benzylamide hydrochloride were condensed as in Example 23(b) to give 2.5 g of Boc-(D)-(α-methyl)-Cha-Pro 2-MeO—4—CN—benzylamide. 1.0 g of this were further converted via the hydroxyamidine stage with subsequent hydrogenation and cleavage of the Boc protective group into 0.6 g of H-(D)-(α-methyl)-Cha-Pro 2-MeO—4-am-benzylamide dihydrochloride; FAB-MS (M+H$^+$): 444.

EXAMPLE 41
(D,L)-Dibenzosubserylglycylproline 2-methoxy-4-amidinobenzylamide:

4.4 g (12.0 mmol) of Boc-(D,L)-(dibenzosuberyl)-Gly—OH and 3.5 g (12.0 mmol) of H-Pro 2-MeO—4—CN—benzylamide hydrochloride were condensed as in Example 23(b) to give 6.4 g of Boc-(D,L)-(dibenzosuberyl)-Gly-Pro 2-MeO—4—CN—benzylamide. 2.0 of this were further converted via the hydroxyamidine stage with subsequent hydrogenation and cleavage of the Boc protective group into 0.9 g of H-(D,L)-(dibenzosuberyl)-Gly-Pro 2-MeO—4-am-benzylamide dihydrochloride; FAB-MS (M+H$^+$): 526.

EXAMPLE 42
(D,L)-(3,4,5-Trimethoxy)phenylalanylproline 2-methoxy-4-amidinobenzylamide:

2.10 g (5.9 mmol) of Boc-(3,4,5-trimethoxy)-Phe—OH and 1.75 g (5.9 mmol) of H-Pro 2-MeO—4—CN—benzylamide hydrochloride were condensed as in Example 23(b) to give 3.0 g of Boc-(D,L)-(3,4,5-trimethoxy)-Phe-Pro 2-MeO—4—CN—benzylamide. 1.2 g of this were further converted via the hydroxyamidine stage with subsequent hydrogenation and cleavage of the Boc protective group into 0.4 g of H-(D,L)-(3,4,5-trimethoxy)-Phe-Pro 2-MeO—4—am-benzylamide dihydrochloride; FAB-MS (M+H$^+$): 485.

EXAMPLE 43
(D,L)-(Trimethylsilyl)alanylproline 2-methoxy-4-amidinobenzylamide:

2.00 g (7.65 mmol) of Boc-(trimethylsilyl)-Ala—OH and 2.26 g (7.65 mmol) of H-Pro 2-MeO—4—CN—benzylamide hydrochloride were condensed as in Example 23(b) to give 3.22 g of Boc-(D,L)-(trimethylsilyl)-Ala-Pro 2-MeO—4—CN—benzylamide.

1.60 g of this were further converted via the hydroxyamidine stage with subsequent hydrogenation and cleavage of the Boc protective group into 0.65 g of H-(D)-(trimethylsilyl)-Ala-Pro 2-MeO—4-am-benzylamide dihydrochloride; FAB-MS (M+H$^+$): 420.

EXAMPLE 44
(D)-(tert-Butyl)-serylproline 2-methoxy-4-amidinobenzylamide:

5.0 g (16.9 mmol) of Z-(D)-(tBu)-Ser—OH and 5.0 g (16.9 mmol) of H-Pro 2-MeO—4—CN—benzylamide hydrochloride were condensed as in Example 23(b) to give 8.8 g of Z-(D)-(tBu)-Ser-Pro 2-MeO—4—CN—benzylamide. 4.1 g of this were further converted via the hydroxyamidine stage with subsequent hydrogenation into 3.0 g of Z-(D)-(tBu)-Ser-Pro 2-MeO—4-am-benzylamide hydroacetate. Cleavage of the Z protective group by hydrogenolysis was carried out in 80 ml of methanol and one equivalent of acetic acid in the presence of 185 mg of Pd/C (10%) at RT. 2.3 g of impure product were obtained as dihydroacetate, which was purified by MPLC; FAB-MS (M+H$^+$): 419.
$^1$H-NMR (DMSO-d$^6$, δ in ppm): 9.3–8.7 (7H, amidine and NH$_3^+$), 8.1 (1H, NH), 7.5–7.3 (3H), 4.1–4.0 (dd,1H), 3.95 (s,3H), 3.9–3.2 (7H), 2.2–1.5 (4H), 1.05 (s,9H).

EXAMPLE 45
(D,L)-(3-Phenyl)prolylproline 2-methoxy-4-amidinobenzylamide:

1.3 (4.5 mmol) of Boc-(D,L)-(3-phenyl)-Pro—OH (see also Example 30) and 1.3 g (4.5 mmol) of H-Pro 2-MeO—4—CN—benzylamide hydrochloride were condensed as in Example 23 (b) to give 1.7 g of Boc-(D,L)-(3-phenyl)-Pro-Pro 2-MeO—4—CN—benzylamide and further converted via the hydroxyamidine stage with subsequent hydrogenation and cleavage of the Boc protective group into 0.7 g of H-(D,L)-(3-phenyl)-Pro-Pro 2-MeO—4-am-benzylamide dihydrochloride; FAB-MS (M+H$^+$): 450.

EXAMPLE 46

(D)-Cyclohexylglycylpiperidine-2-carboxylic acid 2-methoxy-4-amidinobenzylamide:

The compound was prepared as in Example 48 or 23 (b). To do this, 1.5 g (4.1 mmol) of Boc-(D)-Chg-Pic—OH, which have been prepared by condensation of Boc-(D)-Chg—OH with H-Pic—Ome hydrochloride and subsequent alkaline hydrolysis of the ester, were condensed with 0.8 g (4.1 mmol) of 2-MeO—4—CN-benzylamine hydrochloride to give 1.9 g of Boc-(D)-Chg-Pic 2-MeO—4—CN—benzylamide. This substance was further converted via the hydroxyamidine stage with subsequent hydrogenation and cleavage of the Boc protective group into 1.0 g of H-(D)-Chg-Pic 2-Meo-4-am-benzylamide dihydrochloride; FAB-MS (M+H$^+$): 430.

EXAMPLE 47

(D)-Cyclohexylglycyl(N-cyclopropyl)glycine 2-methoxy-4-amidinobenzylamide:

Example 47 was prepared as in Examples 48 and 23 (b). To do this, 1.5 g (4.2 mmol) of Boc-(D)-Chg-(N-cyclopropyl)-Gly—OH, which had been prepared by condensation of Boc-(D)-Chg—OH with H-(N-cyclopropyl)-Gly—OMe hydrochloride and subsequent alkaline hydrolysis of the ester, were condensed with 0.83 g (4.2 mmol) of 2-Meo-4—CN—benzylamine hydrochloride to give 1.5 g of Boc-(D)-Chg-(N-cyclopropyl)-Gly 2-MeO—4—CN—benzylamide. This substance was further converted via the hydroxyamidine stage with subsequent hydrogenation and cleavage of the Boc protective group into 0.85 g of H-(D)-Chg-(N-cyclopropyl)-Gly 2-MeO—4-am-benzylamide dihydrochloride; FAB-MS (M+H$^+$): 416.

EXAMPLE 48

(D)-Cyclohexylalanylpiperidine-2-carboxylic acid 2-methoxy-4-amidinobenzylamide:

a) Boc-(D)-Cha-Pic—OH:

7.55 g (27.8 mmol) of Boc-(D)-Cha—OH, 5.0 g (27.8 mmol) of H-Pic—OMe hydrochloride and 20.5 ml of DIPEA were mixed at −5° C. A solution of 23 ml (31 mmol) of PPA (50% strength solution in ethyl acetate) and 23 ml of DCM was added dropwise to this at −5° C. over the course of 30 min. The mixture was stirred at 0° C. for a further 2 h and then washed with 0.5 N sodium hydroxide solution, then with 1 N hydrochloric acid and finally with saturated brine, and the organic phase was dried over Na$_2$SO$_4$ and the solvent was stripped off. 9.7 g of Boc-(D)-Cha-Pic—OMe were obtained and were hydrolyzed in 50 ml of methanol with 21 ml of 3 N sodium hydroxide solution at RT for 2 h. The solvent was stripped off, DCM was added, dilute hydrochloric acid was added to acidify, and the DCM phase was dried over Na$_2$SO$_4$. The solvent was stripped off to result in 8.5 g of Boc-(D)-Cha-Pic—OH.

b) Boc-(D)-Cha-Pic 2-MeO—4—CN—benzylamide:

8.5 g (22.2 mmol) of Boc-(D)-Cha-Pic—OH were stirred in 50 ml of THF with 2.56 g of HOSucc and 4.58 g of DCC at 0° C. for 30 min. Then, at 5° C. 4.4 g (22.2 mmol) of 2-MeO—4—CN—benzylamine hydrochloride, 25 ml of THF and finally 3.1 ml of TEA were added, and the mixture was stirred at 0° C. for 1 h and allowed to warm to RT overnight. The solid was filtered off, the solvent was stripped off from the filtrate, and the product was taken up in ethyl acetate and washed successively with 0.5 N sodium hydroxide solution, 0.5 N hydrochloric acid and saturated brine. After drying over Na$_2$SO$_4$, the solvent was completely stripped off. 11.5 g of Boc-(D)-Cha-Pic 2-MeO—4—CN—benzylamide were obtained.

$^1$H-NMR (DMSO-d$^6$, δ in ppm): 8.50 and 7.95 (together 1H, NH, 2 rotamers), 7.5–7.0 (4H), 4.55–4.20 (3H), 3.85 (s, 3H), ca. 3.8 (1H), ca. 3.4–3.1 (2H), 2.3–0.8 (28H).

c) H-ID)-Cha-Pic 2-MeO—4-amidinobenzylamide:

3.0 g (5.7 mmol) of the nitrile from Example 46 (b) were converted as in Example 23 (b) via the hydroxyamidine stage with subsequent hydrogenation and cleavage of the Boc protective group into 1.9 g of H-(D)-Cha-Pic 2-MeO—4-am-benzylamide dihydrochloride; FAB-MS (M+H$^+$): 444.

EXAMPLE 49

(D)-Cyclohexylglycylproline 2-ethoxy-4-amidinobenzylamide:

Preparation took place as in Examples 23 (b) and 48. 4.1 g (11.5 mmol) of Boc-(D)-Chg-Pro—OH were condensed as in 48 (b) with 2.4 g (11.5 mmol) of 2-EtO—4—CN—benzylamine hydrochloride to give 4.7 g of Boc-(D)-Chg-Pro 2-Eto-4—CN—benzylamide hydrochloride. This substance was further converted via the hydroxyamidine stage with subsequent hydrogenation and cleavage of the Boc protective group into 3.7 g of H-(D)-Chg-Pro 2-EtO—4-am-benzylamide dihydrochloride.

$^1$H-NMR (DMSO-d$^6$, δ in ppm): 9.48 and 9.25 (4H, amidine), 8.83 (t, 1H, NH), 8.60 (3H, NH$_3^+$), 7.45–7.30 (3H), 4.40–4.15 (6H, 2xCH$_2$, 2xCH), 3.98–3.82 (2H, CH$_2$), 2.20–1.00 (18H, CH$_3$, 7xCH$_2$, CH).

EXAMPLE 50

(D)-Cyclohexylglycylproline 2-iodo-4-amidinobenzylamide:

Preparation took place as in Examples 23 (b) and 48. 10.4 g (29.2 mmol) of Boc-(D)-Chg-Pro—OH were condensed as in 48 (b) with 8.6 g (29.2 mmol) of 2-I-4—CN—benzylamine hydrochloride to give 14.2 g of Boc-(D)-Chg-Pro 2-I-4—CN—benzylamide. 3.0 g of this compound were further converted via the hydroxyamidine stage with subsequent hydrogenation into 0.9 g of Boc-(D)-Chg-Pro 2-I-4-am-benzylamide hydroacetate. Elimination of the Boc protective group resulted in 0.3 g of H-ID)-Chg-Pro 2-I-4-am-benzylamide dihydrochloride; FAB-MS (M+H$^+$): 512.

EXAMPLE 51

(D)-Cyclohexylglycylproline 2-hydroxy-4-amidinobenzylamide:

1.95 g (5.46 mmol) of Boc-(D)-Chg-Pro—OH were condensed with 1.50 g (5.46 mmol) of 2-BnO—4—CN—benzylamine hydrochloride as in Example 48 (b) to give Boc-(D)-Chg-Pro 2-BnO—4—CN—benzylamide almost quantitatively. 1.30 g of this compound were hydrogenated, as in Example 23 (b), via the hydroxyamidine stage with Raney nickel/hydrogen to give a mixture of Boc-(D)-Chg-Pro 2-BnO—4-am-benzylamide hydroacetate and Boc-(D)-Chg-Pro 2—OH—4-am-benzylamide hydroacetate. To complete the benzyl cleavage, the hydrogenation was repeated as in Example 44 with Pd/C/hydrogen. Cleavage of the Boc protective group resulted in 0.61 g of H-(D)-Chg-Pro 2—OH—4-am-benzylamide dihydrochloride (HPLC purity 98.2%), FAB-MS (M+H$^+$): 402.

EXAMPLE 52

(D)-Cyclohexylglycylproline 3-methoxy-4-amidinobenzylamide:

a) Boc-(D)-Chg-Pro 3-MeO—4—CN—benzylamide:

From 2.7 g (7.6 mmol) of Boc-(D)-Chg-Pro—OH and 1.5 g (7.6 mmol) of 3-MeO—4—CN—benzylamine hydrochloride as in Example 48 (b), 3.0 g of the product (a) were obtained.

$^1$H-NMR (DMSO-d$^6$, δ in ppm): 8.05 (1H, NH), 7.60 (d, 1H), 7.10 (1H), 7.05 (1H, NH), 6.95 (1H), 4.50–4.20 (3H), 3.95 (s, 3H), ca. 3.9-ca. 3.3 (3H), 2.1–1.0 (24H).

b) H-(D)-Chg-Pro 3-MeO—4-am-benzylamide:

3.0 g of the nitrile (a) were converted as in Example 23 (b) via the hydroxyamidine stage with subsequent hydrogenation and cleavage of the Boc protective group into 1.3 g of H-(D)-Chg-Pro 3-MeO—4-am-benzylamide dihydrochloride (HPLC purity>99%); FAB-MS (M+H$^+$): 416.

EXAMPLE 53

(D)-Cyclohexylglycylproline 3-hydroxy-4-amidinobenzylamide:

1.94 g (5.46 mmol) of Boc-(D)-Chg-Pro-OH were condensed with 1.50 g (5.46 mmol) of 3-BnO-4-CN-benzylamine hydrochloride as in Example 48 (b) to give 2.12 g of Boc-(D)-Chg-Pro 3-BnO-4-CN-benzylamide. 1.0 g of this compound were hydrogenated as in Example 23 (b) via the hydroxyamidine stage, in contrast to Example 51, immediately with Pd/C/hydrogen. Cleavage of Boc protective group resulted in 0.42 g of H-(D)-Chg-Pro 2-OH-4-am-benzylamide dihydrochloride; FAB-MS (M+H$^+$): 402.

EXAMPLE 54

(D)-Cyclohexylglycylproline 3-chloro-4-amidinobenzylamide 2.38 g (9.33 mmol) of Boc-(D)-Chg-Pro-OH were condensed with 2.80 g (9.33 mmol) of 3-Cl-4-CN-benzylamine hydrochloride as in Example 23 (b) to give 4.35 g of Boc-(D)-Chg-Pro 3-Cl-4-CN-benzylamide. 1.60 g of this compound were further converted as in Example 23 (b) via the hydroxyamidine stage with subsequent hydrogenation and cleavage of the Boc protective group into 0.91 g of H-(D)-Chg-Pro 3-Cl-4-am-benzylamide dihydrochloride; FAB-MS (M+H$^+$): 420.

EXAMPLE 55

(D)-Cyclohexylglycylproline 2-hydroxycarbonylmethoxy-4-amidino-benzylamide 2.00 g (3.48 mmol) of Boc-(D)-Chg-Pro 2-BnO-4-CN-benzylamide (see Example 51) were hydrogenated as in Example 44 with Pd/C/hydrogen. 1.35 g of Boc-(D)-Chg-Pro 2-OH-4-CN-benzylamide were obtained and were stirred with an equimolar amount of K$_2$CO$_3$ in 30 ml of DMF and 0.41 ml (2.80 mmol) of tert-butyl bromoacetate at RT for 3 d. The product was extracted into organic phase by adding 100 ml of water and 100 ml of ethyl acetate/ether 1:1 and, after drying over Na$_2$SO$_4$, the solvent was stripped off. The crude product obtained in this way was converted as in Example 23 (b) via the hydroxyamidine stage with subsequent hydrogenation and simultaneous cleavage of the Boc protective group and of the tert-butyl ester in dioxane/hydrochloric acid, after MPLC, into 280 mg of H-(D)-Chg-Pro 2-(HOOC-CH$_2$O)-4-am-benzylamide dihydrochloride; FAB-MS (M+H$^+$): 460.

EXAMPLE 56

N-(hydroxycarbonylmethyl)-(D)-cyclohexylalanylproline 2-methoxy-4-amidinobenzylamide 3.2 g (7.8 mmol) of H-(D)-Cha-Pro 2-MeO-4-CN-benzylamide which had been obtained from the condensation of Boc-(D)-Cha-OH with H-Pro 2-Meo-4-CN-benzylamide hydrochloride to give Boc-(D)-Cha-Pro 2-MeO-4-CN-benzylamide and subsequent cleavage of the Boc protective group in DCM/MeOH 20:1 by passing in gaseous hydrogen chloride at 020 C. was reacted in 100 ml of DCM and 4.7 ml of DIPEA at RT within 1.5 g of tert-butyl bromoacetate in 3 d to give 3.2 g of tBuOOC—CH$_2$-(D)-Cha-Pro 2-MeO-4-CN-benzylamide hydrochloride, after washing the DCM phase with 0.5 N hydrochloric acid. This compound was converted as in Example 23 (b) via the hydroxyamidine stage with subsequent hydrogenation into crude tBuOOC—CH$_2$-(D)-Cha-Pro 2-MeO-4-am-benzylamide dihydroacetate. Purification by column chromatography on silica gel (mobile phase: DCM/10–20% MeOH/3.5% HOAc (50% strength)) resulted in 1.2 g with a purity>99% (HPLC). Cleavage of the tert-butyl ester in DCM with gaseous hydrogen chloride at 0–5° C. resulted in 1.1 g of HOOC—CH$_2$-(D)-Cha-Pro 2-MeO-4-am-benzylamide dihydrochloride being isolated; FAB-MS (M+H$^+$): 488.

EXAMPLE 57

N-(Hydroxycarbonylmethyl)-(D)-cyclohexylalanyl-3,4-dehydroproline 2-methoxy-6-amidinobenzylamide As in Example 26 (a), Boc-Pyr-OH was condensed with 2-MeO-4-CN-benzylamide hydrochloride to give Boc-Pyr 2-MeO-4-CN-benzylamide and the Boc protective group was then eliminated. The subsequent coupling with Boc-(D)-Cha-OH took place as in Example 26 (b). Elimination of the Boc protective group and reaction with tert-butyl bromoacetate as in Example 80 (b) resulted in tBuOOC-CH$_2$-(D)-Cha-Pyr 2-MeO-4-CN-benzylamide.

The cyano group was converted via the thioamide stage into the corresponding amidine hydroiodide as in Example 108. The hydroiodide was converted into the hydroacetate on an ion exchanger, and the tert-butyl ester was then converted with gaseous hydrogen chloride in DCM at 0° C. into HOOC—CH$_2$-(D)-Cha-Pyr 2-MeO-4-am-benzylamide dihydrochloride; FAB-MS: (M+H$^+$): 486.

EXAMPLE 58

N-(Hydroxycarbonylethyl)-(D)-cyclohexylglycylproline 2-methoxy-4-amidinobenzylamide 3.0 g (7.5 mmol) of H-(D)-Chg-Pro 2-MeO-4-CN-benzylamide (see Example 56) were stirred in 70 ml of ethanol with 1.2 g (7.5 mmol) of benzyl acrylate at 60° C. for 6 h and at RT for a further 2 d. The solvent was stripped off and the resulting product BnOOC—CH$_2$—CH$_2$-(D)-Chg-Pro 2-MeO-4-CN-benzylamide was purified on a silicia gel column (mobile phase: DCM/5% MeOH), isolating 2.3 g. This substance was converted as in Example 23 (b) via the hydroxyamidine stage with subsequent hydrogenation (Raney nickel/hydrogen) into 610 mg of BnOOC-CH$_2$—CH$_2$-(D)-Chg-Pro 2-MeO-4-am-benzylamide dihydroacetate. A further hydrogenation step (Pd-C/hydrogen) as in Example 44 yielded 580 mg of HOOC—CH$_2$—CH$_2$-(D)-Chg-Pro 2-MeO-4-am-benzylamide hydroacetate (HPLC purity: 95.9%); FAB-MS (M+H$^+$): 488.

EXAMPLE 59

N-(tert-Butoxycarbonylmethyl)-(D,L)-cyclooctylglycylproline 2-methoxy-4-amidinobenzylamide 2.6 g (4.9 mmol) of Boc-(D,L)-Cog-Pro 2-MeO-4-CN-benzylamide (see Example 39) were, after elimination of the Boc protective group, reacted as in Example 56 with tert-butyl bromoacetate to give 1.4 g of tBuOOC—Ch$_2$-(D,L)-Cog-Pro 2-MeO-4-CN-benzylamide. This substance was converted as in Example 23 (b) via the hydroxyamidine stage with subsequent hydrogenation into 1.0 g of tBuOOC—CH$_2$-(D,L)-Cog-Pro 2-MeO-4-am-benzylamide hydroacetate; FAB-MS (M+H$^+$): 558.

EXAMPLE 60

N-(Hydroxycarbonylmethyl)-(D,L)-cyclooctylglycylproline 2-methoxy-4-amidinobenzylamide 700 mg (1.13 mmol) of the compound from Example 59 were converted by cleavage of the tert-butyl ester with gaseous hydrogen chloride at 0° C. in DCM over the course of 2 h into 600 mg of HOOC—CH$_2$-(D,L)-Cog-Pro 2-MeO-4-am-benzylamide dihydrochloride; FAB-MS (M+H$^+$): 502.

EXAMPLE 61

N-(Hydroxycarbonylmethyl)-(D,L)-diphenylalanylproline 2-methoxy-4-amidinobenzylamide 1.6 g (3.1 mmol) of H-(D,L)-Dpa-Pro 2-MeO-4-CN-benzylamide hydrochloride which was obtained by protective group cleavage from the corresponding Boc-protected compound (Example 36) was reacted with 3.1 mmol of tert-butyl bromoacetate as in Example 56 hydrochloride; FAB-MS (M+H$^+$): 597.

This 0.6 g of the nitrile was converted by a known method first with H$_2$S into the thioamide and then with methyl iodide and subsequently ammonium acetate into the amidine hydroiodide. The product was purified by column chromatography on silica gel (mobile phase: DCM/20% MeOH/5% HOAc (50% strength)) and the iodide was replaced by acetate using an ion exchanger (IRA 420); FAB-MS (M+H$^+$): 614.

The tert-butyl ester was cleaved as in Example 56 to give 0.25 g of HOOC—CH$_2$-(D,L)-Dpa-Pro 2-Meo-4-am-benzylamide dihydrochloride (HPLC purity: 91%), FAB-MS (M+H$^+$): 558; byproducts FAB-MS (M+H$^+$): 572 and 600.

EXAMPLE 62

Benzyloxycarbonyl-(D)-(tert-butyl)serylproline 2-methoxy-4-amidinobenzylamide

The preparation is described in Example 44.

$^1$H-NMR (DMSO-d$^6$, δ in ppm): 8.60 and 8.05 (m, 1H, NH (2 rotamers)), 7.65 and 7.50 (d, 1H, NH (2 rotamers)), 7.40–7.15 (8H), 4.95–4.70 (2d, 2H), 4.45–4.10 (4H), 3.90 (s, 3H), 3.75–3.65 (2H), 3.55–3.35 (4H), 1.10 (s, 9H).

EXAMPLE 63

N-(Hydroxycarbonylmethyl)-(D)-cyclohexylalanylpiperidine-2-carboxylic acid 2-methoxy-4-amidinobenzylamide 4.0 g (7.6 mmol) of Boc-(D)-Cha-Pic 2-MeO-4-CN-benzylamide (Example 48) were, after elimination of the Boc protective group, reacted as in Example 56 with tert-butyl bromoacetate to give 4.0 g of crude tBuOOC—CH$_2$-(D)-Cha-Pic 2-MeO-4-CN-benzylamide hydrochloride. The substance was converted further as in Example 23 (b) via the hydroxyamidine stage with subsequent hydrogenation and cleavage of the tert-butyl ester into 1.8 g of crude HOOC—CH$_2$-(D)-Cha-Pic 2-MeO-4-am-benzylamide dihydrochloride. A portion of the substance was purified by MPLC; FAB-MS (M+H$^+$): 502.

EXAMPLE 64

N-Benzyl-(D)-cyclohexylglycylproline 2-methoxy-4-amidinobenzylamide 2.7 g (6.8 mmol) of H-(D)-Chg-Pro 2-MeO-4-CN-benzylamide were reacted with 6.8 mmol of benzyl bromide at 60° C. in 40 ml of ethanol for 4 h and subsequently purified to give 0.6 g of Ph-CH$_2$-(D)-Chg-Pro 2-MeO-4-CN-benzylamide hydrobromide. The substance was further converted as in Example 23 (b) via the hydroxyamidine stage with subsequent hydrogenation into 0.20 g of Ph-CH$_2$-(D)-Chg-Pro 2-MeO-4-am-benzylamide hydroacetate (HPLC purity: 96.6%); FAB-MS (M+H$^+$): 506.

EXAMPLE 65

N-(Hydroxycarbonylmethyl)-(D)-cyclohexylglycylproline 2-hydroxy-4-amidinobenzylamide 1.8 g (3.1 mmol) of Boc-(D)-Chg-Pro 2-BnO-4-CN-benzylamide were stirred in 35 ml of DCM and 35 ml of trifluoroacetic acid at RT for 2 h. The solvent was stripped off, and the product was again taken up in DCM and made weakly alkaline with NaHCO$_3$ solution. The DCM phase was dried and then the solvent was stripped off. H-(D)-Chg-Pro 2-BnO-4-CN-benzylamide was obtained in quantitative yield. This substance was reacted as in Example 56 with 3.1 mmol of tert-butyl bromoacetate and subsequently purified by column chromatography on silica gel (mobile phase: DCM/5% MeOH). 1.35 g of t-BuOOC—Ch$_2$-(D)-Chg-Pro 2-BnO-4-CN-benzylamide were isolated. The subsequent reactions with hydroxylamine and Raney nickel/H$_2$ as in Example 23 (b) yielded, after purification by column chromatography on silica gel (mobile phase: DCM/15% MeOH/ 3.5% HOAc (50% strength)), 0.9 g of t-BuOOC—CH$_2$-(D)-Chg-Pro 2-BnO-4-amidinobenzylamide dihydroacetate. The O-benzyl group was eliminated by hydrogenolysis in MeOH with Pd/10% C/H$_2$ at RT, and then the tert-butyl ester was converted into the carboxylic acid as in Example 56. Purification by column chromatography on silica gel (mobile phase: DCM/20% MeOH/5% HOAc) resulted in 0.24 g of HOOC—CH$_2$-(D)-Chg-Pro 2-OH-4-amidinobenzylamide dihydrochloride with a purity of 94% (HPLC); FAB-MS (M+H$^+$): 460.

EXAMPLE 66

N-(Hydroxycarbonylmethyl)-(D)-cyclohexylalanylproline 2-hydroxy-4-amidinobenzylamide 2.4 g (4.1 mmol) of Boc-(D)-Cha-Pro 2-BnO-4-CN-benzylamide, which had been obtained by condensing Boc-(D)-Cha-OH and H-Pro 2-BnO-4-CN-benzylamide hydrochloride as in Example 23 (b), was converted by the process described in Example 65 in several stages into 0.6 g of HOOC—CH$_2$-(D)-Cha-Pro 2-OH-4-am-benzylamide dihydrochloride; FAB-MS (M+H$^+$): 474.

EXAMPLE 67

N-(Hydroxycarbonylmethyl)-(D)-cyclohexylglycylproline 2-chloro-4-amidinobenzylamide 3.3 g (7.51 mmol) of H-(D)-Chg-Pro 2-Cl-4-CN-benzylamide hydrochloride, which had been obtained by condensing Boc-(D)-Chg-Pro-OH with 2-Cl-4-CN-benzylamine hydrochloride and subsequent cleavage of the Boc protective group, were reacted as in Example 56 with tert-butyl bromoacetate to give 2.1 g of tBuOOC—CH$_2$-(D)-Chg-Pro 2-Cl-4-CN-benzylamide hydrochloride; FAB-MS (M+H$^+$): 517.

These 2.1 g were further converted as in Example 23 (b) via the hydroxyamidine stage with subsequent hydrogenation into 1.0 g of the corresponding amidine hydroacetate (HPLC purity: 99%) and, after cleavage of the tert-butyl ester, into 0.6 g of HOOC—CH$_2$-(D)-Chg-Pro 2-Cl-4-am-benzylamide dihydrochloride; FAB-MS (M+H$^+$): 478.

EXAMPLE 68

N-(hydroxycarbonylmethyl)-(D,L)-(4-tetrahydropyranyl)alanylproline 6-amidino-3-picolylamide (a) Boc-(D,L)-Thpa-Pro 6-CN-3-picoylamide 4.70 g (17.2 mmol) of Boc-(D,L)-Thpa-OH were stirred in 60 ml of DCM and 11.8 ml of DIPEA at –5° C. with 4.90 g (17.2 mmol) of H-Pro 6-carbamoyl-3-picoylamide and 14 ml of PPA (50% strength solution in ethyl acetate) for 5 min and at 0° C. for a further 2 h. The DCM phase was washed with NaHSO$_4$ solution and then with K$_2$CO$_3$ solution and saturated NaCl solution and dried over Na$_2$SO$_4$. The solvent was completely stripped off to result in 6.33 g of Boc-(D,L)-Thpa-Pro 6-carbamoyl-3-picoylamide, which was then reacted in 50 ml of DCM and 5.4 ml of DIPEA at 0° C. with 2.0 ml of TEAA over the course of 2 h to give 5.5 g of required product.

$^1$H-NMR (DMSO-d$^6$, δ in ppm): 8.65 (1H, aromatic H), 8.50 and 8.20 (1H, NH, 2 diastereomers), 8.05–7.80 (2H, aromatic H), 7.12 and 7.02 (1H, NH, 2 diastereomers), 4.5–4.2 (4H, CH$_2$ and 2 CH), 3.9–3.1 (6H, 3 CH$_2$), 2.2–1.0 (20H, 5 CH$_2$, CH and Boc)

(b) tBuOOC—CH$_2$-(D,L)-Thpa-Pro 6-CN)-3-picolylamide 5.5 (11.03 mmol) of the above compound (a) were converted quantitatively in 60 ml of isopropanol which contained 57 mmol of HCl at 50° C. over the course of 1.5 h into H-(D,L)-Thpa-Pro 6-CN-3-picolylamide hydrochloride. The hydrochloride was taken up in 80 ml of DCM, 8.6 ml of DIPEA were added and, after addition of 1.63 ml (11.3 mmol) of tert-butyl bromo-acetate, the reaction mixture was stirred at RT for 3 days. The solution was then washed successively with 5% strength citric acid, NaHCO$_3$ solution and saturated NaCl solution and dried over Na$_2$SO$_4$. The solvent was stripped off to result in 4.2 g of tBuOOC—CH$_2$-(D,L)-Thpa-Pro 6-CN-3-picolylamide.

(c) HOOC—CH$_2$-(D,L)-Thpa-Pro 6-am-3-picolylamide 4.2 g (8.4 mmol) of the above compound (b) were stirred in 75 ml of DCM/MeOH 1:1 with 584 mg (8.4 mmol) of hydroxylamine hydrochloride and 8.6 ml of DIPEA at 40° C. for 5 h and at RT for a further 12 h. Dilute acetic acid was added until the pH reached 5-6, and the product was extracted with DCM. Drying and stripping off the solvent resulted in 4.1 g of the corresponding hydroxyamidine. This was hydrogenated in 100 ml of methanol and one equivalent of acetic acid in the presence of 250 mg of Pd/C (10%) at RT until the required amount of hydrogen had been taken up. The catalyst was filtered off, and the solvent was stripped off to result in 4.2 g of crude tBuOOC—CH$_2$-(D,L)-Thpa-Pro 6-am-3-am-3-picolylamide hydroacetate, which was purified by column chromatography on silica gel (mobile phase: DCM/20% MeOH/3.5% HOAc (50% strength)). Cleavage of the tert-butyl ester on 1.6 g of the purified material with gaseous HCl at 0° C. in DCM resulted in 1.4 g of HOOC—CH$_2$-(D,L)-Thpa-Pro 6-am-3-picolylamide dihydrochloride with a purity>99% (HPLC); FAB-MS (M+H$^+$): 461.

EXAMPLE 69

N-(Hydroxycarbonylmethl)-(D,L)-(4-tetrahydropyranyl)glycylproline 6-amidino-3-picolylamide 8.2 g (17.4 mmol) of Boc-(D,L)-Thpg-Pro 6-CN-3-picolylamide, which had been prepared as in Example 68 from Boc-(D,L)-Thpg-OH and H-Pro 6-carbamoyl)-3-picolylamide, were converted by the process described in Example 68 into 0.4 g of HOOC—CH$_2$-(D,L)-Thpg-Pro 6-am-3-picolylamide dihydrochloride with a purity of 93% (HPLC); FAB-MS (M+H$^+$): 447.

EXAMPLE 70

N-(Hydroxycarbonylmethyl)-(D,L)-(4-methylcyclohexyl)glycylproline 6-amidino-3-picolylamide dihydrochloride As in Example 68, Boc-(D,L)-(4-Me)Chg-OH (see precursor syntheses for preparation) was first coupled with H-Pro-NH-3-(6-CONH$_2$)-pico to give Boc-(D,L)-(4-Me)Chg-Pro-NH-3-(6-CONH$_2$)-pico, the primary amide was dehydrated to the nitrile, subsequently the Boc protective group was eliminated and the free amino group was alkylated with tertiary-butyl bromoacetate. The nitrile functionality in tuBuOOC—CH$_2$-(D,L)-(4-Me)Chg-Pro-NH-3-(6-CN)-pico was converted via the hydroxyamidine to the amidine, and subsequently the t-butyl ester was cleaved with HCl. The final product was obtained after purification as crystalline white powder. FAB-MAS (M+H$^+$): 459.

EXAMPLE 71

N-(Hydroxycarbonylmethyl)-(D,L)-4-isopropylcyclohexyl)glycylproline 6-amidino-3-picolylamide dihydrochloride As in Example 68, Boc-(D,L)-(4-iPr)Chg-OH (see precursor syntheses for preparation) was first coupled with H-Pro-NH-3-(6-CONH$_2$)-pico to give Boc-(D,L)-(4-iPr)Chg-Pro-NH-3-(6-CONH$_2$)-pico, the primary amide was dehydrated to the nitrile, subsequently the Boc protective group was eliminated and the free amino group was alkylated with tertiary-butyl bromoacetate. The nitrile functionality in tBuOOC—CH$_2$-(D,L)-(4-iPr)Chg-Pro-NH-3-(6-CN)-pico was converted via the hydroxyamidine into the amidine and subsequently the t-butyl ester was cleaved with HCl. The final product was obtained after purification as crystalline white powder. FAB-MS (M+H$^+$): 487.

EXAMPLE 72

N-Hydroxycarbonylmethyl)-(D,L)-(4-tert-butylcyclohexyl)glycylproline 6-amidino-3-picolylamide dihydrochloride As in Example 68, Boc-(D,L)-(4-tBu)Chg-OH (see precursor syntheses for preparation) was first coupled with H-Pro-NH-3-(6-CONH$_2$)-pico to give Boc-(D,L)-(4-tBu) Chg-Pro-NH-3-(6-CONH$_2$)-pico the primary amide was dehydrated to the nitrile, subsequently the Boc protective group was eliminated and the free amino group was alkylated with tertiary-butyl bromoacetate. The nitrile functionality in tBuOOC—CH$_2$-(D,L)-(4-tBu)Chg-Pro-NH-3-(6-CN)-pico was converted via the hydroxyamidine to the amidine, and subsequently the t-butyl ester was cleaved with HCl. The final product was obtained after purification as crystalline white powder. FAB-MS (M+H$^+$): 501.

EXAMPLE 73

N-(Hydroxycarbonylmethyl)-(D,L)-(3,3-dimethylcyclohexyl)glycyl-proline 6-amidino-3-picolylamide dihydrochloride As in Example 68, Boc-(D,L)-(3,3-Me$_2$)Chg-OH (see precursor syntheses for preparation) was first coupled with H-Pro-NH-3-(6-CONH$_2$)-pico to give Boc-(D,L)-(3,3-Me$_2$) Chg-Pro-NH-3-(6-CONH$_2$)-pico, the primary amide was dehydrated to the nitrile, subsequently the Boc protective group was eliminated and the free amino group was alkylated with tertiary-butyl bromoacetate. The nitrile functionality in tBuOOC—CH$_2$-(D,L)-(3,3-Me$_2$)Chg-Pro-NH-3-(6-CN)-pico as converted via the hydroxyamidine to the amidine, and subsequently the t-butyl ester was cleaved with HCl. The final product was obtained after purification as crystalline white powder. FAB-MS (M+H$^+$): 473.

EXAMPLE 74

N-(Hydroxycarbonylmethyl)-(D)-(tert-butyl) serylproline 6-amidino-3-picolylamide acetate As in Example 68, Z-(D)-Ser(tBu)-OH was first coupled with H-Pro-NH-3-(6-CONH$_2$)-pico to give Z-(D)-Ser(tBu)-Pro-NH-3-(6-CONH$_2$)-pico, the Z protective group was eliminated by hydrolysis, the free amino group was initially alkylated with benzyl bromoacetate and subsequently reacted with Z—Cl to give BuOOC—CH$_2$-(Z)-(D)-Ser (tBu)-Pro-NH-3-(6-CONH$_2$)-pico. After dehydration of the amide to the nitrile functionality the latter was converted via the hydroxyamidine by hydrogenolysis into the amidine, with simultaneous eliminating of the benzyl and Z groups. The final product was obtained after purification as white amorphous powder; FAB-MS (M+H $^+$): 449.

EXAMPLE 75

N-(Hydroxycarbonylmethyl)-(D,L)-cyclopentylglycylproline 6-amidino-3-picolylamide dihydrochloride As in Example 68, Boc-(D,L)-Cpg-OH (see precursor syntheses for preparation) was first coupled with H-Pro-NH-3-(6-CONH$_2$)-pico to give Boc-(D,L)-Cpg-Pro-NH-3-(6-CONH$_2$)-pico, the primary amide was dehydrated to the nitrile, subsequently the Boc protective group was eliminated and the free amino group was alkylated with tertiary-butyl bromoacetate. The nitrile functionality in tBuOOC—CH$_2$-(D,L)-Cpg-Pro-NH-3-(6-CN)-pico was converted via the hydroxyamidine to the amidine, and subsequently the t-butyl ester was cleaved with HCl. The final product was obtained after purification as crystalline white powder. FAB-MS (M+H$^+$): 431.

EXAMPLE 76

N-(Hydroxycarbonylmethyl)-(D,L)-(1-tetralinyl) glcylproline 6-amidino-3-picolylamide dihydrochloride As in Example 68, Boc-(D,L)-(1-tetralinyl)Gly-OH (see precursor syntheses for preparation) was first coupled with H-Pro-NH-3-(6-CONH$_2$)-pico to give Boc-(D,L)-(1-tetralinyl)Gly-Pro-NH-3-(6-CONH$_2$)-pico, the primary amide was dehydrated to the nitrile, subsequently the Boc protective group was eliminated and the free amino group was alkylated with tertiary-butyl bromoacetate. The nitrile functionality in tBuOOC—CH$_2$-(D,L)-(1-tetralinyl)Gly-Pro-NH-3-(6-CN)-pico was converted via the hydroxyamidine to the amidine, and subsequently the t-butyl ester was cleaved with HCl. The final product was obtained after purification as crystalline white powder. FAS-MS (M+H$^+$): 493.

EXAMPLE 77

N-(Hydroxycarbonylmethyl)-(D,L)-(2-norbornyl) glycylproline 6-amidino-3-picolylamide dihydrochloride As in Example 68, Boc-(D,L)-(2-norbornyl)Gly-OH (see precursor syntheses for preparation) was first coupled with H-Pro-NH-3-(6-CONH$_2$)-pico to give Boc-(D,L)-(2-norbornyl)Gly-Pro-NH-3-(6CONH$_2$)-pico, the primary amide was dehydrated to the nitrile, subsequently the Boc protective group was eliminated and the free amino group was alkylated with tertiary-butyl bromo-acetate. The nitrile functionality in tBuOOC—CH$_2$-(D,L)-(2-norbornyl)Gly-Pro-NH-3-(6-CN)-pico was converted via the hydroxyamidine to the amidine, and subsequently the t-butyl ester was cleaved with HCl. The final product was obtained after purification as crystalline white powder. FAB-MS (M+H$^+$): 457.

EXAMPLE 78

N-(t-Butoxycarbonylmethyl)-(D) or (L)-(4-tetrahydropyranyl)-glycylpipecolic acid 6-amidino-3-picolylamide (a) Coupling of Boc-(D,L)-Thpg-OH with methyl (L)-pipecolate hydrochloride (b) Hydrolysis with 1 N lithium hydroxide (c) Coupling of the dipeptide acid with 6-carbamoyl-3-picolylamine dihydrochloride (d) Dehydration of the carbamoyl group with trifluoroacetic anhydride to give the nitrile (e) Elimination of the Boc protective group with isopropanolic hydrochloric acid (f) Alkylation of the Thpg nitrogen with t-butyl bromoacetate (g) Addition of hydroxylamine onto the cyano group (h) Catalytic hydrogentation of the N-hydroxyamidine with Pd/C in methanol (i) Separation of the diastereomers by preparative thick-layer chromatography, mobile phase: CH$_2$Cl$_2$/MeOH/50% strength acetic acid (24/6/1.5).

Acetate of isomer I:
white crystals, melting point 168–170° C. (decomposition), Rf 0.21; FAB-MS (M+H$^+$): 517

Acetage of isomer II:
white crystals, melting point 97–98° C. (decomposition), Rf 0.16; FAB-MS (M+H$^+$): 517.

EXAMPLES 79 and 80

N-(Hydroxycarbonylmethyl)-(D)- or (L)-(4-tetrahydropyranyl)-glycylpipecolic acid 6-amidino-3-picolylamide The separated diastereomers from Example 78, stage (i) were hydrolyzed with trifluoroacetic acid to give the trifluoroacetates of the carboxylic acides and converted by chromatography on silica gel (eluent: methanol/25% strength aqueous $NH_3$, 25/1) into the free betaines.

Isomer I: Melting point 157–160° C. (decomposition), Rf 0.28 (mobile phase: MeOH/25% strength aqueous $NH_3$ (50/2.5)); FAB-MS (M+H $^+$): 461.

Isomer II: Melting point 132–135° C. (decomposition), RF 0.24; FAB-MS (M+H$^+$): 461.

EXAMPLE 81

N-(Hydroxycarbonylmethyl)-(D,L)-(4-tetrahydropyranyl)-glycyl-1,3-oxazolidine-4-carboxylic acid 6-amidino-3-picolyl-amide 6.1 g (12.9 mmol) of Boc-(D,L)-Thpg-Oxp 6-CN-3-picolylamide, which had been prepared as in Example 68 from Boc-(D,L)-Thpg-OH and H-Oxp 6-carbamoyl-3-picolylamide (see also Example 98)) were converted by the process described in Example 68 into 0.2 g of HOOC—$CH_2$-(D,L)-Thpg-Oxp 6-CN-3-picolylamide dihydrochloride with a purity of 95.6%; FAB-MS (M+H$^+$): 449.

EXAMPLE 82

N-(Hydroxycarbonylmethyl)-(D)-cyclohexylglycyl-1,3-thiazolidine-4-carboxylic acid 6-amidino-3-picolylamide (a) 10.0 g of Boc-Thia-OH and 10.6 g of 3-aminomethyl-6-carbamoylpyridinex2 HCl were reacted as in Example 23 to give 12.9 g of Boc-Thia-NH-3-(6-carbamoyl)-pico. FAB-MS (M$^+$): 366

(b) 12.5 g of Boc-Thia-NH-3-(6-carbamoyl)-pico were deprotected with TFA/DCM. After workup, 14.9 g of H-Thia-NH-3-(6-carbamoyl-picox2TFA remained. FAB-MS (M+H$^+$): 267

(c) 6.9 g of Boc-(D)-Chg and 14.5 g of H-Thia-NH-3-(6-carbamoyl)-picox2 TFA were reacted as in Example 23 with PPA to give 11.7 g of Boc-(D)-Chg-Thia-NH-3-(6-carbamoyl)-pico. FAB-MS (M$^+$): 505

(d) 11.5 g of Boc-D-Chg-Thia-NH-3-(6-carbamoyl)-pico were converted as in Example 23 with TFAA to 8.6 g of the nitrile Boc-(D)-Chg-Thia-NH-3-(6-CN)-pico. FAB-MS (M$^+$): 487

(e) 8.5 g of Boc-(D)-Chg-Thia-NH-3-(6-CN)-pico were reacted with TFA/DCM to give 9.9 g of H-(D)-Chg-Thia-NH-3-(6-CN)-picox2 TFA. FAB-MS (M+H$^+$): 388

(f) 9.5 g of Boc-(D)-Chg-Thia-NH-3-(6-CN)-picox2 TFA were reacted with 3.6 g of t-butyl bromoacetateas in Example 68 to give 5.6 g of t-BuOOCCH$_2$-(D)-Chg-Thia-NH-3-(6-CN)-pico. FAB-MS (M$^+$): 501

(g) 5.4 g of t-BuOOC—CH$_2$-(D)-Chg-Thia-NH-3-(6-CN)-pico were converted with (Boc)$_2$O into 5.1 g of the corresponding Boc-protected derivative t-BuOOCCH$_2$-D-(Boc)Chg-Thia-NH-3-(6-CN)-pico. FAB-MS (M$^+$): 602

(h) 5.0 g of t-BuOOC—CH$_2$-(D)-(Boc)Chg-Thia-NH-3-(6CN)-pico were converted as in Example 1b into the amidine. After workup, 3.5 g of t-BuOOCCH$_2$-D-(Boc)Chg-Thia-NH-3-(6-am)-pico were isolated. FAB-MS (M+H$^+$): 680

(i) 3.3 g of t-BuOOC—CH$_2$-(D)-(Boc)Chg-Thia-NH-3-(6-CN)-pico were deprotected as in Example 68 to give the free compound HOOC—CH$_2$-(D)-Chg-Thia-NH-3-(6-am)-pico. Yield: 1.6 g; FAB-MS (M$^+$): 462

EXAMPLE 83

N-(t-Butoxycarbonylmethyl)-(D)-cyclohexylglycylproline 6-hydroxy-amidino)-3-picolylamide (a) Boc-(D)-Cyclohexylglycylproline 6-carbamoyl-3-picolylamide 89 g (0.251 mol) of Boc-(D)-Chg-Pro-OH and 56.2 g (0.251 mol) of 6-carbamoyl-3-picolylamine were dissolved or suspended in 500 ml of CH$_2$Cl$_2$. Addition of 162.3 g (1.25 mol) of diisopropylethylamine at RT resulted in them substantially dissolving. After cooling to −15° C., 251 ml (0.326 mol) of propanephosphonic anydride solution (50% strength in ethyl acetate) were added dropwise, during which the temperature rose to about −520 C. The mixture was left to stir at −5° C. for 2 h. The methylene chloride phase was washed with water, 5% strength NaHCO$_3$ and 0.5 N KHSO$_4$ solution, dried over Na$_2$SO$_4$ and evaporated to dryness. 106.5 g (87%) of white crystals were isolated, melting point 133–135° C.

(b) Boc-(D)-Cyclohexylglycylproline 6-cyano-3-picolylamide 31.5 g (0.15 mol) of trifluoroacetic anhydride were added dropwise to a solution of 48.8 g (0.1 mol) of the above compound and 36.3 g (0.36 mol) of triethylamine in 350 ml of CH$_2$Cl$_2$ at −5° C., and the mixture was stirred for 15 min. The solution was washed with water, 5% strength NaHCO$_3$ and 10% strength KHSO$_4$ solution, dried over Na$_2$SO$_4$ and distilled to remove methylene chloride. 38.5 g (82%) of pale yellowish crystals were isolated. A sample recrystallized from ethyl acetate/n-hexane melted at 150–151° C.

(c) (D)-Cyclohexylproline 6-cyano-3-picolylamide

Elimination of the Boc protective group took place with isopropanolic hydrochloric acid.

(d) N-(t-Butoxycarbonylmethyl)-(D)-cyclohexylglycylproline 6-cyano-3-picolylamide 75 g (0.185 mol) of the isopropanol-containing hydrochloride obtained from the above Boc cleavage were suspended in 350 ml of acetonitrile and, while stirring at RT, 90.8 g (0.73 mol) of diisopropylethylamine were added, resulting in a clear solution. Subsequently, at 20–25° C., 36 g (0.184 mol) of t-butyl bromoacetate were added dropwise over the course of 30 min, and the mixture was left to stir at RT for 2 days. After this, the TLC revealed only small amounts of remaining starting compound and traces of the dialkylation product (TLC: CH$_2$Cl$_2$/acetone/MeOH, 45/5/2).

For isolation, the acetonitrile and excess DIPEA were substantially removed by distillation under reduced pressure at 40° C., the residue was taken up in 280 ml of MTB and 30 ml of CH$_2$Cl$_2$, and the solution was extracted with 100 ml of water and then washed 2x with 50 ml of water each time.

To remove residues of initial base, the organic phase was extracted with a solution of 0.9 g of sulfamic acid (≙ 0.05 equivalent of initial base) in 10 ml of water. Two washes with 30 ml of water and 5% strength NaHCO$_3$ solution were followed by drying over Na$_2$SO$_4$ and then removal of the solvent by distillation at 40° C.

The viscous oily residue was dissolved in a mixture of 100 ml of MTB and 200 ml of (i-Pr)$_2$O, 2 ml of water were added and the mixture was stirred while heating gently until a clear solution was obtained. A dense mass of crystals separated out from the solution over the course of 1 h, and was filtered off with suction and washed with a little cold MTB/(i-Pr)$_2$O mixture.

70.9 g (79.3% of theory) of white crystals were isolated, melting point 89–91° C. TLC: $CH_2Cl_2$/acetone/MeOH, 45/5/2 or MTB/EtOH, 45/5

(e) N-(t-Butoxycarbonylmethyl)-(D)-cyclohexylglycylproline 6-hydroxyamidino-3-picolylamide 50 g (0.72 mol) of hydroxylamine hydrochloride were suspended in 800 ml of $CH_2Cl_2$ and, while stirring, 92.8 g (0.85 mol) of diisopropylethylamine were added, and the mixture was stirred at RT for 30 min. 180 g (0.37 mol) of nitrile compound were added to this, and the mixture was stirred overnight. The reaction solution was washed 3× with 150 ml of water, dried over $Na_2SO_4$ and distilled to remove methylene chloride.

The viscous oily residue was mixed with 600 ml of ethyl acetage and heated, whereup the hydroxyamidine rapidly separated out as a mass of white crystals. After 30 min, they were filtered off with suction and washed with cold ethyl acetate and finally with n-hexane. 175 g (91% of theory) of white crystals were obtained, melting point 154–156° C.

10 g of amorphous yellowish residue remained in the mother liquor and substantially consisted of hydroxyamidine.

EXAMPLE 84

N-(Benzyloxycarbonylmethyl)-(D)-cyclohexylglycylproline 6-hydroxyamidino)-3-picolylamide:

The compound was obtained as in Example 83, using benzyl bromoacetate for alkylation in stage (d). White crystals, melting point 124–125° C.; FAB-MS ($M+H^+$): 551.

EXAMPLE 85

N-(Methoxycarbonylmethyl)-(D)-cyclohexylglycylproline 6-methoxycarbonylamidino-3-picolylamide:

(a) Boc-(D)-Cyclohexylglycylproline 6-methoxycarbonylamidino-3-picolylamide:

A solution of 0.5 g (12.5 mmol) of NaOH in 4 ml of water was added to a suspension of 5.47 g (10 mmol) of Boc-(D)-cyclohexylglycylproline 6-amidino-3-picolylamide acetate in 40 ml of $CH_2Cl_2$ at 0° C. while stirring vigorously. After stirring for 5 min, a clear interphase system had formed, into which solutions of 0.9 g (9.5 mmol) of methyl chloroformate in 5 ml of $CH_2Cl_2$ and of 0.6 g of NaOH in 7 ml of water were simultaneously added dropwise.

After 10 min, the mixture was washed with water, 5% strength citric acid and 7% strength $NaHCO_3$ solution, dried over $Na_2SO_4$ and evaporated to dryness. 4.8 g of a foam-like residue which was pure by TLC ($CH_2Cl_2$/acetone/methanol, 45/5/3) were isolated.

(b) (D)-Cyclohexylglycylproline 6-methoxycarbonylamidino-3picolylamide:

The above compound (8.8 mmol) was dissolved in 35 ml of tri-fluoroacetic acid and, after 5 min, concentrated under reduced pressure. The residue was treated with ether, whereupon a white powder formed, and this was dissolved in 10 ml of $CH_2Cl_2$ and shaken with 30 ml of 1 N NaOH. The organic phase was separated off, dried over $Na_2SO_4$ and concentrated. Renewed treatment of the residue with ether gave 3.5 g of white crystalline powder (TLC: $CH_2Cl_2$/MeOH/50% strength acetic acid, 40/10/2.5).

(c) N-(Methoxycarbonylmethyl)-(D)-cyclohexylglycylproline 6-methoxycarbonylamidino-3-picolylamide The above compound (7.4 mmol) was dissolved in 15 ml of $CH_2Cl_2$, and 2.9 g (22.2 mmol) of diisopropylethylamine and 1.2 g (7.4 mmol) of methyl bromoacetate were added. After standing overnight, the solution was concentrated, the residue was taken up in 90 ml of ethyl acetate, and the solution was washed with water, 5% strength citric acid and 5% strength $NaHCO_3$ solution, dried and distilled.

The residue was mixed with 50 ml of ether, adding a little ethyl acetate and 0.1 ml of water to produce a solution, which was left to stand overnight. The crystals which had separated out were filtered off with suction and recrystallized from ethyl acetate. 22.4 g (63%) of white crystals were isolated, melting point 95–97° C.; FAB-MS ($M+H^+$): 517.

EXAMPLE 86

N-(t-Butoxycarbonylmethyl)-(D)-(t-butyl)glycylpipecolic acid 6-amidino-3-picolylamide:

The title compound was obtained as in Example 78 starting from Boc-t-butylglycine and methyl pipecolate hydrochloride. Acetate: white crystals, melting point 170–171° C. (decomposition); FAB-MS ($M+H^+$): 489.

EXAMPLE 87

N-(Hydroxycarbonylmethyl)-(D)-(t-butyl)glycylpipecolic acid 6-amidino-3-picolylamide:

The above t-butyl ester was cleaved with trifluoroacetic acid and converted into the betaine by chromatography on silica gel (eluent: methanol/conc. $NH_3$, 25/1). White crystals, melting point 145–147° C. (decomposition); FAB-MS ($M+H^+$): 433.

EXAMPLE 88

N-(t-Butoxycarbonylmethyl)-(D)-(neopentyl) glycylpipecolic acid 6-amidino-3-picolylamide:

The title compound was obtained as in Example 78 starting from Boc-neopentylglycine and methyl pipecolate hydrochloride. Acetate: white crystals, melting point 154–155° C.; FAB-MS ($M+H^+$): 503.

EXAMPLE 89

N-(Hydroxycarbonylmethyl)-(D)-(neopentyl) glycylpipecolic acid 6-amidino-3-picolylamide:

The compound was obtained as in Example 87 from the above t-butyl ester, white crystals, melting point 176–177° C. (decomposition); FAB-MS ($M+H^+$): 477.

EXAMPLE 90

N-(Hydroxycarbonylethyl)-(D)-cyclohexylglycylproline 6-amidino-3-picolylamide:

2.6 g (20 mmol) of t-butyl acrylate were added to a solution of 7.38 g (20 mmol) of D-cyclohexylglycylproline 6-cyano-3-picolylamide (Example 83, stage c) in 45 ml of ethanol, and the mixture was heated at 45–60° C. for 40 h. The solvent was then removed by distillation, and the residue was purified by column chromatography (eluent: $CH_2Cl_2$/acetone/$CH_2Cl_2$, 45/5/3). 7.5 g (75%) of a pale yellowish foam were isolated; FAB-MS ($M+H^+$): 498.

This was converted into the amidine as in Examples 83 and 102, and subsequently the tert-butyl group was eliminated with tri-fluoroacetic acid, and the betaine was liberated with ammonia. Amorphous powder; FAB-MS ($M+H^+$): 459.

EXAMPLE 91

N-(Hydroxycarbonylmethyl)-(D,L)-(3,4,5-trimethoxy) phenylalanylproline 6-amidino-3-picolylamide acetate:

As in Example 68, starting from Boc-(D,L)-(3,4,5-trimethoxy)Phe-Pro—NH—3-(6—CN)-pico (Example 29), first the Boc protective group was eliminated, the free amine was alkylated with tert-butyl bromoacetate, the cyano group was converted via the hydroxyamidine into the amidine, the tert-butyl ester was cleaved and the crude product was purified by MPLC on an RP column, and the solutions were lyophilized. HOOC—CH$_2$—(D,L)-(3,4,5-trimethoxy)Phe-Pro—NH—3-(6-am)-pico acetate was obtained as an amorphous powder. FAB-MS (M+H$^+$): 543

EXAMPLE 92

N-(Hydroxycarbonylmethyl)-(D)-cyclohexylalanylproline 6-amidino-2-methyl)picolylamide:

(a) Preparation of Boc-(D)-Cha-Pro—NH—3-(2-Me)-pico:

6.6 g of Boc-(D)-Chg-Pro—OH (18.05 mmol) were introduced together with 4.0 g of 2-methyl-3-picolylamine (20.5 mmol, for preparation, see Arch. Pharm. 308 (1975) 969–76 and 14 ml of DIPEA (81.8 mmol) into 200 ml of DCM and, after cooling to 5° C., 18.8 ml of 50% strength propanephosphonic anhydride solution in ethyl acetate (23.92 mmol) were added dropwise. Reaction was allowed to continue for 1 h after warming to room temperature, and the mixture was then concentrated under reduced pressure. The residue was taken up in ethyl acetate, and the ethyl acetate phase was extracted about 10 times with water, dried over magnesium sulfate and concentrated in a rotary evaporator. The residue was stirred with diisopropyl ether to result in 7.4 g (87%) of Boc-(D)-Chg-Pro—NH—3-(2-Me)-pico as white solid.

(b) Preparation of H—(D)-Cha-Pro—NH—3-(2-Me)pico:

8.0 g of Boc-(D)-Cha-Pro—NH—3-(2-Me)-pico (17.0 mmol) were stirred in 35 ml of DCM and 35 ml of ethereal hydrochloric acid (>3 M) at room temperature for 2 h, concentrated under reduced pressure and codistilled several times with methanol/DCM, and the residue was extracted by stirring with ether. 7.5 g (100%) of H—(D)-Cha-Pro—NH—3-(2-Me)-pico×2 HCl were obtained as a white solid.

c) Preparation of tBuOOC—CH$_2$—(D)-Cha-Pro—NH—3-(2-Me)-pico:

9.7 g of H—(D)-Chg-Pro—NH—3-(2-Me)-pico×2 HCl (21.79 mmol) were stirred together with 11.26 g (14.9 ml) of DIPEA (81.16 mmol) and 4.89 g(3.69 ml) of tert-butyl bromoacetate (25.0 mmol) in 150 ml of DCM (dried over molecule sieves) at room temperature for 16 h. Since TLC showed that precursor was still present, a further 0.4 ml of tert-butyl bromoacetate and 1.5 ml of DIPEA were added, and the mixture was stirred at RT for a further 3 h. The reaction mixture was then concentrated first under a water pump vacuum and then under 1 mbar at max. 40° C. The residue was extracted by stirring with ether, filtered off and washed with ether. The crystals were taken up in water and, at pH 7.5, extracted several times with ethyl acetate, and there ethyl acetate extracts were combined with the above ether filtrate, dried and concentrated under reduced pressure. The residue was taken up in ether and then ethereal hydrochloric acid was added to pH 3, the precipitate was filtered off with suction, thoroughly washed with ether and then extracted by stirring twice with ether. 9.3 g (82%) of tBuOOC—CH$_2$—(D)-Cha-Pro—NH—3-(2-Me)-pico×HCl were obtained as a white solid.

d) Preparation of t-BuOOC—CH$_2$—(Boc)(D)-Cha-Pro—NH—3-(2-Me)-pico:

9.8 g of tBuOOC—CH$_2$—(D)-Cha-Pro—NH—3-(2-Me)-pico×HCl (18.66 mmol) were introduced together with 18.66 g of (Boc)$_2$O (18.66 mmol) into 160 ml of DCM and, over the course of 5 min, 5.3 g (7.03 ml) of DIPEA (41.05 mmol) were added, and the mixture was then stirred at RT overnight. After further addition of DCM, washing was carried out with 0.5 M HCl solution until DIPEA was no longer present in the DCM (TLC check), and the solution was dried over magnesium sulfate and concentrated under reduced pressure.

Column chromatography on silica gel with DCM and 0–5% methanol resulted in 5.9 g (54%) of tBuOOC—CH$_2$—(Boc)(D)-Cha-Pro—NH—3-(2-Me)-pico as white solid.

e) Preparation of tBuOOC—CH$_2$—(Boc)(D)-Cha-Pro—NH—3-(2-Me-1-Oxo)-pico:

5.9 g of tBuOOC—CH$_2$—(Boc)-(D)-Cha-Pro—NH—3-(2-Me)-pico (10.12 mmol) were stirred together with 9.99 g of 70% pure m-chloroperbenzoic acid (40.5 mmol) in 200 ml of DCM at RT for 2 h. Gaseous ammonia was then passed in to saturation, the mixture was stirred at room temperature for 1 h, the precipitate was filtered off with suction and washed with DCM, and the filtrate was again saturated with ammonia. The DCM phase was then washed 3 times with water, dried over magnesium sulfate and concentrated under reduced pressure. 6.1 g (100%) were obtained.

f) Preparation of tBuOOC—CH$_2$—(Boc)(D)-Cha-Pro—NH—3-(2-Me-1-MeO)-pico$^\oplus$—CH$_3$OSO$_3^\ominus$:

6.1 g of tBuOOC—CH$_2$—(Boc)-(D)-Cha-Pro—NH—3-(2-Me-1-Oxo)-pico (10.12 mmol) were dissolved in 25 ml of DCM, and 28 ml of a 5% strength dimethyl sulfate solution in DCM were added. The mixture was stirred at 40° C. for 5 h and left to stand at RT overnight and then diluted to 100 ml with DCM, rapidly washed 3 times with water, dried over magnesium sulfate and concentrated under reduced pressure. The resulting tBuOOC— CH$_2$—(Boc)-(D)-Cha-Pro—NH—3-(2-Me-1-MeO)-pico$^\oplus$—CH$_3$OSO$_3^\ominus$ was used as crude product in the next reaction.

g) Preparation of tBuOOC—CH$_2$—(Boc)-(D)-Cha-Pro—NH—3-(2-Me-6—CN)-pico:

The crude tBuOOC—CH$_2$—(Boc)(D)-Cha-Pro—NH—3-(2-Me-1-MeO)-pico$^\oplus$CH$_3$OSO$_3^\ominus$ obtained from the above reaction was added dropwise over the course of 20 min to a solution of 1.1 g of sodium cyanide (21.3 mmol) in 50 ml of DMF, keeping the temperature at 23–25° C. by cooling. After a further 20 min, DMF was removed by distillation under reduced pressure (1 mbar), the residue was taken up in ether, and the ether phase was washed successively with water, KHSO$_4$ solution (pH 2), water and saturated brine, dried over magnesium sulfate and concentrated under reduced pressure. Purification by column chromatography on silica gel (eluent: DCM wit 0–2% MeOH) resulted in 4.1 g of solid which was extracted by stirring with ether.

Yield: 4.1 g (66%) of tBuOOC—CH$_2$—(Boc)(D)-Cha-Pro—NH—3-(2-Me-6—CN)-pico h) Preparation of tBuOOC—CH$_2$—(Boc)(D)-Cha-Pro—NH—3-(2-Me-6-ham)-pico:

4.0 g of tBuOOC—CH$_2$—(Boc)(D)-Cha-Pro—NH—3-(2-Me-6—CN)-pico (6.6 mmol) were refluxed together with 1.15 g of hydroxylamine hydrochloride (16.52 mmol) and 5.12 g (6.78 ml) of DIPEA (39.6 mmol) in 75 ml of DCM (dried over molecular sieves) for 2 h and then stirred at RT overnight. After addition of further DCM, the mixture was washed with dilute hydrochloric acid (pH 4), and the organic phase was dried over magnesium sulfate and concentrated under reduced pressure. The resulting 4.3 g of crude tBuOOC—CH$_2$—(Boc)(D)-Cha-Pro—NH—3-(2-Me-6-ham)-pico were used as crude product in the next reaction.

i) Preparation of tBuOOC—CH$_2$—(Boc)-(D)-Cha-Pro—NH—3-(2-Me-6-am)-pico:

4.3 g of crude tBuOOC—CH$_2$—(Boc)-(D)-Cha-Pro—NH—3-(2-Me-6-ham)-pico were hydrogenated in a mixture of 15 ml of acetic acid and 80 ml of ethanol over Pd/C (10%) with hydrogen at 50° C. for 5 h. The catalyst was then filtered off and washed with ethanol, the filtrate was concentrated under reduced pressure (1 mbar), and the residue was codistilled several times with toluene/DCM, taken up in 100 ml of ether and washed 3 times with 4 ml of water each time. The combined aqueous phases were concentrated under reduced pressure (1 mbar) at 35–40° C., and the residue was codistilled with ethanol. 4.3 g of almost pure tBuOOC—CH$_2$—(Boc)-(D)-Cha-Pro—NH—3-(2-Me-6-am)-pico×CH$_3$COOH were obtained (94% over two stages) as white solid.

j) Preparation of HOOC—CH$_2$—(D)-Cha-Pro—NH—3—(2-Me-6-am)-pico:

2.24 g of tBuOOC—CH$_2$—(Boc-(D)-Cha-Pro—NH—3-(2-Me-6-am)-pico×CH$_3$COOH (3.25 mmol) were stirred in 30 ml of DCM together with 15 ml of ethereal hydrochloric acid at room temperature for several hours, during which a solid slowly precipitated. The solid was filtered off with suction, extracted by stirring with hot DCM several times and subsequently chromatographed on silica gel (mobile phase methanol/25% aqueous ammonia solution in the ratio 95/5). 1.35 g (94%) of HOOC—CH$_2$—(D)-Cha-Pro—NH—3-(2-Me-6-am)-pico were obtained as a white solid. FAB-MS (M+H$^+$): 473

EXAMPLE 93

(a) tBuOOC—CH$_2$—(D)-Cha-Pyr—NH—3-(6—CN)-pico:

4.3 g of H—(D)-Cha-Pyr—nH—3-(6—CN)-pico (11.27 mmol) (see Example 32) and 5.3 ml of diisopropylethylamine (33.81 mmol) were introduced into 50 ml of methylene chloride and, while stirring at RT, 2.16 g of tertiary-butyl bromoacetate (11.04 mmol) were added dropwise and the mixture was stirred at RT overnight. The solution was diluted with methylene chloride, extracted twice with 5% strength citric acid and twice with saturated NaHCO$_3$ solution, dried over magnesium sulfate and concentrated under reduced pressure. The crude product was taken up in ether, cooled to 0° C. and adjusted to pH 1 with ethereal hydrochloric acid, and the precipitated product was rapidly filtered off with suction, washed several times with ether and dried. 5.85 g of almost pure crystalline product were obtained (≙97% of theory).

(b) tBuOOC—CH$_2$—(Boc)-(D)-Cha-Pyr—nH—3-(6—CN)-pico:

5.8 g of tBuOOC—CH$_2$—CH$_2$—(D)-Cha-Pyr—NH—3-(6—CN)-pico—HCl (11 mmol) were stirred together with 2.4 g of (Boc)$_2$O (11 mmol) and 4.7 ml of diisopropylethylamine in 60 ml of methylene chloride at room temperature overnight and then diluted with about 100 ml of methylene chloride, extracted three times with 5% strength citric acid solution, dried with sodium sulfate and concentrated under reduced pressure. The crude product was purified by column chromatography on silica gel (eluent: methylene chloride with 0 to 5% methanol). The yield of pure product was 4.1 g (≙63% of theory).

(c) tBuOOC—CH$_2$—(Boc)-(D)-Cha-Pyr—NH—3-(6—CSNH$_2$)-pico:

4.1 g tBuOOC—CH$_2$—(Boc)-(D)-Cha-Pyr—NH—3-(6—CN)-pico (6.88 mmol) were dissolved in 25 ml of pyridine and 12 ml of triethylamine and saturated with gaseous hydrogen sulfide and stirred overnight at RT. Nitrogen was blown through the solution which was then substantially concentrated, and the residue was dissolved in 75 ml of ethyl acetate, washed successively with 5% strength citric acid, 20% strength NaHSO$_4$ and twice with saturated NaHCO$_3$ solution, dried over magnesium sulfate and concentrated, resulting in 4.25 g of pure product as a yellow powder. This was dried under high vacuum overnight. Yield: 98% of theory.

(d) tBuOOC—CH$_2$—(Boc)-(D)-Cha-Pyr—NH—3-(6—C(NH)SCH$_3$)-pico×HI:

4.25 g of tBuOOC—CH$_2$—(Boc)-(D)-Cha-Pyr—NH—3-(6—CSNH$_2$)-pico (6.75 mmol) were dissolved in 75 ml of acetone, 4.65 ml of methyl iodide were added, and the mixture was stirred in a closed flask at RT overnight. The reaction solution was completely concentrated, dissolved in the minimum amount of ethyl acetate and added dropwise to 200 ml of n-hexane while stirring, and the solid was filtered off with suction and dried. 5.2 g of yellow powder were obtained. Yield: about 100% of theory.

(e) tBuOOC—CH$_2$—(Boc)-(D)-Cha-Pyr—NH—3-(6-am)-pico×CH$_3$COOH:

5.2 g of tBuOOC—CH$_2$—(Boc)-(D)-Cha-Pyr—NH—3-(6—C(NH)SCH$_3$)-pico×HI (6.74 mmol) were dissolved in 11 ml of methanol, 10.3 ml of 10% strength ammonium acetate solution in methanol were added, and the mixture was stirred at RT overnight. The reaction solution was concentrated, the residue was taken up in ethyl acetate, the mixture was filtered with suction to remove solid, and the solution was substantially concentrated and added dropwise to diisopropyl ether. The precipitated solid was filtered off with suction and dried. The almost pure crude product was completely purified by MPLC on an RP column. 2.58 g of the required compound were obtained as a pale yellow solid. Yield: 57% of theory.

(f) HOOC—CH$_2$—(D)-Cha-Pyr—NH—3-(6-am)-pico×HCl:

2.43 g of tBuOOC—CH$_2$—(Boc)-(D)-Cha-Pyr—NH—3-(6-am)-pico×CH$_3$COOH (3.61 mmol) were added to 15 ml of ethereal hydrochloric acid and stirred at RT for 5 h. The almost pure crude product after concentration under reduced pressure was purified by MPLC on an RP column. 1.77 g of final product were obtained as a white lyophilisate. Yield: 95% of theory, FAB-MS (M+H$^+$): 457.

EXAMPLE 94

N-(Hydroxycarbonylmethyl)-(D,L)-4-tetrahydropyranylalanyl-3,4-dehydroproline 6-amidino-3-picolylamide acetate:

Boc-(D,L)-Thpa-Pyr—NH—3-(6—CONH$_2$)-pico was prepared as in Example 68 c–k starting from Boc-(D,L)-Thpa—O (see above for preparation) and H—Pyr—NH—3-(6—CONH$_2$)-pico HCl (see Example 68), the primary amide functionality was dehydrated to the nitrile, the terminal Boc protective group was eliminated, the free amine was alkylated with tert-butyl bromoacetate, the secondary amine was Boc-protected, the nitrile functionality was converted into the thioamide, and the latter was methylated to give the imino thiomethyl ester, and the latter was reacted with ammonium acetate to give the amidine. After elimination of the protective groups using ethereal hydrochloric acid in methylene chloride and purification of the crude product by MPLC on an RP column, the mixture of diastereomers of HOOC—CH$_2$—(D,L)-Thpa-Pyr—NH—3-(6-am)-pico was obtained as acetate.
FAB-MS (M+H$^+$): 459

EXAMPLE 95
N-(Isopropoxycarbonylmethyl)-(D)-cyclohexylglycyl-3,4-dehydroproline 6-amidino-3-picolylamide acetate:

As in Example 93 a–j, Boc-Pyr—OH was coupled with H$_2$N—3-(6-CONH$_2$)-pico HCl (see above for preparation) to give Boc-Pyr—NH—3-(6—CONH$_2$)-pico, the Boc protective group was eliminated, the free amino group was coupled with Boc-(D)-Chg—OH to give Boc-(D)-Chg-Pyr—NH—3-(6—CONH$_2$)-pico, the primary amide functionality was dehydrated to the nitrile, the terminal Boc protective group was eliminated, the free amine was alkylated with tert-butyl bromoacetate, the secondary amine was Boc-protected, the nitrile functionality was converted into the thioamide, and the latter was methylated to give the imino thiomethyl ester and converted with ammonium acetate into the amidine tBuOOC—CH$_2$—(D)(Boc)Chg-Pyr—NH—3-(6-am)-pico HI. Elimination of the protective groups with isopropanolic hydrochloric acid resulted in two products which were separated by MPLC on an RP column. These were HOOC— CH$_2$—(D)-Chg-Pyr—NH—3-(6am)-pico—CH$_3$COOH
FAB-MS (M+H$^+$): 443
and by esterification iPrOOC—CH$_2$—(D)-Chg-Pyr—NH—3-(6-am)-pico—CH$_3$COOH
FAB-MS (M+H$^+$): 485

EXAMPLE 96
N-(Hydroxycarbonylmethyl)-(D,L)-γ-methylcyclohexylalanyl-3,4-de-hydroproline 6-amidino-3-picolylamide acetate:

Preparation took place as in Example 93. The diastereomeric mixture HOOC—CH$_2$—(D,L)-(γ-Me)Cha-Pyr—NH—3-(6-am)-pico could be separated into the two diastereomers by MPLC on an RP column. FAB-MS (M+H$^+$): 471

EXAMPLE 97
N-(Hydroxycarbonylmethyl)-(D,L)-cycloheptylalanyl-3,4-dehydroproline 6-amidino-3-picolylamide acetate:

Preparation took place as in Example 108. The diastereomeric mixture HOOC—CH$_2$—(D,L)-Cha-Pyr—NH—3-(6-am)-pico could be separated into the two diastereomers by MPLC on an RP column. FAB-MS (M+H$^+$): 471.

EXAMPLE 98
N-(t-Butoxycarbonylmethyl)-(D)-cyclohexylglycyl-(L)-1,3-oxazolidine-4-carboxylic acid 6-amidino-3-picolylamide:

Starting from Boc-(D)-cyclohexylglycine, Boc-(L)-1,3-oxazolidine-4-carboxylic acid (Tetrahedron 50 (1994) 13943) and 6-carbamoyl-3-picolylamine dihydrochloride, the title compound was obtained as in Example 78. Acetate: white crystals, melting point 187–190° C., FAB-MS (M+H$^+$): 503.

EXAMPLE 99
N-(Hydroxycarbonylmethyl)-(D)-cyclohexylglycyl-:(L)-1,3-oxazolidine-4-carboxylic acid 6-amidino-3-picolylamide:

The t-butyl ester (Example 98) was cleaved with trifluoroacetic acid and converted into the betaine with ammonia. White crystals, melting point 210–213° C. (decomposition); FAB-MS (M+H$^+$): 446.

EXAMPLE 100
N-(t-Butoxycarbonylmethyl)-(D)-cyclohexylalanyl-(L)-1,3-oxazolidine-4-carboxylic acid 6-amidino-3-picolylamide:

Acetate: white crystals, melting point 161–163° C. (decomposition); FAB-MS (M+H$^+$): 517.

EXAMPLE 101
N-(Hydroxycarbonylmethyl)-(D)-cyclohexylalanyl-(L)-1,3-oxazolidine-4-carboxylic acid 6-amidino-3-picolylamide:

White crystals, melting point 172–174° C.; FAB-MS (M+H$^+$): 461.

EXAMPLE 102
N-(t-Butoxycarbonylmethyl)-(D)-cyclohexylglycylproline 6-amidino-3-picolylamide:

110 g (0.212 mol) of N-(t-butoxycarbonylmethyl)-(D)-cyclohexylglycylproline 6-hydroxyamidino-3-picolylamide (Example 83) were dissolved in 1.5 l of ethanol and 300 ml of glacial acetic acid, 1.5 g of 10% Pd/carbon were added, and hydrogenation was carried out at about 50° C. (waterbath) for 6 h. The catalyst was filtered off with suction and then the filtrate was concentrated under reduced pressure at a maximum waterbath temperature of 40° C., and the residue was distilled 4× after addition of 200 ml of toluene each time. The remaining brown oil was dissolved in 400 ml of acetone and, after seeding, a thick mass of crystals of the amidine acetate rapidly separated out and were filtered off with suction after 1 h and washed with acetone and finally with ether.

93 g (78% of theory) of acetate were isolated as white crystals, melting point 191–194° C. decomposition); FAB-MS (M+H$^+$): 501.

EXAMPLE 103
N-(Methoxycarbonylmethyl)-(D)-cyclohexylglycylproline 6-amidino-3-picolylamide:

N-(Hydroxycarbonylmethyl)-(D)-cyclohexylproline 6-amidino-3-picolylamide (WO 95/35309) was refluxed in methanolic hydrochloric acid for 12 h. The solvent was stripped off and then the residue was dissolved in water and converted into the acetate using an IRA acetate ion exchanger and subsequently freeze-dried. White powder, melting point 75–76° C.; FAB-MS (M+H$^+$): 459.

EXAMPLE 104
N-(Cyclohexyloxycarbonylmethyl)-(D)-cyclohexylglycylproline 6-amidino-3-picolylamide:

The compound was obtained as in Example 83, using cyclohexyl bromoacetate for alkylation in stage (d). White amorphous powder; FAB-MS (M+H$^+$): 528.

EXAMPLE 105
N,N-bis(t-Butoxycarbonylmethyl)-(D)-cyclohexylglycylproline 6-amidino-3-picolylamide:

A solution of N-(t-butoxycarbonylmethyl)-(D)-cyclohexylglycylproline 6-cyano-3-picolylamide (compound 83, stage d), 1.2 equivalents of t-butyl bromoacetate and diisopropylethylamine was heated at 60–70° C. for 5 h. Workup and subsequent conversion into the amidine took place as for compound 83.

Acetate: white crystals, melting point 208–211° C. (decomposition); FAB-M (M+H$^+$): 615.

EXAMPLE 106
N,N-bis(Hydroxycarbonylmethyl)-(D)-cyclohexylglycylproline 6-amidino-3-picolylamide:

Obtained from Example 105 by elimination of the t-butyl group. White crystals, melting point 211–215° C. (decomposition); FAB-MS (M+H$^+$): 503.

EXAMPLE 107
N-Carbamoylmethyl)-ID)-cyclohexylglycylproline 6-amidino-3-picolylamide:

N-(Methoxycarbonylmethyl)-(D)-cyclohexylglycylproline 6-amidino-3-picolylamide (compound 103) was left to stand in ammonia-saturated methanol overnight. The solvent was stripped off and the residue was codistilled several times with ethanol/toluene. Acetate: white crystals, melting point 87–89° C., FAB-MS (M+H$^+$): 444.

EXAMPLE 108
N-(tert-Butylaminocarbonylmethyl)-(D)-cyclohexylglycylproline 6-amidino-3-picolylamide acetate:

As in Example 68, H-(D)-Chg-Pro—NH—3-(6—CN)-pico (Example 83) was alkylated with chloroacetic acid tert-butylamide to give tBuNH—CO—CH$_2$—(D)-Chg-Pro—NH—3-(6—CN)-pico, and the nitrile functionality was converted via the hydroxyamidine stage into the amidine. Purification by MPLC on an RP column and lyophilization resulted in tBuNH—CO—CH$_2$—(D)-Chg-Pro—NH—3-(6-am)-pico acetate as a white amorphous powder. FAB-MS (M+H$^+$): 500

Examples 109–116 were carried out by the process described above.

EXAMPLE 109
N-(t-Butoxycarbonylmethyl)-(D)-cyclohexylglycylazetidine-2-carboxylic acid 6-amidino-3-piclylamide:
Acetate: white crystals, melting point 176–178° C.; FAB-MS (M+H$^+$): 487.6.

EXAMPLE 110
N-(Hydroxycarbonylmethyl)-(D)-cyclohexylglycylazetidine-2-carboxylic acid 6-amidino-3-picolylamide:
Betaine: white crystals, melting point 162–164° C. (decomposition), FAB-MS (M+H$^+$): 431.

EXAMPLE 111
N-(t-Butoxycarbonylmethyl)-(D)-cyclohexylglycylpipecolic acid 6-amidino-3-picolylamide:
Acetate: white crystals, melting point 175–178° C. (decomposition); FAB-MS (M+H$^+$): 515.5.

EXAMPLE 112
N-(Hydroxycarbonylmethyl)-(D)-cyclohexylglycylpipecolic acid 6-amidino-3-picolylamide:
Betaine: white crystals, melting point 128–130° C. (decomposition); FAB-MS (M+H$^+$): 459.

EXAMPLE 113
N-(t-Butoxycarbonylmethyl)-(D)-cyclohexylalanylproline 6-amidino-3-picolylamide:
Acetate: white crystals, melting point 83–85° C. (decomposition); FAB-MS; 515 (M+H$^+$).

EXAMPLE 114
N-(Hydroxycarbonylmethyl)-(D)-cyclohexylalanylproline 6-amidino-3-picolylamide:
Betaine: white crystals, melting point 158–162° C. (decomposition); FAB-MS; 459 (M+H$^+$).

EXAMPLE 115
N-(t-Butoxycarbonylmethyl)-(D)-cyclohexylalanylpipecolic acid 6-amidino-3-picolylamide:
Acetate: white crystals, melting point 161–164° C. (decomposition); FAB-MS: 529.5 (M+H$^+$).

EXAMPLE 116
N-(Hydroxycarbonylmethyl)-(D)-cyclohexylalanylpipecolic acid 6-amidino-3-picolylamdie:
Betaine: white crystals, melting point 74–76° C.; FAB-MS (M+H$^+$): 473.

EXAMPLE 117
N-(Hydroxycarbonylmethyl)-(D,L)-cyclooctylglycylproline 2-amidino-5-pyrimidylmethylamide:

(a) 2.72 g of Boc(D,L)-Cog—OH and 6.9 g of the crude H-Pro-5-(2—CN)-pym×2 TFA (see above) were combined together with 9.8 ml of DIPEA and 10.1 ml of PPA (50% strength in ethyl acetate) in 40 ml of . . . at 0° C. The reaction mixture was allowed slowly to reach RT over the course of 18 h. The reaction solution was then diluted with 200 ml of ethyl acetate, and the resulting solution was washed with water, 5% strength citric acid and 2× with saturated NaHCO$_3$ solution. The organic solution was dried with MgSO$_4$ and then ethyl acetate was removed under reduced pressure. 4.88 g of the crude product remained and were used without further purification in the next stage.

(b) 4.88 g of the crude Boc-(D,L)-Cog-Pro—NH—5-(2—CN)-pym were stirred in 100 ml of methylene chloride with 7.6 ml of TFA at RT for 18 h. The solution was ten concentrated under reduced pressure and the residue was purified by column chromatography on silica gel (DCM/MeOH 95:5+1% conc. ammonia solution). 3.3 g of H-(D)-Cog-Pro—NH—5-(2—CN)-pym remained; FAB-MS (M$^+$) 498

(c) 3.3 g of H-(D)-Cog-Pro—NH—5-(2—CN)-pym were introduced together with 1.5 g of KI and 1.26 g of potassium carbonate into 30 ml of acetonitrile. Then 1.24 ml of t-butyl bromoacetate were added in portions. After the reaction mixture had been stirred for 18 h it was filtered, the filter cake was washed with acetonitrile, and the combined filtrates were concentrated under reduced pressure. The residue was then taken up in ethyl acetate, the organic solution was extracted 3× with water and 1× with saturated NaCl solution and, after the solution had been dried with MgSO$_4$, ethyl acetate was removed under reduced pressure. 4.2 g of the crude product remained. This was purified by column chromatography (DCM/MeOH 98:2+1% conc. ammonia solution). 1.76 g of the product remained. FAB-MS (M$^+$): 398

(d) 1.76 g of t-BuOOC—Ch$_2$—(D)-Cog-Pro—NH—5-(2—CN)-pym were dissolved in 35 ml of ethanol. After addition of 0.6 g of hydroxylammonium chloride and 3.2 ml of DIPEA, the solution was heated to 60° C. and stirred at this temperature for 2.5 h. The heating bath was then removed, and the reaction mixture was stirred for a further 18 h. After concentration of the reaction solution, the crude product was dissolved in 60 ml of methylene chloride and the solution was extracted 3× with 5 ml of acetic acid and 1× with saturated NaCl solution and dried with Na$_2$SO$_4$, and the solvent was removed under reduced pressure. 2.0 g of the crude product remained and were used without further purification in the next stage.

(e) 2 g of the crude N-hydroxyamidine derivative were dissolved in 35 ml of ethanol and 1.75 ml of glacial acetic acid. Addition of 2 g of Raney nickel and reduction with hydrogen (atmospheric pressure) resulted in the product tBuOOC—CH$_2$—(D)-Chg-Pro—nH—5-(2-am)-pym. It was purified from impurities by column chromatography (methylene chloride/MeOH/50% strength HOAc 40:10:2). Concentration of the fractions resulted in 420 mg of the required product remaining. FAB-MS (M$^+$): 529

(f) 420 mg of tBuOOC—CH$_2$—(D)-Cog-Pro—NH—5-(2-am)-pym were stirred in 4 ml of DCM/TFA (1:1) at RT for 18 h. The solution was then concentrated. The remaining crude product was purified by column chromatography on silica gel (MeOH/25% strength aqueous ammonia solution 100:3). The concentrated eluate was dissolved in water and stirred together with active carbon. After the active carbon had been removed by filtration, the filtrate was frozen and lyophilized. 166 mg of the product remained.

FAB-MS (M$^+$): 473.

We claim:

1. A compound of the formula

H$_2$N—CH$_2$—G—M where M is —C≡N, and G is either

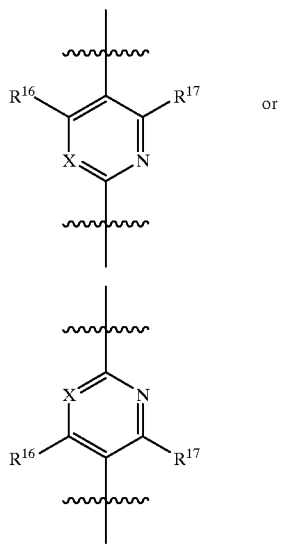

where $R^{16}$ and $R^{17}$ are selected from the group H, F, Cl, C$_1$–C$_4$-alkyl, phenyl-C$_{1-2}$-alkyl, phenyl, $R^{31}$OOC—, $R^{31}$—NH—, $R^{31}$—O— and $R^{31}$OOC—CH$_2$—O—; where $R^{31}$ is selected from H, C$_1$–C$_4$-alkyl, phenyl and benzyl; and X is =N—.

* * * * *